US012636512B2

(12) United States Patent
Iger et al.

(10) Patent No.: US 12,636,512 B2
(45) Date of Patent: May 26, 2026

(54) ESTHETIC APPARATUS USEFUL FOR INCREASING SKIN REJUVENATION AND METHODS THEREOF

(71) Applicant: VENUS CONCEPT INC., Toronto (CA)

(72) Inventors: Yoni Iger, Haifa (IL); Ognjen Petrovic, San Jose, CA (US); Haim Epshtein, Pardes Hana-Karkur (IL); Cliff Oostman, Hansville, WA (US); Vadim Polyakov, Petach Tikva (IL)

(73) Assignee: VENUS CONCEPT INC., Toronto (CA)

( * ) Notice: Subject to any disclaimer, the term of this patent is extended or adjusted under 35 U.S.C. 154(b) by 1020 days.

(21) Appl. No.: 17/695,725

(22) Filed: Mar. 15, 2022

(65) Prior Publication Data

US 2022/0203112 A1 Jun. 30, 2022

Related U.S. Application Data

(60) Continuation-in-part of application No. 16/864,862, filed on May 1, 2020, now Pat. No. 11,890,486, (Continued)

(51) Int. Cl.
*A61N 2/00* (2006.01)
*A61B 18/00* (2006.01)
(Continued)

(52) U.S. Cl.
CPC ................ *A61N 2/002* (2013.01); *A61F 7/00* (2013.01); *A61F 7/007* (2013.01); *A61N 1/328* (2013.01);
(Continued)

(58) Field of Classification Search
CPC ........ A61N 2/002; A61N 1/328; A61N 1/403; A61N 2/004; A61N 2/02; A61N 5/00;
(Continued)

(56) References Cited

U.S. PATENT DOCUMENTS 1,918,386 A 7/1933 Esau
4,140,130 A 2/1979 Storm, III
(Continued)

FOREIGN PATENT DOCUMENTS

CN 101041100 9/2007
CN 102971047 3/2013
(Continued)

OTHER PUBLICATIONS

Search Report in EP 22837145.6 DTD Mar. 27, 2025.
(Continued)

*Primary Examiner* — Carrie R Dorna
*Assistant Examiner* — Joshua Daryl D Lannu
(74) *Attorney, Agent, or Firm* — Foley & Lardner LLP

(57) ABSTRACT

A system is provided for increasing skin rejuvenation of a region of a patient's skin comprising a pulsed electromagnetic field (PEMF) frequency generator for constantly providing electromagnetic pulses to said region of a patient's skin and a deep tissue diathermy device for constantly applying heat to said region of a patient's skin up to temperature T. The system is adapted for simultaneously applying heat and PEMF to the region of a patient's skin. Application of the system increases skin rejuvenation such that the skin rejuvenation increase (SRI) is greater than the sum of the SRI provided by electromagnetic pulses increase and the SRI provided by the deep tissue diathermy device increase.

48 Claims, 29 Drawing Sheets

Related U.S. Application Data which is a continuation of application No. 15/728,560, filed on Oct. 10, 2017, now Pat. No. 10,661,093, which is a continuation of application No. 15/341,010, filed on Nov. 2, 2016, now Pat. No. 9,901,743, which is a continuation of application No. 14/845,315, filed on Sep. 4, 2015, now Pat. No. 9,814,897, which is a division of application No. 14/489,572, filed on Sep. 18, 2014, now Pat. No. 9,694,194, which is a division of application No. 13/954,320, filed on Jul. 30, 2013, now Pat. No. 8,979,727, which is a division of application No. 13/001,834, filed as application No. PCT/IL2009/000644 on Jun. 29, 2009, now Pat. No. 8,998,791.

(60) Provisional application No. 63/161,471, filed on Mar. 16, 2021, provisional application No. 61/112,783, filed on Nov. 10, 2008, provisional application No. 61/076,652, filed on Jun. 29, 2008.

(51) Int. Cl.

| | |
|---|---|
| ***A61B 18/20*** | (2006.01) |
| ***A61B 90/00*** | (2016.01) |
| ***A61B 90/50*** | (2016.01) |
| ***A61F 7/00*** | (2006.01) |
| ***A61N 1/32*** | (2006.01) |
| ***A61N 1/40*** | (2006.01) |
| ***A61N 2/02*** | (2006.01) |
| ***A61N 5/00*** | (2006.01) |
| ***A61N 5/06*** | (2006.01) |
| ***A61N 7/02*** | (2006.01) |
| *A61N 7/00* | (2006.01) |

(52) U.S. Cl.

CPC ............ *A61N 1/403* (2013.01); *A61N 2/004* (2013.01); *A61N 2/02* (2013.01); *A61N 5/00* (2013.01); *A61N 5/0625* (2013.01); *A61N 7/02* (2013.01); *A61B 2018/00452* (2013.01); *A61B 18/203* (2013.01); *A61F 2007/0052* (2013.01); *A61N 2007/0034* (2013.01)

(58) Field of Classification Search

CPC .................... A61N 5/0625; A61N 7/02; A61N 2007/0034; A61N 5/0616; A61N 5/062; A61N 2005/0626; A61F 7/00; A61F 7/007; A61F 2007/0052; A61B 18/203; A61B 2018/00452; A61B 2090/033; A61B 2090/064; A61B 2090/3735; A61B 2090/378; A61B 90/50

See application file for complete search history.

(56) References Cited

U.S. PATENT DOCUMENTS

| | | | | |
|---|---|---|---|---|
| 4,197,851 | A | 4/1980 | Fellus | |
| 4,233,986 | A | 11/1980 | Tannenbaum | |
| 4,262,672 | A | 4/1981 | Kief | |
| 5,248,312 | A | 9/1993 | Langberg | |
| 5,336,217 | A | 8/1994 | Buys et al. | |
| 5,476,478 | A | 12/1995 | Jackson | |
| 5,571,154 | A | 11/1996 | Ren | |
| 5,620,463 | A | 4/1997 | Drolet | |
| 5,691,325 | A | 11/1997 | Sandyk | |
| 5,778,894 | A | 7/1998 | Dorogi et al. | |
| 6,413,255 | B1 | 7/2002 | Stern | |
| 6,453,202 | B1 | 9/2002 | Knowlton | |
| 6,500,110 | B1 | 12/2002 | Davey et al. | |
| 6,684,107 | B1 | 1/2004 | Binder | |
| 7,563,224 | B2 | 7/2009 | Puchek | |
| 8,696,686 | B2 | 4/2014 | Drews et al. | |
| 8,961,511 | B2 | 2/2015 | Parmer | |
| 8,998,791 | B2 | 4/2015 | Ron Edoute et al. | |
| 9,008,793 | B1 | 4/2015 | Cosman et al. | |
| 9,039,697 | B2 | 5/2015 | Lischinsky et al. | |
| 9,814,897 | B2 | 11/2017 | Ron Edoute et al. | |
| 9,981,143 | B2 | 5/2018 | Ron Edoute et al. | |
| 10,463,869 | B2 | 11/2019 | Ron Edoute et al. | |
| 2003/0216728 | A1 | 11/2003 | Stern et al. | |
| 2004/0034346 | A1 | 2/2004 | Stern et al. | |
| 2005/0182462 | A1 | 8/2005 | Chornenky et al. | |
| 2005/0187599 | A1 | 8/2005 | Sharkey et al. | |
| 2005/0283141 | A1 | 12/2005 | Giovannoli | |
| 2006/0173518 | A1 | 8/2006 | Kreindel | |
| 2006/0224148 | A1 | 10/2006 | Cho et al. | |
| 2006/0259102 | A1 | 11/2006 | Slatkine | |
| 2006/0293719 | A1 | 12/2006 | Naghavi | |
| 2007/0106306 | A1* | 5/2007 | Bodduluri | A61B 34/70 606/133 |
| 2007/0203447 | A1 | 8/2007 | Jun | |
| 2008/0008793 | A1 | 1/2008 | Forsyth et al. | |
| 2008/0058793 | A1 | 3/2008 | Pilla et al. | |
| 2008/0097530 | A1 | 4/2008 | Muccio et al. | |
| 2008/0097558 | A1 | 4/2008 | Eggers et al. | |
| 2008/0183251 | A1 | 7/2008 | Azar et al. | |
| 2008/0249350 | A1 | 10/2008 | Marchitto et al. | |
| 2008/0255543 | A1 | 10/2008 | Tanaka et al. | |
| 2008/0255642 | A1 | 10/2008 | Zarins et al. | |
| 2009/0270945 | A1 | 10/2009 | Markoll et al. | |
| 2011/0224693 | A1 | 9/2011 | Bodduluri et al. | |
| 2012/0022504 | A1 | 1/2012 | Epshtein et al. | |
| 2012/0041431 | A1 | 2/2012 | Levin et al. | |
| 2012/0226214 | A1 | 9/2012 | Gurtner et al. | |
| 2013/0238062 | A1 | 9/2013 | Ron Edoute et al. | |
| 2013/0317282 | A1 | 11/2013 | Ron Edoute et al. | |
| 2013/0317580 | A1 | 11/2013 | Simon et al. | |
| 2014/0200564 | A1 | 7/2014 | Schomacker et al. | |
| 2016/0192961 | A1* | 7/2016 | Ginggen | A61B 17/3203 604/173 |
| 2016/0346561 | A1* | 12/2016 | Ron Edoute | A61N 1/328 |
| 2017/0173360 | A1 | 6/2017 | O'Neil et al. | |
| 2018/0353772 | A1 | 12/2018 | Chen et al. | |
| 2018/0361137 | A1 | 12/2018 | Kern et al. | |
| 2019/0366067 | A1 | 12/2019 | Ginggen et al. | |
| 2020/0038051 | A1* | 2/2020 | Austen | A61B 17/205 |
| 2020/0188184 | A1* | 6/2020 | Levinson | A61F 13/0246 |
| 2020/0306554 | A1 | 10/2020 | Ron Edoute et al. | |
| 2021/0146119 | A1 | 5/2021 | Schwarz | |

FOREIGN PATENT DOCUMENTS

| | | | |
|---|---|---|---|
| CN | 103301567 | A | 9/2013 |
| CN | 104013466 | A | 9/2014 |
| DE | 3340974 | A1 | 5/1985 |
| DE | 3825165 | A1 | 1/1990 |
| EP | 2564894 | A1 | 3/2013 |
| GB | 0304587 | | 3/1930 |
| GB | 2188238 | A | 9/1987 |
| JP | 2009-509671 | A | 3/2009 |
| JP | 2014-507990 | A | 4/2014 |
| JP | 2014-514007 | A | 6/2014 |
| JP | 2016-529000 | A | 9/2016 |
| WO | WO-93/12835 | A1 | 7/1993 |
| WO | WO-93/12839 | A1 | 7/1993 |
| WO | WO-98/05380 | | 2/1998 |
| WO | WO-00/53113 | A1 | 9/2000 |
| WO | WO-2004/096343 | A2 | 11/2004 |
| WO | WO-2008/064272 | A2 | 5/2008 |
| WO | WO-2008/068749 | | 6/2008 |
| WO | WO-2009/047628 | A2 | 4/2009 |
| WO | WO-2010/007614 | A2 | 1/2010 |
| WO | WO-2011/034986 | A2 | 3/2011 |

OTHER PUBLICATIONS

Ahmadian et al., "Effects of extremely-low frequency pulsed electromagnetic fields on collagen synthesis in rat skin", Biotechnology

(56) References Cited

OTHER PUBLICATIONS and Applied Biochemistry, International Union of Biochemistry and Molecular Biology, 2006, vol. 43, No. 2, pp. 71-75.
Rosch et al., "Bioelectromagnetic medicine", Marcel Dekker, New York, NY, USA, 2004, pp. 251-264.
Tepper et al., "Electromagnetic fields increase in vitro and in vivo angiogenesis through endothelial release of FGF-2", The Laboratory of Microvascular Research and Vascular Tissue Engineering, New York University School of Medicine, New York, NY, USA, FASEB Journal, Aug. 2004, pp. 1231-1233.
Zelickson et al., "Histological and ultrastructural evaluation of the effects of a radiofrequency-based nonablative dermal remodeling device: a pilot study", Arch Dermatol, Department of Dermatology, University of Minnesota, Minneapolis, MN, USA, 2004, vol. 140, No. 2, pp. 204-209.
EP Search Report on EP 22772037.2 dtd Jan. 10, 2025.
Foreign Search Report on PCT/IB2022/056307 Dtd Oct. 27, 2022.
International Search Report and Written Opinion dated Sep. 23, 2022, PCT Application No. PCT/US2022/20338.

* cited by examiner

400 obtaining (i) pulsed electromagnetic frequency generator; and, (ii) a deep tissue diathermy device    401 applying heat to a subcutaneous tissue within said region up to temperature T    402

Applying pulsed electromagnetic therapy    403

410

Obtaining (i) pulsed electromagnetic frequency generator; and, (ii) a deep tissue diathermy device — 411

Applying pulsed electromagnetic therapy — 412

Applying heat to a subcutaneous tissue within said region up to temperature T — 413

Monitoring tissue parameters and controlling pulsed electromagnetic frequency generator (2) and deep tissue diathermy device (4) accordingly — 414

420

Obtaining (i) pulsed electromagnetic frequency generator; and, (ii) a deep tissue diathermy device — 421

Applying pulsed electromagnetic therapy whilst simultaneously applying heat to a subcutaneous tissue within said region up to temperature T — 422

420

Obtaining (i) pulsed electromagnetic frequency generator; and, (ii) a deep tissue diathermy device — 421

Applying pulsed electromagnetic therapy whilst simultaneously applying heat to a subcutaneous tissue within said region up to temperature T — 422

Monitoring tissue parameters and controlling pulsed electromagnetic frequency generator (2) and deep tissue diathermy device (4) accordingly — 423

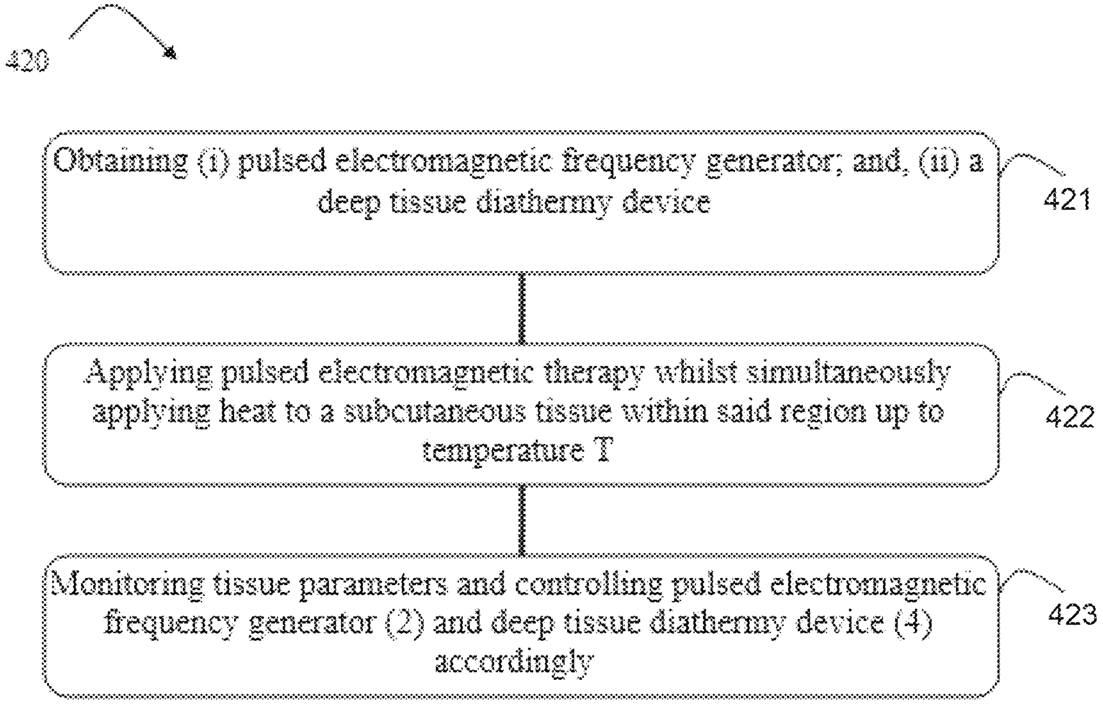

FIG. 12

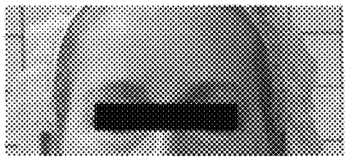
FIG. 13C1
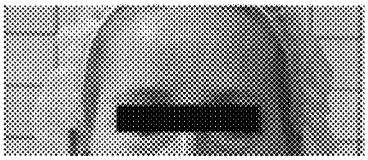
FIG. 13B1
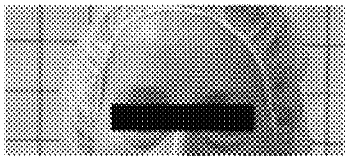
FIG. 13A1
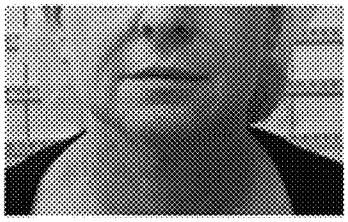
FIG. 13C2
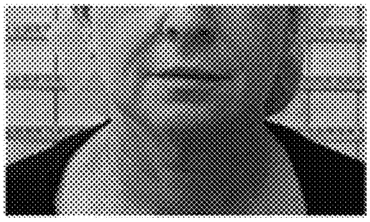
FIG. 13B2
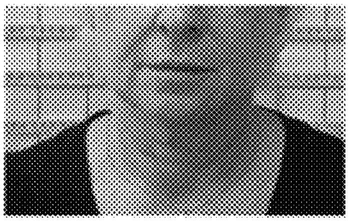
FIG. 13A2

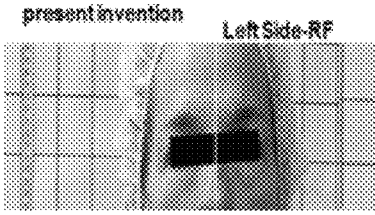
FIG. 14C1
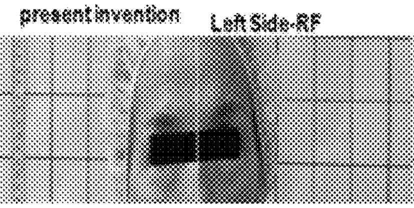
FIG. 14B1
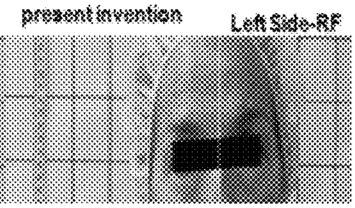
FIG. 14A1
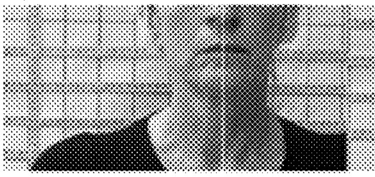
FIG. 14C2
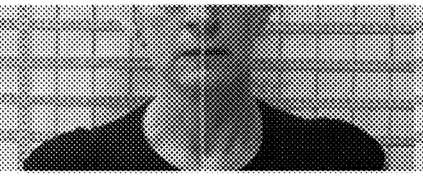
FIG. 14B2
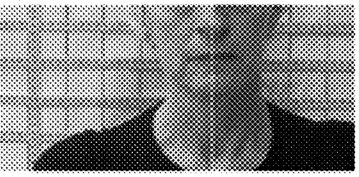
FIG. 14A2

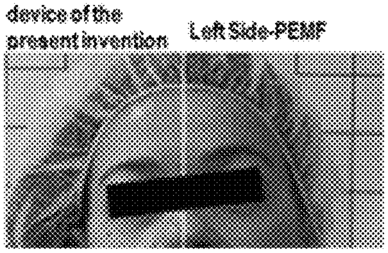
FIG. 15C1
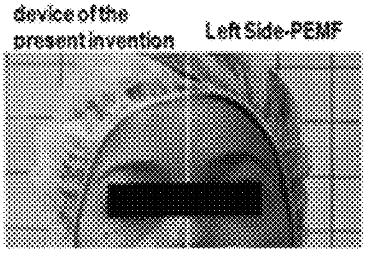
FIG. 15B1
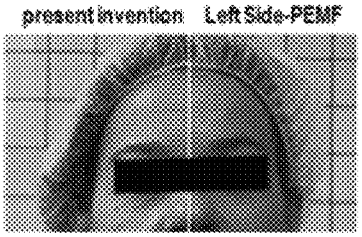
FIG. 15A1
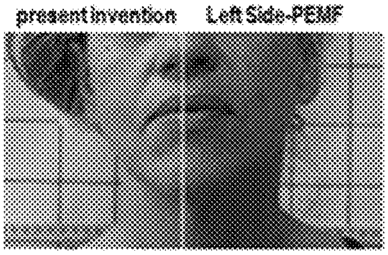
FIG. 15C2
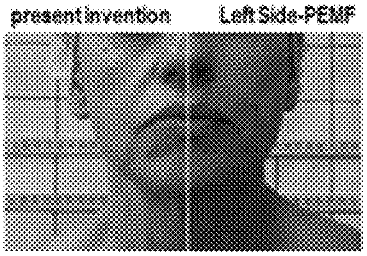
FIG. 15B2
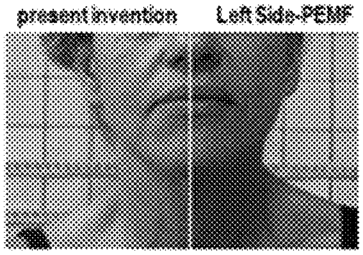
FIG. 15A2

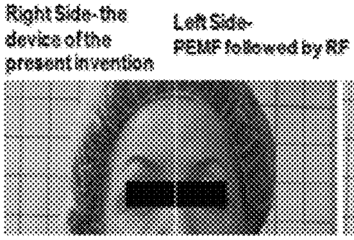
FIG. 16C1
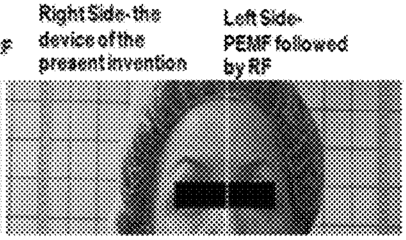
FIG. 16B1
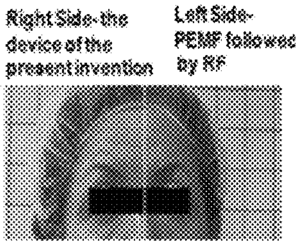
FIG. 16A1
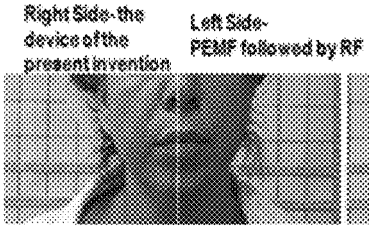
FIG. 16C2
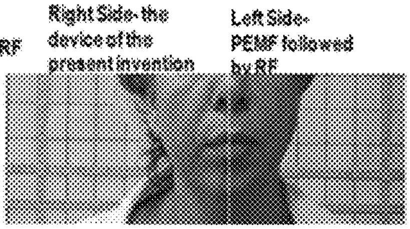
FIG. 16B2
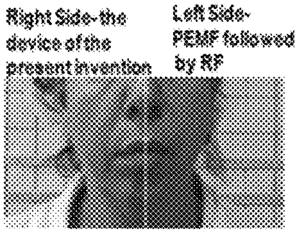
FIG. 16A2

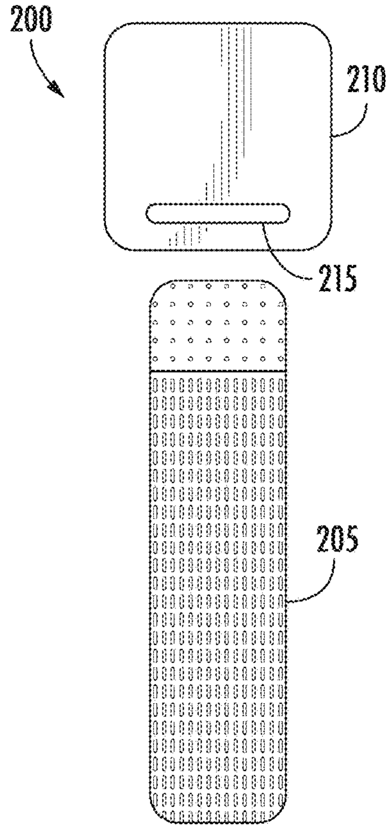
FIG. 26A1
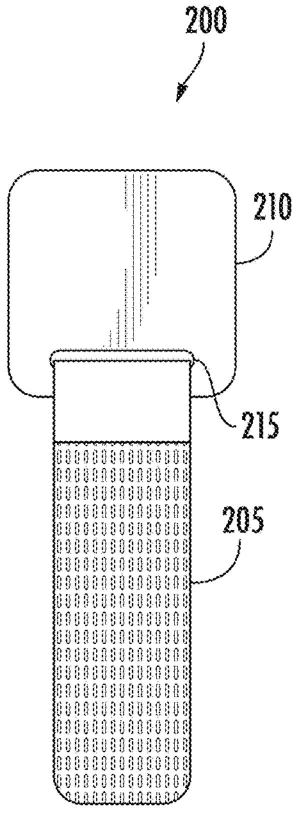
FIG. 26A2
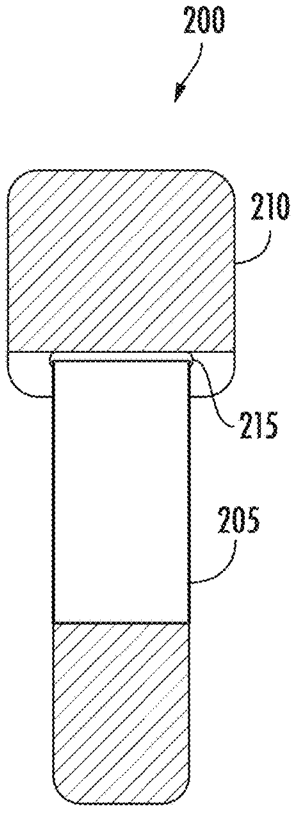
FIG. 26A3
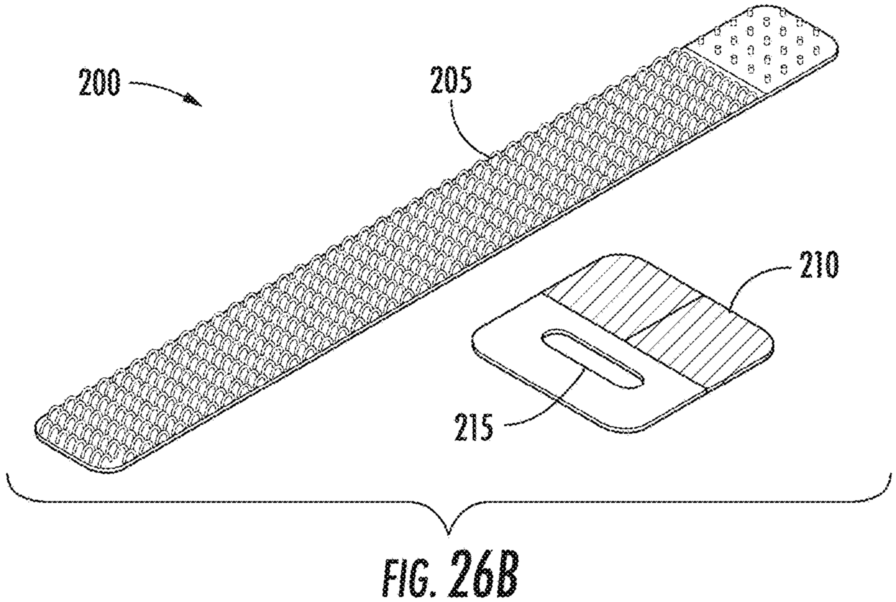
FIG. 26B

LONG PIECE'S COMPOSITION

HOOK SHEET WITH ADHESIVE ON BOTTOM SIDE

205

LOOP SHEET WITH ADHESIVE ON BOTTOM SIDE

BASE

SKIN CONTACT ADHESIVE

LINER (TO PROTECT ADHESIVE)

205

205

205

ESTHETIC APPARATUS USEFUL FOR INCREASING SKIN REJUVENATION AND METHODS THEREOF

CROSS-REFERENCE TO RELATED APPLICATIONS

The present application is a continuation-in-part of and claims the benefit of priority to U.S. application Ser. No. 16/864,862 filed May 1, 2020, which is a continuation of U.S. application Ser. No. 15/728,560 filed Oct. 10, 2017, now U.S. Pat. No. 10,661,093, issued May 6, 2020, which is a continuation of U.S. application Ser. No. 15/341,010 filed Nov. 2, 2016, now U.S. Pat. No. 9,901,743, issued Feb. 27, 2018, which is a continuation of U.S. application Ser. No. 14/845,315, filed Sep. 4, 2015, now U.S. Pat. No. 9,814,897, issued Nov. 14, 2017, which is a divisional of U.S. application Ser. No. 14/489,572, filed Sep. 18, 2014, now U.S. Pat. No. 9,694,194 issued on Jul. 4, 2017, which is a divisional of U.S. application Ser. No. 13/954,320, filed Jul. 30, 2013, now U.S. Pat. No. 8,979,727, issued on Mar. 17, 2015, which is a divisional of U.S. application Ser. No. 13/001,834, filed Feb. 1, 2011, now U.S. Pat. No. 8,998,791, issued on Apr. 7, 2015, which is a national phase entry of International Application No. PCT/IL2009/000644, filed Jun. 29, 2009, which claims priority from U.S. Provisional Application No. 61/112,783, filed on Nov. 10, 2008, and U.S. Provisional Application No. 61/076,652, filed on Jun. 29, 2008, the entire contents of all of which are incorporated herein by reference.

In addition, the present application claims the benefit of priority to U.S. Provisional Application No. 63/161,471 filed Mar. 16, 2021, the entire contents of which are incorporated herein by reference.

FIELD OF THE INVENTION

This invention generally relates to an esthetic device used to improve skin viability and skin rejuvenation, and a method of using the device.

BACKGROUND OF THE INVENTION

Improving the appearance of the skin has been the goal of many esthetic products and procedures for many years, since a tight skin, without wrinkles or cellulite, has a younger and more appealing appearance. Apart from age related changes, the skin also suffers from exposure to chemical and physical injuries, such as tobacco, cosmetics, esthetics and radiation from the sun and other sources. Those factors contribute to the decrease in collagen production, to reduced elasticity, and the appearance of wrinkles.

A few main approaches to tightening of the skin are common practice today. The surgical approach carries disadvantages related to the anesthesia, the surgical complications, and the healing process, which may cause scars. The chemical peel approach usually involves injury to the outermost layer of the skin—the epidermis—which may cause discoloration. Since collagen fibers are found in the dermis—the subcutaneous layer of the skin, and since heat was shown to contract these fibers and generate their production [Zelickson B D, Kist D, Bernstein E, Brown D B, Ksenzenko S, Burns J, Kilmer S, Mehregan D, Pope K. Histological and ultrastructural evaluation of the effects of a radiofrequency-based nonablative dermal remodeling device: a pilot study. Arch Dermatol. 2004 February; 140 (2):204-9], methods of differentially heating the dermis (deep tissue diathermy) have recently arisen.

A unique method of treating the dermis is called Pulsed Electromagnetic Fields (PEMF) therapy. This method usually employs electromagnetic radiation of different frequencies—ranging from static magnetic fields, through extremely low frequencies (ELF) to higher radiofrequencies (RF)—administered in pulses.

PEMF works in few ways. Due to the radiation absorbed in the tissue, it can be heated to various temperatures, depending on the power applied, the frequency transmitted, and more importantly the tissue characteristics. Eventually, the tissue can be warmed to denaturation temperatures, which cause coagulation necrosis and tissue damage. It can also be heated to lower temperatures, which proved to result in the afore-mentioned contraction of collagen fibers. It should be noted that of range of intensities used for tissue treatment, it is mostly the RF that cause heating whereas the PEMF is non thermal (and each with accordingly derived impacts).

Other modus operandi involve non thermal effects. These methods rely on specific tissue components and their reaction to the applied radiation characteristics. These effects might be due to large charged molecules and their reaction to various frequencies and frequency harmonies, charged small ions in the cell membranes affecting the cells function and reactions to hormones and chemical signals, charged small ions in the extracellular space and other poorly understood mechanisms.

Furthermore, applying the radiation in pulses was also found to have non thermal effects. Yet more, only a specific combination of frequency, duty cycle and transmitted power achieve a specific tissue response. Recent scientific research has confronted these challenges and found the PEMF characteristics needed for the desired biophysical response.

It is now commonly accepted that weak electromagnetic fields (EMF) administered in pulses are capable of initiating various healing processes in fractures, multiple sclerosis and Parkinson's disease, and even delivering pain relief (the non-thermal effects); however it seems that most of the conditions that seem most likely to respond to PEMF are musculoskeletal. The FDA has allowed the use of pulsed radiofrequency electromagnetic field for treatment of pain and edema in superficial soft tissues two decades ago. [Rosch, P. J., Markov, M. S., eds. Bioelectromagnetic Medicine, Marcel Dekker, NY, 251-264].

The use of PEMF can also be recruited for cosmetic purposes as described above. Several studies have addressed the effect of PEMF on dermal components. For example, in vivo trials showed that pulsed electromagnetic field of certain field intensities and frequencies increased epidermal collagen synthesis [Ahmadian S, Zarchi S R, Bolouri B. Effects of extremely-low-frequency pulsed electromagnetic fields on collagen synthesis in rat skin. Biotechnol Appl Biochem. 2006 February; 43(Pt 2):71-5]. This new formed collagen increases skin elasticity and rejuvenates the skin's appearance.

In vitro trials showed that PEMF increased the degree of endothelial cell tubulization and proliferation, and augmented angiogenesis primarily by stimulating endothelial release of FGF-2, inducing paracrine and autocrine changes in the surrounding tissue [Tepper O M et al. Electromagnetic fields increase in vitro and in vivo angiogenesis through endothelial release of FGF-2. FASEB J. 2004 August; 18(11):1231-3. Epub 2004 Jun. 18]. Angiogenesis, the sprouting of new blood vessels, increases blood flow to the tissue, which in turn increases oxygen and nutritional substances delivery to the tissue. This effect is most beneficial for an injured tissue, promoting rapid and improved healing. The growth factor released further enhances the healing process, both in quality and time of improvement.

The scientific evidence of the effect of PEMF on tissues was utilized in various applications. For example, US20050182462A1 discloses healthy deep tissue heating using PEMF for the purpose of causing contraction and tightening of the skin.

PEMF has also been used to improve skin wound healing. For example, WO08064272 discloses a method of treating a severe diabetic ulcer using PEMF, and also discloses the addition of intermittent compression therapy (ICT) and the use of low intensity ultrasound (up to 50 $W/cm^2$), the latter aimed at inhibiting microbial growth.

Other methods of heating the dermis used non pulsating RF radiation, applied by antenna or electrodes. For example, WO98005380 discloses a method of tightening skin using an RF electromagnetic energy delivery device.

Improving the results of skin tightening based on dermis diathermy is still a long felt need, both for esthetic and therapeutic purposes.

SUMMARY OF THE INVENTION

It is one object of the present invention to provide a system (10) adapted to increase skin rejuvenation of a region of a patient's skin, said system comprising a. a pulsed electromagnetic field (PEMF) frequency generator (2) for constantly providing electromagnetic pulses to said region of a patient's skin; and, b. a deep tissue diathermy device (4) for constantly applying heat to said region of a patient's skin up to temperature T;

said system (10) is adapted for simultaneously applying heat and PEMF to said region of a patient's skin; wherein application of said system increases said skin rejuvenation such that said skin rejuvenation increase (SRI) is greater than the sum of said SRI provided by electromagnetic pulses increase and said SRI provided by said deep tissue diathermy device increase.

It is another object of the present invention to provide the system as defined above, wherein said electromagnetic pulse is a triangular shaped at frequency of 25 Hz and intensity of 40 Gauss.

It is another object of the present invention to provide the system as defined above, wherein said electromagnetic pulse is square shaped at a frequency of 16 Hz, duration of about 5 milliseconds and intensity of 12 Gauss.

It is another object of the present invention to provide the system as defined above, wherein said deep tissue diathermy device (4) is selected from any device emitting RF radiation, any device adapted to deliver RF energy, any device adapted to conduct RF energy, or any means (e.g., a current generator) adapted for producing electrical current absorbed by subcutaneous tissue.

It is another object of the present invention to provide the system as defined above, wherein said deep tissue diathermy device (4) additionally comprises:

a. at least one electrical output device adapted to generate RF electromagnetic energy;

b. at least two electrodes electrically coupled to said electrical output device and placed on said skin region, wherein all said electrodes are adapted to simultaneously apply said RF energy to said skin region.

It is another object of the present invention to provide the system as defined above, wherein said deep tissue diathermy device (4) additionally comprises:

a. at least one electrical output device adapted to generate electrical current;

b. at least two electrodes electrically coupled to said electrical output device and placed on said skin region, wherein all said electrodes are adapted to simultaneously apply said electrical current to said skin region.

It is another object of the present invention to provide the system as defined above, wherein said system reduces side effects and/or harmful effects of said electromagnetic pulses and/or said deep tissue diathermy such that said reduction of said side effects and/or said harmful effects is greater than the sum of said reduction of said electromagnetic pulses and/or said reduction of said deep tissue diathermy.

It is another object of the present invention to provide the system as defined above, wherein said system additionally comprising a control system (6) adapted to regulate said electromagnetic pulses and/or said electromagnetic pulses.

It is another object of the present invention to provide the system as defined above, wherein said pulsed electromagnetic frequency generator is adapted to provide a dynamic magnetic field such that said electromagnetic pulses vary with time.

It is another object of the present invention to provide the system as defined above, wherein the shape of said electromagnetic pulse is selected in a non-limiting manner from a group consisting of square wave, a sine wave, a triangular wave, sawtooth wave, ramp waves, spiked wave or any other mathematical combination.

It is another object of the present invention to provide the system as defined above, wherein the magnetic field intensity B of each pulse applied by said pulsed electromagnetic frequency generator (2) ranges between about 0 and about 3 Tesla.

It is another object of the present invention to provide the system as defined above, wherein the duration of each pulse applied by said pulsed electromagnetic frequency generator (2) ranges between about 3 and about 1000 milliseconds.

It is another object of the present invention to provide the system as defined above, wherein the frequency F applied by the pulses of said pulsed electromagnetic frequency generator (2) ranges between about 1 Hz and about 1 MHz.

It is another object of the present invention to provide the system as defined above, wherein the energy E applied by the pulses of said pulsed electromagnetic frequency generator (2) ranges between about 1 and about 150 watts per pulse.

It is another object of the present invention to provide the system as defined above, wherein said deep tissue diathermy device (4) is selected in a non-limiting manner from a group consisting of an ultrasonic diathermy, an optical device, electromagnetic induction, sound waves emitting instrument, direct heat applying instrument, or from any other means of heating (e.g. a heater) subcutaneous tissue to temperature T.

It is another object of the present invention to provide the system as defined above, wherein said optical device is adapted to emit light in wavelengths absorbed by subcutaneous tissue such that said subcutaneous tissue is heated.

It is another object of the present invention to provide the system as defined above, wherein said sound waves emitting instrument is adapted to emit sound waves absorbed by the subcutaneous tissue such that said subcutaneous tissue is heated.

It is another object of the present invention to provide the system as defined above, wherein said temperature T is higher than about 30 and lower than about 100 degrees.

It is another object of the present invention to provide the system as defined above, wherein said power supply and control system (6) monitors physical tissue parameters and changes applied heat and electromagnetic pulses accordingly.

It is another object of the present invention to provide the system as defined above, wherein said power supply and control system (6) additionally comprising:

a. processing means (e.g. a processor), adapted to store in a communicable database predetermined parameters defining (i) safe treatment parameters and (ii) unsafe treatment parameters; said parameters are selected from a group consisting of time t of said treatment, temperature T of said tissue, ratio t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;

b. sensing means (e.g. a sensor); adapted to sense electromagnetic radiation and heat radiation parameters selected from a group consisting of time t of time t of said treatment, temperature T of said tissue, ratio t/T, Frequency F, power P, Intensity I of said ultrasound irradiation, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof, c. regulating means (e.g., a regulator, a controller), adapted to allow said electromagnetic radiation and heat radiation if said parameters are within said safe treatment parameters and to stop the electromagnetic radiation if the radiation parameters are in said unsafe treatment parameters.

It is another object of the present invention to provide the system as defined above, wherein said power supply and control system (6) includes a mechanism for skin cooling (e.g. a cooler).

It is another object of the present invention to provide the system as defined above, wherein said system (10) is encased in at least one platform.

It is another object of the present invention to provide the system as defined above, wherein said pulsed electromagnetic frequency generator (2) and said deep tissue diathermy device (4) have more than one applicator to treat more than one body part simultaneously.

It is another object of the present invention to provide the system as defined above, wherein said pulsed electromagnetic frequency generator (2) has electrostatic shielding.

It is another object of the present invention to provide the system as defined above, especially adapted to increase skin rejuvenation in the immediate (short) range.

It is another object of the present invention to provide the system as defined above, especially adapted to increase skin rejuvenation in the intermediate range.

It is another object of the present invention to provide the system as defined above, especially adapted to increase skin rejuvenation in the long range.

It is another object of the present invention to provide the system as defined above, wherein said system is especially adapted to operate according to IEC selected from a group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 or any combination thereof.

It is another object of the present invention to provide a method (400) of increasing skin rejuvenation of a region of a patient's skin. The method comprises steps selected inter alia from:

a. obtaining (i) pulsed electromagnetic frequency generator; and, (ii) a deep tissue diathermy device;

b. applying heat to a subcutaneous tissue within said region up to temperature T; and, c. applying pulses of electromagnetic field to said region;

wherein said increasing of said skin rejuvenation is greater than the sum of said applying heat to a subcutaneous tissue within said region increase and said applying pulses electromagnetic therapy to said region increase.

It is another object of the present invention to provide a method (410) of increasing skin rejuvenation of a region of a patient's skin. The method comprises steps selected inter alia from:

a. obtaining (i) pulsed electromagnetic frequency generator; and, (ii) a deep tissue diathermy device;

b. applying pulses of electromagnetic field to said region; and, c. applying heat to a subcutaneous tissue within said region up to temperature T;

wherein said increasing of said skin rejuvenation is greater than the sum of said applying heat to a subcutaneous tissue within said region and said applying pulses electromagnetic therapy to said region It is another object of the present invention to provide a method (420) of increasing skin rejuvenation of a region of a patient's skin. The method comprises steps selected inter alia from:

a. obtaining (i) pulsed electromagnetic frequency generator; and, (ii) a deep tissue diathermy device;

b. applying heat to a subcutaneous tissue within said region up to temperature T; whilst simultaneously applying pulses of electromagnetic field to said region;

wherein said increasing of said skin rejuvenation is greater than the sum of said applying heat to a subcutaneous tissue within said region and said applying pulses electromagnetic therapy to said region.

It is another object of the present invention to provide the methods as defined above, wherein said system reduces side effects and/or harmful effects of said electromagnetic pulses and/or said deep tissue diathermy such that said reduction of said side effects and/or said harmful effects is greater than the sum of said reduction of said electromagnetic pulses and/or said reduction of said deep tissue diathermy.

It is another object of the present invention to provide the methods as defined above, additionally comprising step of monitoring and/or controlling said steps of applying heat to a subcutaneous tissue within said region and/or said step of applying pulsed electromagnetic therapy to said region.

It is another object of the present invention to provide the methods as defined above, additionally comprising step of applying a dynamic magnetic field onto said region.

It is another object of the present invention to provide the methods as defined above, additionally comprising steps of a. storing in a communicable database predetermined parameters defining (i) safe treatment parameters and (ii) unsafe treatment parameters; said parameters are selected from a group consisting of time t of said treatment, temperature T of said tissue, ratio t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;

b. sensing electromagnetic radiation and heat radiation parameters selected from a group consisting of time t of said treatment, temperature T of said tissue, ratio t/T, Frequency F, power P, Intensity I of said ultrasound irradiation, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;

c. allowing said electromagnetic radiation and said heat radiation if parameters within said safe treatment parameters and to stop the electromagnetic radiation if the radiation parameters are in said unsafe treatment parameters.

It is another object of the present invention to provide the methods as defined above, additionally comprising step of selecting the shape of said electromagnetic pulse is selected in a non-limiting manner from a group consisting of square wave, a sine wave, a triangular wave, sawtooth wave, ramp waves, spiked wave or any other mathematical combination.

It is another object of the present invention to provide the methods as defined above, additionally comprising step of applying a triangular shaped electromagnetic pulse at frequency of 25 Hz and intensity of 40 Gauss.

It is another object of the present invention to provide the methods as defined above, additionally comprising step of applying a square shaped electromagnetic pulse at a frequency of 16 Hz, duration of about 5 milliseconds and intensity of 12 Gauss.

It is another object of the present invention to provide the methods as defined above, additionally comprising step of selecting said deep tissue diathermy device (4) from any device emitting RF radiation, any device adapted to deliver RF energy, any device adapted to conduct RF energy, or any means (e.g., a current supply) adapted for producing electrical current absorbed by subcutaneous tissue.

It is another object of the present invention to provide the methods as defined above, wherein said step of applying heat to a subcutaneous tissue additionally comprising steps of a. obtaining at least one electrical output device adapted to generate RF electromagnetic energy;
b. electrically coupling at least two electrodes to said electrical output device;
c. placing said at least two electrodes on said skin region; and,
d. simultaneously applying via all said electrodes said RF energy to said skin region.

It is another object of the present invention to provide the methods as defined above, wherein said step of applying heat to a subcutaneous tissue additionally comprising steps of a. obtaining at least one at least one electrical output device adapted to generate electrical current;
a. electrically coupling at least two electrodes to said electrical output device;
b. placing said at least two electrodes on said skin region; and,
c. simultaneously applying via all said electrodes said electrical current to said skin region.

It is another object of the present invention to provide the methods as defined above, additionally comprising step of selecting said temperature T from a region of about 30 to about 100 degrees.

It is another object of the present invention to provide the methods as defined above, additionally comprising step of selecting the duration of each pulse applied by said pulsed electromagnetic frequency generator (2) to be higher than about 3 and lower than about 1000 milliseconds.

It is another object of the present invention to provide the methods as defined above, additionally comprising step of selecting the magnetic field intensity B of each pulse applied by said step of applying pulsed electromagnetic therapy to said region to be higher than about 0 and lower than about max magnetic field used in MRI devices (i.e., 3 Tesla).

It is another object of the present invention to provide the methods as defined above, additionally comprising step of selecting the frequency F applied by the pulses applied by said step of applying pulsed electromagnetic therapy to said region to be higher than about 1 and lower than about 1 MHz.

It is another object of the present invention to provide the methods as defined above, additionally comprising step of selecting the energy E applied by said step of applying pulsed electromagnetic therapy to said region to be higher than about 1 and lower than about 150 watts per pulse.

It is another object of the present invention to provide the methods as defined above, wherein step of applying heat is applied for about 0.01 to 60 minutes.

It is another object of the present invention to provide the methods as defined above, wherein the heat and the pulsed electromagnetic therapy are applied simultaneously, sequentially or separately.

It is another object of the present invention to provide the methods as defined above, wherein said method is repeated 1 to 100 times in each treatment.

It is another object of the present invention to provide the methods as defined above, wherein said treatment is repeated more than once.

It is another object of the present invention to provide the methods as defined above, wherein said step of applying heat is performed by devices selected from a group consisting of: ultrasonic diathermy, an optical device, electromagnetic induction, sound waves emitting instrument, direct heat applying instrument, or from any other means of heating subcutaneous tissue to temperature T.

It is another object of the present invention to provide the methods as defined above, especially adapted to increase skin rejuvenation in the immediate (short) range It is another object of the present invention to provide the methods as defined above, especially adapted to increase skin rejuvenation in the intermediate range.

It is another object of the present invention to provide the methods as defined above, especially adapted to increase skin rejuvenation in the long range.

It is another object of the present invention to provide the methods as defined above, wherein said method is especially adapted to operate according to IEC selected from a group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 or any combination thereof.

It is another object of the present invention to provide an integrated system (20) adapted to increase skin rejuvenation of a region of a patient's skin, said system comprising at least two electrodes (41) adapted to be placed on said region of a patient's skin; each of said electrodes is at least partially coiled via a coil 42; wherein each of said electrodes is adapted for both (i) providing electromagnetic pulses to said region of a patient's skin; and, (ii) applying heat up to temperature T to said region of a patient's skin; further wherein all of said electrodes are adapted to simultaneously provide said electromagnetic pulses to said region of a patient's skin and apply heat to said region of a patient's skin.

It is another object of the present invention to provide the integrated system as defined above, wherein said heat applied to said region of a patient's skin is obtained by emitting RF radiation, any device adapted to deliver RF energy, any device adapted to conduct RF energy, or via producing electrical current absorbed by subcutaneous tissue.

It is another object of the present invention to provide the integrated system as defined above, wherein application of said system increases said skin rejuvenation such that said skin rejuvenation increase (SRI) is greater than the sum of said SRI provided by electromagnetic pulses increase and said SRI provided by said deep tissue diathermy device increase.

It is another object of the present invention to provide the integrated system as defined above, wherein said electromagnetic pulse is a triangular shaped at frequency of 25 Hz and intensity of 40 Gauss.

It is another object of the present invention to provide the integrated system as defined above, wherein said electromagnetic pulse is square shaped at a frequency of 16 Hz, duration of about 5 milliseconds and intensity of 12 Gauss.

It is another object of the present invention to provide the integrated system as defined above, wherein said system reduces side effects and/or harmful effects of said electromagnetic pulses and/or said deep tissue diathermy such that said reduction of said side effects and/or said harmful effects is greater than the sum of said reduction of said electromagnetic pulses and/or said reduction of said deep tissue diathermy.

It is another object of the present invention to provide the integrated system as defined above, wherein said system additionally comprising a control system (6) adapted to regulate said electromagnetic pulses and/or said electromagnetic pulses.

It is another object of the present invention to provide the integrated system as defined above, wherein said system is adapted to provide a dynamic magnetic field such that said electromagnetic pulses vary with time.

It is another object of the present invention to provide the integrated system as defined above, wherein the shape of said electromagnetic pulse is selected in a non-limiting manner from a group consisting of square wave, a sine wave, a triangular wave, sawtooth wave, ramp waves, spiked wave or any other mathematical combination.

It is another object of the present invention to provide the integrated system as defined above, wherein the magnetic field intensity B of each pulse applied by said pulsed electromagnetic frequency generator (2) ranges between about 0 and about 3 Tesla.

It is another object of the present invention to provide the integrated system as defined above, wherein the duration of each pulse applied by said system ranges between about 3 and about 1000 milliseconds.

It is another object of the present invention to provide the integrated system as defined above, wherein the frequency F applied by the pulses of said system ranges between about 1 Hz and about 1 MHz.

It is another object of the present invention to provide the integrated system as defined above, wherein the energy E applied by the pulses of said system ranges between about 1 and about 150 watts per pulse.

It is another object of the present invention to provide the integrated system as defined above, wherein said temperature T is higher than about 30 and lower than about 100 degrees.

It is another object of the present invention to provide the integrated system as defined above, wherein said power supply and control system (6) monitors physical tissue parameters and changes applied heat and electromagnetic pulses accordingly.

It is another object of the present invention to provide the integrated system as defined above, wherein said power supply and control system (6) additionally comprising:

a. processing means, adapted to store in a communicable database predetermined parameters defining (i) safe treatment parameters and (ii) unsafe treatment parameters; said parameters are selected from a group consisting of time t of said treatment, temperature T of said tissue, ratio t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;

b. sensing means; adapted to sense electromagnetic radiation and heat radiation parameters selected from a group consisting of time t of time t of said treatment, temperature T of said tissue, ratio t/T, Frequency F, power P, Intensity I of said ultrasound irradiation, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof, c. regulating means, adapted to allow said electromagnetic radiation and heat radiation if said parameters are within said safe treatment parameters and to stop the electromagnetic radiation if the radiation parameters are in said unsafe treatment parameters.

It is another object of the present invention to provide the integrated system as defined above, wherein said power supply and control system (6) includes a mechanism for skin cooling.

It is another object of the present invention to provide the integrated system as defined above, especially adapted to increase skin rejuvenation in the immediate (short) range.

It is another object of the present invention to provide the integrated system as defined above, especially adapted to increase skin rejuvenation in the intermediate range.

It is another object of the present invention to provide the integrated system as defined above, especially adapted to increase skin rejuvenation in the long range.

It is another object of the present invention to provide the integrated system as defined above, wherein said system is especially adapted to operate according to IEC selected from a group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 or any combination thereof.

It is another object of the present invention to provide a method of increasing skin rejuvenation of a region of a patient's skin. The method comprises steps selected inter alia from:

a. obtaining an integrated system (20) adapted to increase skin rejuvenation; said integrated system (20) comprises: at least two electrodes (41) adapted to be placed on said region of a patient's skin; each of said electrodes is a least partially coiled via a coil 42;
b. applying heat to a subcutaneous tissue within said region up to temperature T whilst simultaneously applying pulses of electromagnetic field to said region;

wherein said increasing of said skin rejuvenation is greater than the sum of said applying heat to a subcutaneous tissue within said region and said applying pulses electromagnetic therapy to said region.

It is another object of the present invention to provide the method as defined above, wherein said step of applying heat to a subcutaneous tissue within said region up to temperature T additionally comprising step of applying electrical current absorbed by subcutaneous tissue. It is another object of the present invention to provide the method as defined above, wherein said system reduces side effects and/or harmful effects of said electromagnetic pulses and/or said deep tissue diathermy such that said reduction of said side effects and/or said harmful effects is greater than the sum of said reduction of said electromagnetic pulses and/or said reduction of said deep tissue diathermy.

It is another object of the present invention to provide the method as defined above, additionally comprising step of monitoring and/or controlling said steps of applying heat to a subcutaneous tissue within said region and/or said step of applying pulsed electromagnetic therapy to said region.

It is another object of the present invention to provide the method as defined above, additionally comprising step of applying a dynamic magnetic field onto said region.

It is another object of the present invention to provide the method as defined above, additionally comprising step of applying a triangular shaped electromagnetic pulse at frequency of 25 Hz and intensity of 40 Gauss.

It is another object of the present invention to provide the method as defined above, additionally comprising step of applying a square shaped electromagnetic pulse at a frequency of 16 Hz, duration of about 5 milliseconds and intensity of 12 Gauss.

It is another object of the present invention to provide the method as defined above, additionally comprising steps of a. storing in a communicable database predetermined parameters defining (i) safe treatment parameters and (ii) unsafe treatment parameters; said parameters are selected from a group consisting of time t of said treatment, temperature T of said tissue, ratio t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
b. sensing electromagnetic radiation and heat radiation parameters selected from a group consisting of time t of said treatment, temperature T of said tissue, ratio t/T, Frequency F, power P, Intensity I of said ultrasound irradiation, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
c. allowing said electromagnetic radiation and said heat radiation if parameters within said safe treatment parameters and to stop the electromagnetic radiation if the radiation parameters are in said unsafe treatment parameters.

It is another object of the present invention to provide the method as defined above, additionally comprising step of selecting the shape of said electromagnetic pulse is selected in a non-limiting manner from a group consisting of square wave, a sine wave, a triangular wave, sawtooth wave, ramp waves, spiked wave or any other mathematical combination.

It is another object of the present invention to provide the method as defined above, additionally comprising step of selecting said temperature T from a region of about 30 to about 100 degrees.

It is another object of the present invention to provide the method as defined above, additionally comprising step of selecting the duration of each pulse applied by said pulsed electromagnetic frequency generator (2) to be higher than about 3 and lower than about 1000 milliseconds.

It is another object of the present invention to provide the method as defined above, additionally comprising step of selecting the magnetic field intensity B of each pulse applied by said step of applying pulsed electromagnetic therapy to said region to be higher than about 0 and lower than about 3 Tesla.

It is another object of the present invention to provide the method as defined above, additionally comprising step of selecting the frequency F applied by the pulses applied by said step of applying pulsed electromagnetic therapy to said region to be higher than about 1 and lower than about 1 MHz.

It is another object of the present invention to provide the method as defined above, additionally comprising step of selecting the energy E applied by said step of applying pulsed electromagnetic therapy to said region to be higher than about 1 and lower than about 150 watts per pulse.

It is another object of the present invention to provide the method as defined above, wherein step of applying heat is applied for about 0.01 to 60 minutes.

It is another object of the present invention to provide the method as defined above, wherein the heat and the pulsed electromagnetic therapy are applied simultaneously, sequentially or separately.

It is another object of the present invention to provide the method as defined above, wherein said method is repeated 1 to 100 times in each treatment.

It is another object of the present invention to provide the method as defined above, wherein said treatment is repeated more than once.

It is another object of the present invention to provide the method as defined above, wherein said step of applying heat is performed by devices selected from a group consisting of: ultrasonic diathermy, an optical device, electromagnetic induction, sound waves emitting instrument, direct heat applying instrument, or from any other means of heating subcutaneous tissue to temperature T.

It is another object of the present invention to provide the method as defined above, especially adapted to increase skin rejuvenation in the immediate (short) range.

It is another object of the present invention to provide the method as defined above, especially adapted to increase skin rejuvenation in the intermediate range.

It is still an object of the present invention to provide the method as defined above, especially adapted to increase skin rejuvenation in the long range.

It is lastly an object of the present invention to provide the method as defined above, wherein said method is especially adapted to operate according to IEC selected from a group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 or any combination thereof.

BRIEF DESCRIPTION OF THE DRAWINGS

In order to understand the invention and to see how it may be implemented in practice, a few preferred embodiments will now be described, by way of non-limiting example only, with reference to the accompanying drawings, in which:

FIGS. 7, 8, 9, 10, 11 and 12 are schematic representations of methods of improving skin viability (400-420).

FIGS. 13A1, 13B1, 13C1, 13A2, 13B2, and 13C2 are pictures of one patient out of the study group treated with the device of the present invention.

FIGS. 14A1, 14B1, 14C1, 14A2, 14B2 and 14C2 are pictures of one patient out of the first control group treated with the device of the present invention on the right side and RF on the left side.

FIGS. 15A1, 15B1, 15C1, 15A2, 15B2 and 15C2 are pictures of one patient out of the second control group treated with the device of the present invention on the right side and PEMF on the left side.

FIGS. 16A1, 16B1, 16C1, 16A2, 16B2 and 16C2 are pictures of one patient out of the third control group treated with the device of the present invention on the right side. The left side was treated with PEMF followed by RF.

FIG. 22 depicts a coaxial punch.

FIGS. 26A-26B illustrate one embodiment of the stretching/compression device, where FIG. 26A1 shows a top view of the device in an unassembled state, FIG. 26A2 shows a top view of the device in an assembled state, FIG. 26A3 shows a bottom view of the device in an assembled state, and FIG. 26B shows an exploded perspective view of the device.

FIGS. 27-28 illustrate the short side according to this embodiment of the stretching/compression device, where

FIGS. 29-30 illustrate the long side, according to this embodiment, of the stretching/compression device, where

DETAILED DESCRIPTION OF THE DRAWINGS

Figure 1A:
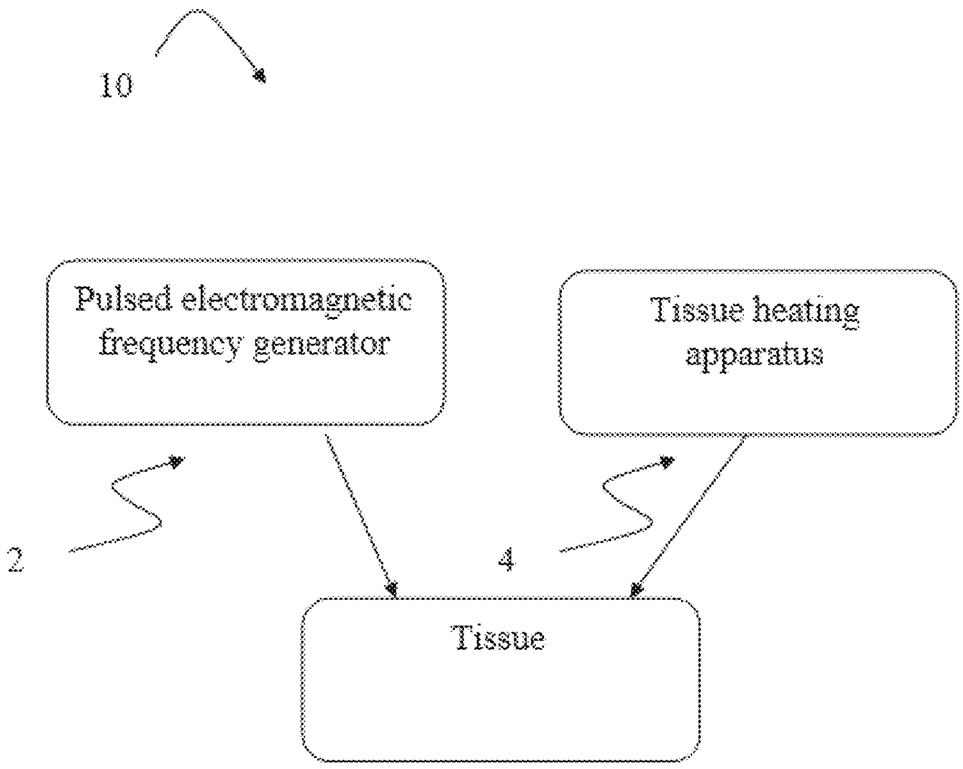
FIGS. 1A, 1B, 1C and 1D are schematic representations of a skin viability improving system (10), comprising a pulsed electromagnetic frequency generator (2) and a deep tissue diathermy device (4).

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide means and method for increasing the viability of the skin. Yet more the present invention provides means and system for skin tightening and rejuvenation.

It is one object of the present invention to disclose a device used to improve skin viability, by a synergistic approach of deep tissue diathermy combined with application of PEMF, wherein at least two devices of deep tissue diathermy are incorporated, one of them based on PEMF therapy. The latter improves the healing process initiated by the at least one other device of deep tissue diathermy.

The term "Pulsed Electromagnetic Fields (PEMF)" refers hereinafter in a non-limiting manner to electromagnetic radiation of different frequencies—ranging from static magnetic fields, through extremely low frequencies (ELF) to radiofrequencies (RF)—administered in pulses.

The term "Radio Frequency (RF)" refers hereinafter in a non-limiting manner to part of the electromagnetic spectrum with frequency range of about 3 Hz to 300 GHz.

The term "Extremely Low Frequencies (ELF)" refers hereinafter in a non-limiting manner to part of the RF electromagnetic spectrum with frequency range of about 3 Hz to 30 GHz The term "collagen" refers hereinafter in a non-limiting manner to a long, fibrous structural protein which is a major component of the extracellular matrix that supports most tissues and gives cells structure. It is responsible for skin strength and elasticity, and its degradation leads to wrinkles that accompany aging.

The term "epidermis" refers hereinafter in a non-limiting manner to the outermost layer of the skin.

The term "dermis" refers hereinafter in a non-limiting manner to a layer of skin beneath the epidermis that consists of connective tissue, and cushions the body from stress and strain.

The term "deep tissue diathermy" refers hereinafter in a non-limiting manner to a device which heats tissues beneath the epidermis.

The term "electric diathermy" refers hereinafter in a non-limiting manner to a device which uses high frequency alternating electric or magnetic fields, sometimes with no electrode or device contact to the skin, to induce gentle deep tissue heating by induction. For collagen fiber stimulation, typical electrical parameters may include, in a non limiting manner, frequency of about 1 MHz, energy of about 80 joule per 1 square tissue volume, applied for about 6 seconds.

The term "ultrasonic diathermy" refers hereinafter in a non-limiting manner to heating of tissues by ultrasound.

The term "about" refers hereinafter to a range of 25% below or above the referred value.

The term "physical tissue parameters" refers hereinafter to parameters such as tissue temperature, electric current, tissue impedance, specific absorption rate (SAR), treatment depth and superficial muscle contractions.

The term "angiogenesis" refers hereinafter to the sprouting of new blood vessels.

The term "square wave" refers hereinafter to a non-sinusoidal waveform named for its triangular shape.

The term "triangle wave" refers hereinafter to a non-sinusoidal waveform named for its triangular shape.

The term "International Electrotechnical Commission Standards (IEC) 60601-1" refers hereinafter to a medical electrical equipment standard. More specifically it refers to general requirements for basic safety and essential performance.

The term "IEC 60601-1-1" refers hereinafter to medical electrical equipment t; More specifically it refers to general requirements for safety—Collateral standard: Safety requirements for medical electrical systems. The IEC 60601-1 set of standards are divided into three distinct areas. The first area is the basic standard IEC 60601-1. This is the general requirement for all electrical medical based products. The second area is the collateral standards, which cover across the board issues such as combining into a system with other devices, EMC, radiation protection, and programmable electronic medical systems (software, firmware, etc.). The standard numbers are IEC 60601-1-1, -1-2, -1-3, and -1-4 respectively. The third area is the particular standards that deal with a specific type of medical device. The particular standards are identified as IEC 60601-2-XX where XX identifies the particular standard number for the particular type of medical equipment. An example would be IEC 60601-2-3 which is the particular standard for short-wave therapy equipment.

The term "IEC 60601-1-2" refers hereinafter to medical electrical equipment standard. More specifically it refers to general requirements for basic safety and essential performance—Collateral standard: Electromagnetic compatibility—Requirements and tests.

The term "IEC 60601-1-3" refers hereinafter to medical electrical equipment standard. More specifically it refers to general requirements for basic safety and essential performance—Collateral Standard: Radiation protection in diagnostic X-ray equipment.

The term "IEC 60601-1-4" refers hereinafter to medical electrical equipment standard. More specifically it refers to general requirements for safety—Collateral Standard: Programmable electrical medical systems.

The term "IEC 60601-1-6" refers hereinafter to medical electrical equipment standard. More specifically it refers to general requirements for basic safety and essential performance—Collateral standard: Usability.

The term "IEC 60601-1-8" refers hereinafter to medical electrical equipment standard. More specifically it refers to general requirements for basic safety and essential performance—Collateral Standard: General requirements, tests and guidance for alarm systems in medical electrical equipment and medical electrical systems.

The term "IEC 60601-2-3" refers hereinafter to medical electrical equipment standard. More specifically it refers to particular requirements for the safety of short-wave therapy equipment.

The term "IEC 60601-2-5" refers hereinafter to medical electrical equipment standard.

More specifically it refers to particular requirements for the safety of ultrasonic physiotherapy equipment.

The term "IEC 60601-2-9" refers hereinafter to medical electrical equipment. More specifically it refers to particular requirements for the safety of patient contact dosemeters used in radiotherapy with electrically connected radiation detectors.

The term "IEC 60601-2-29" refers hereinafter to medical electrical equipment standard.

More specifically it refers to particular requirements for the basic safety and essential performance of radiotherapy simulators.

The term "IEC 60601-2-33" refers hereinafter to medical electrical equipment standard.

More specifically it refers to particular requirements for the safety of magnetic resonance equipment for medical diagnosis.

The term "IEC 60601-2-35" refers hereinafter to medical electrical equipment standard.

More specifically it refers to particular requirements for the safety of blankets, pads and mattresses intended for heating in medical use.

The present invention relates to a physical therapeutic methods and systems. In said systems a dynamic magnetic pulse and electromagnetic heating systems are incorporated together to accomplish a physical therapy, epically skin tightening and rejuvenation.

The present invention provides a system adapted to increase skin rejuvenation of a region of a patient's skin. The system comprising in a non-limiting manner the following:

a. a pulsed electromagnetic field (PEMF) frequency generator (2) for constantly providing electromagnetic pulses to said region of a patient's skin; and,
b. a deep tissue diathermy device (4) applying heat to said region of a patient's skin up to temperature T;

The system (10) is adapted for simultaneously apply heat and PEMF to said region of a patient's skin. Furthermore, the system increases the skin rejuvenation such that the increase is greater than the sum of the electromagnetic pulses increase and the deep tissue diathermy. Furthermore the system reduces side effects and/or harmful effects of the electromagnetic pulses and/or said deep tissue diathermy such that said reduction of said side effects and/or said harmful effects is greater than the sum of said reduction of said electromagnetic pulses and/or said reduction of said deep tissue diathermy.

It is another object of the present invention to provide an integrated system (20) adapted to increase skin rejuvenation of a region of a patient's skin. The system comprising at least two electrodes adapted to be placed on said region of a patient's skin; each of said electrodes is at least partially coiled via a coil. It is emphasized that each of said electrodes is adapted for both (i) providing electromagnetic pulses to said region of a patient's skin; and, (ii) applying heat up to temperature T to said region of a patient's skin. Furthermore, it is emphasized that all of said electrodes are adapted to simultaneously provide electromagnetic pulses to said region of a patient's skin; and, apply heat up to temperature T to said region of a patient's skin.

The decrease in the side effects of the deep tissue diathermy by the healing effect of the pulsed electromagnetic frequency therapy.

Reference is now made to FIGS. 1A-1D, which illustrates the system (10) for increasing skin rejuvenation. As described above, the system (10) comprises a pulsed electromagnetic frequency generator (2) for providing electromagnetic pulses to the region of a patient's skin; and, a deep tissue diathermy device (4) adapted to apply heat to the region of a patient's skin up to temperature T.

It is emphasized that the system (10) increases the skin rejuvenation such that the increase is greater than the sum of the electromagnetic pulses increase and the deep tissue diathermy.

By exposing the tissue (a region of a patient's skin) to the combination of regulated heat and a pulsed electromagnetic filed a synergic effect of improving skin rejuvenation is obtained.

The present invention relays on 2 effects, the thermal effect and the electromagnetic pulse effect:

The thermal effect includes heating the tissue such that when the tissue is heated to a sufficiently high temperature, tissue injury is produced. Furthermore, when heat is generated within the dermis, it usually causes contraction and thickening of collagen fibers. This results in an overall tightened and rejuvenated appearance of the skin.

Heat within the dermis creates a limited thermal injury. The body's natural response to this injury is to produce collagen at the site of the wound. This results in firmer, thicker, more youthful skin. Usually the skin is heated to temperatures below 60 degrees for short periods of time. The thermal effect i.e., can be produced by:

1. Optical means, e.g., at least one emitter—by emitting light in different wavelengths absorbed by subcutaneous tissue such that said tissue is heated; or
2. Electrical means, e.g., electronic circuitry and/or a current generator—by passing electrical current; or
3. Electromagnetic means, e.g., an electromagnetic energy emitter—by transmitting or inducting (electromagnetic induction) electromagnetic filed on the skin; or
4. Sound waves, e.g., via an acoustic emitter—specifically in the ultrasound frequencies; or
5. Physical means, e.g., a manual applicator or other applicator of pressure and/or heat—such as massage or applying a warm substance adjacent to the skin; or any combination thereof.

The electromagnetic pulses (either dynamic or static) may start natural healing processes which usually occur in response to an injury (especially, angiogenesis, and generation of new collagen fibers via the release of tissue growth factors).

Said electromagnetic field generates movements of charged molecules (ions) within the inter cellular fluids. This movement generates heat which may enhance the thermal effect discussed earlier.

It is acknowledged that healing is the process by which the cells in the body regenerate and repair to reduce the size of a damaged area. Healing incorporates both the removal of necrotic tissue (demolition), and the replacement of this tissue.

The replacement can happen in two ways:

1. by regeneration: the necrotic cells are replaced by the same tissue as was originally there.
2. by repair: injured tissue is replaced with scar tissue.

The Pulsed Electromagnetic Fields (PEMF) applied by the system (10), as described above, has no thermal effects. Said no thermal effects rely on the tissue components and their reaction to the applied radiation characteristics. These effects might be due to the reaction of large charged molecules and various frequencies and frequency harmonies, charged small ions in the cell membranes affecting the cells function and reactions to hormones and chemical signals, charged small ions in the extracellular space and other purely understood mechanisms.

Furthermore, applying the radiation in pulses was also found to have non thermal effects. Yet more, only a specific combination of frequency, duty cycle and transmitted power achieve a specific tissue response.

It is now commonly accepted that electromagnetic fields (EMF) or PEMF are capable of initiating various healing processes and for treatment of pain and edema in superficial soft tissues two decades ago. [Rosch, P. J., Markov, M. S., eds. Bioelectromagnetic Medicine, Marcel Dekker, NY, 251-264].

The present invention utilizes PEMF (combined with heat applying source) for cosmetic purposes as described above. The important role of PEMF in the specific field intensities and frequencies increases epidermal collagen synthesis. This new formed collagen increases skin elasticity and rejuvenates its appearance. Furthermore, PEMF increases the degree of endothelial cell tubulization and proliferation, and augmented angiogenesis primarily by stimulating endothelial release of FGF-2, inducing paracrine and autocrine changes in the surrounding tissue. Angiogenesis, the sprouting of new blood vessels, increases blood flow to the tissue, which in turn increases oxygen and nutritional substances delivery to the tissue. This effect is most beneficial for an injured tissue, promoting rapid and improved healing. The growth factor released further enhances the healing process, both in quality and time of improvement.

The following discloser is a more detailed description of the two combined effects.

As disclosed earlier, the present invention discloses a system 10 which incorporates both regulated heating means and electromagnetic pulses.

As described above, the heat can be produced by:

1. Optical means—by emitting light in different wavelengths absorbed by subcutaneous tissue such that said tissue is heated.
2. Electrical means—by passing electrical current.
3. Electromagnetic means—by transmitting or inducting (electromagnetic induction) electromagnetic filed on the skin.
4. Sound waves—specifically in the ultrasound frequencies.
5. Physical means—such as massage or applying a warm substance adjacent to the skin (e.g., a massager or applicator).

Figure 1B:
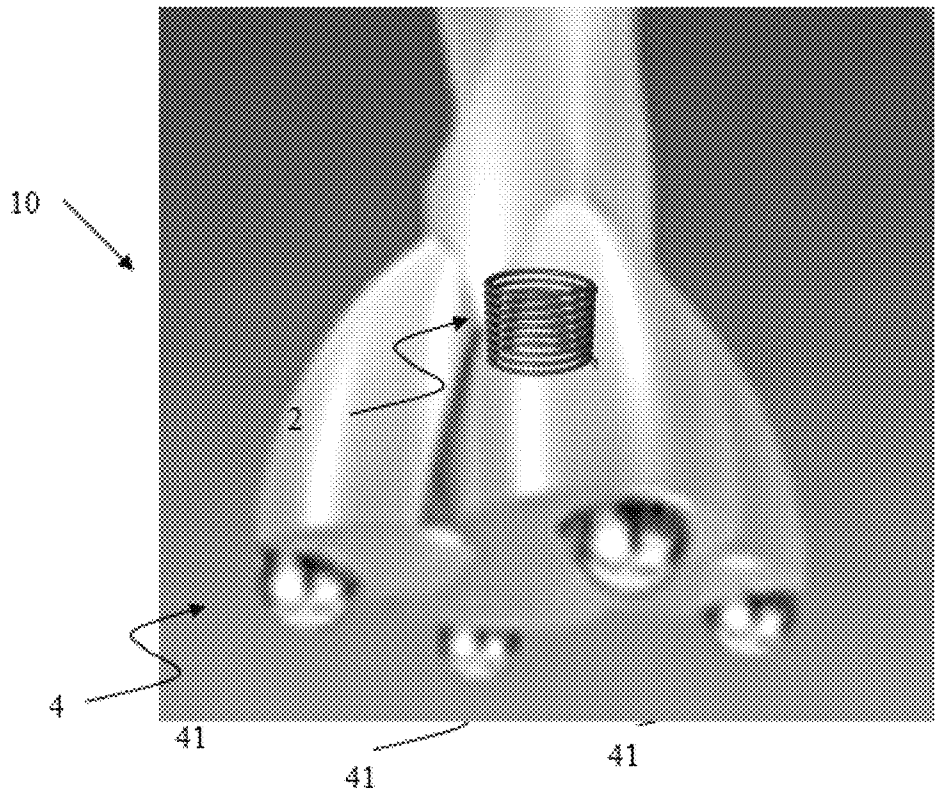
Figure 1C:
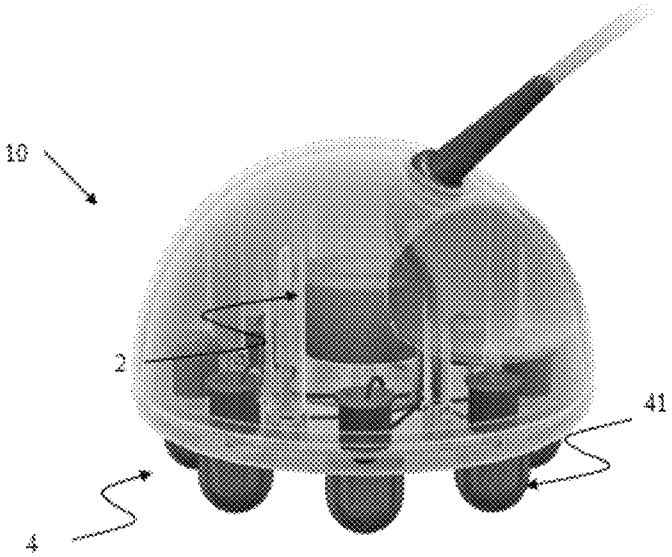
Figure 1D:
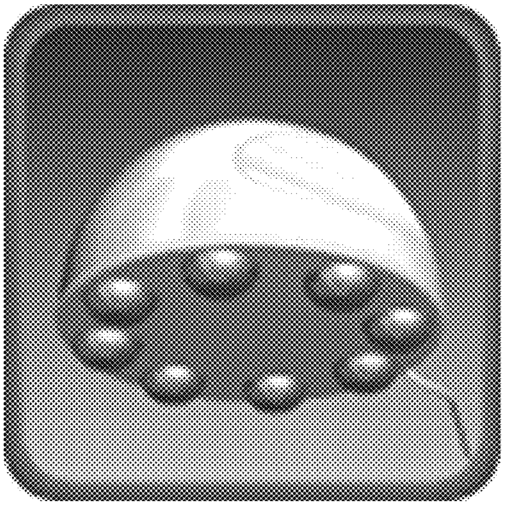

Reference is now made to FIGS. 1B-1D, illustrating the system 10 according to preferred embodiment of the present invention.

According to a preferred embodiment of the present invention, the deep tissue diathermy device (4) comprises:

a. at least one electrical output device adapted to generate electrical current; and, b. at least two electrodes (41) electrically coupled to said electrical output device and placed on said skin region.

According to said embodiment all said electrodes are adapted to simultaneously apply said electrical current to said skin region.

FIG. 1B illustrates system 10 in which the deep tissue diathermy device (4) comprises 4 electrodes (denoted by numerical reference 41).

FIGS. 1C-1D illustrate the system 10 in which the deep tissue diathermy device (4) comprises 8 electrodes (denoted by numerical reference 41).

Figure 1E:
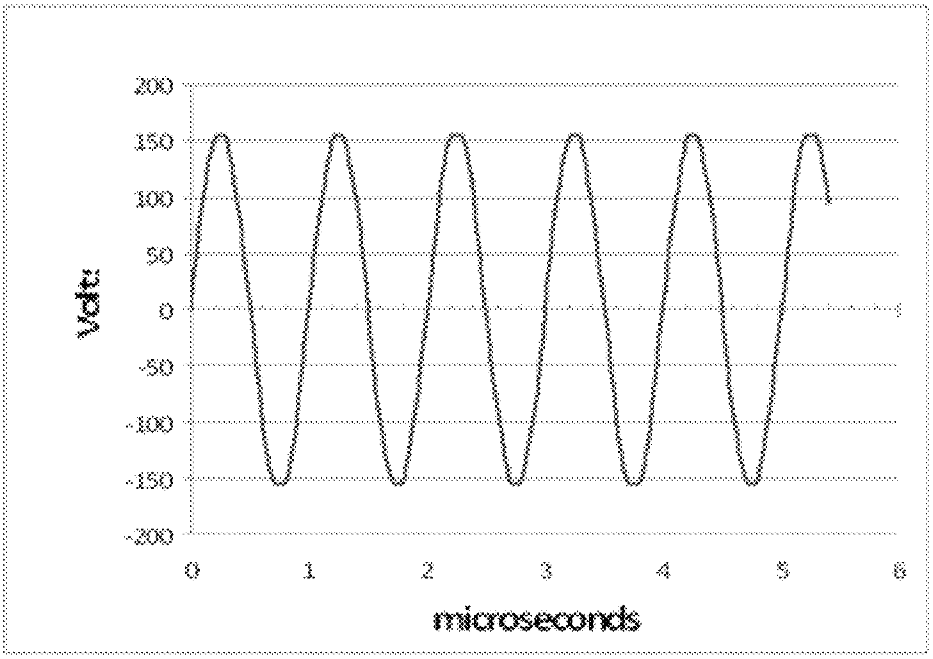
FIG. 1E is a diagram illustrating an example of electrical current applied by the deep tissue diathermy device (4). The current involves a maximal amplitude of 160 volts, and a frequency close to 1 Hz.

Reference is now made to FIG. 1E illustrating an example of electrical current applied by the deep tissue diathermy device (4). The current involves a maximal amplitude of 160 volts, and a frequency close to 1 Hz.

According to another embodiment of the present invention, the pulsed electromagnetic frequency generator is adapted to provide an electromagnetic field which varies with time (dynamic magnetic field).

According to another embodiment of the present invention, the pulsed electromagnetic frequency generator (2) which provides electromagnetic pulses to the patient's skin is positioned near the treated tissue and emits a dynamic magnetic field which varies with time. The dynamic magnetic field can vary according to any specific treatments. For examples, to stimulate angiogenesis, pulses at a frequency of 16 Hz, intensity of 12 Gauss and duration of about 5 milliseconds are generated. Alternatively, to stimulate collagen production a triangular wave pulses at a frequency of 25 Hz and intensity of 40 Gauss are generated.

The deep tissue diathermy device (4) is adapted to apply heat to said region of a patient's skin up to temperature T. According to one embodiment of the present invention the heat is applied by passing electrical current through the tissue. The electrical current can be performed in one of the following three manners:

1. Through at least one electrode which is in direct physical contact with the skin;
2. through at least one electrode which is not in physical contact with the skin, and the electrical current is transferred by induction.
3. through at least one antenna which passes the electrical current to the skin via electromagnetic induction.

Figure 2:
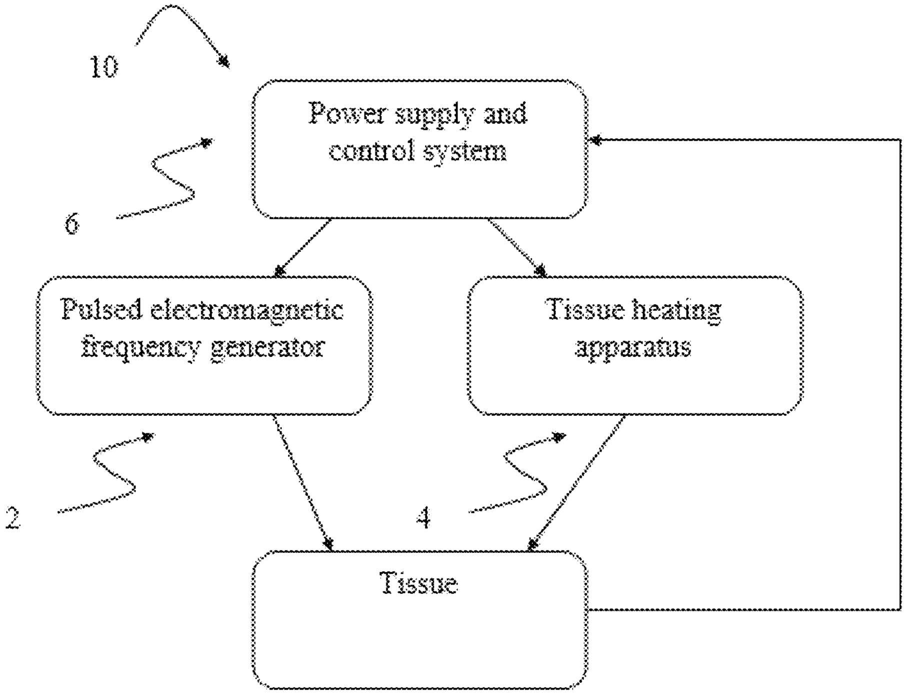
FIG. 2 is a schematic representation of a skin viability improving system (10), comprising a pulsed electromagnetic frequency generator (2), a deep tissue diathermy device (4) and a power supply and control system (6).

Reference is now made to FIG. 2, which illustrates another embodiment of the present invention, According to that embodiment the system additionally comprising a control system (6) adapted to regulate said electromagnetic pulses and/or said electromagnetic pulses. According to another embodiment of the present invention the treatment is provided only in safe treatment parameters.

Safe treatment parameters are defined by the parameters in table 1:

TABLE 1 safe treatment parameters

| parameter | Values |
|---|---|
| Time, t | 0-600 Minutes |
| Temperature, T | 25-100 Celsius |
| Duty cycle t/T | 0-100% |
| Frequency MHz | DC – 40 Mhz |
| power P | 0-100 Watt |
| Energy E | 0-200 Jowls |
| magnetic field intensity B | 0-10 Tesla |
| Depth D of said treated tissue | 30 Millimeters |

Unsafe safe treatment parameters are defined by the parameters in table 2:

TABLE 2 unsafe treatment parameters

| parameter | Values |
|---|---|
| Time, t | >10 hours (none stop) |
| Temperature, T | >80 Celsius |
| Duty cycle t/T | N/A |
| Frequency MHz | >40 MHz |
| power P | >100 Watt |
| Energy E | >200 Jowls |
| magnetic field intensity B | >10 Tesla |
| Depth D of said treated tissue | >30 Millimeter |

According to another embodiment, the control system (6) additionally comprises:

(a) processing means (a processor), adapted to store in a communicable database predetermined parameters defining (i) safe treatment parameters and (ii) unsafe treatment parameters; said parameters are selected from a group consisting of time t of said treatment, temperature T of said tissue, duty cycle t/T, Frequency F, power P, Intensity I of said ultrasound diathermy, energy E applied by the pulses of said pulsed electromagnetic frequency generator, treatment depth D of said treated tissue, magnetic field intensity B, tissue impedance, specific absorption rate (SAR), superficial muscle contractions or a combination thereof, (b) sensing means; adapted to sense electromagnetic radiation and heat radiation parameters selected from a group consisting of time t of time t of said treatment, temperature T of said tissue, duty cycle t/T, Frequency F, power P, Intensity I of said ultrasound diathermy, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof, (c) regulating means (regulator), adapted to allow said pulsed electromagnetic radiation and heat radiation if said parameters are within said safe treatment parameters and to stop the pulsed electromagnetic radiation if the radiation parameters are in said unsafe treatment parameters. In some embodiments, the regulator may be implemented as control circuitry in connection with a controller that is communicated with the processor, in some embodiments. In some embodiments, the regulator comprises controller circuitry communicated with the processor.

According to another embodiment, the system as defined above, additionally comprising sensors for monitoring physical parameters selected form a group consisting of time t of said treatment, temperature T of said tissue, duty cycle t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof.

In some embodiments, the processing means includes a processor configured to communicate with a non-transitory computer readable medium. The non-transitory computer readable medium is configurable as a memory which is configured to store instructions thereon, which, when executed by the processor, causes the processor to carry out instructions.

The sensors receives said parameters from the treated tissue and changes the parameters of the pulsed electromagnetic frequency generator (2) and the deep tissue diathermy device (4) to optimize the effect of each component and/or to augment the synergistic effect of both components, whilst avoiding harm to the tissue.

According to another embodiment of the present invention the shape of the electromagnetic pulse is selected in a non-limiting manner from a group consisting of square wave, a sine wave, a triangular wave, sawtooth wave, ramp waves, a spiked wave or any other mathematical combination.

According to another embodiment, the system as defined above is adapted to provide electromagnetic pulse at a frequency of 16 Hz which increases from 0 Gauss to 12 Gauss. According to another embodiment, the system as defined above is adapted to provide electromagnetic square wave pulse at a frequency of 16 Hz which increases from 0 Gauss to 40 Gauss.

Figure 3:
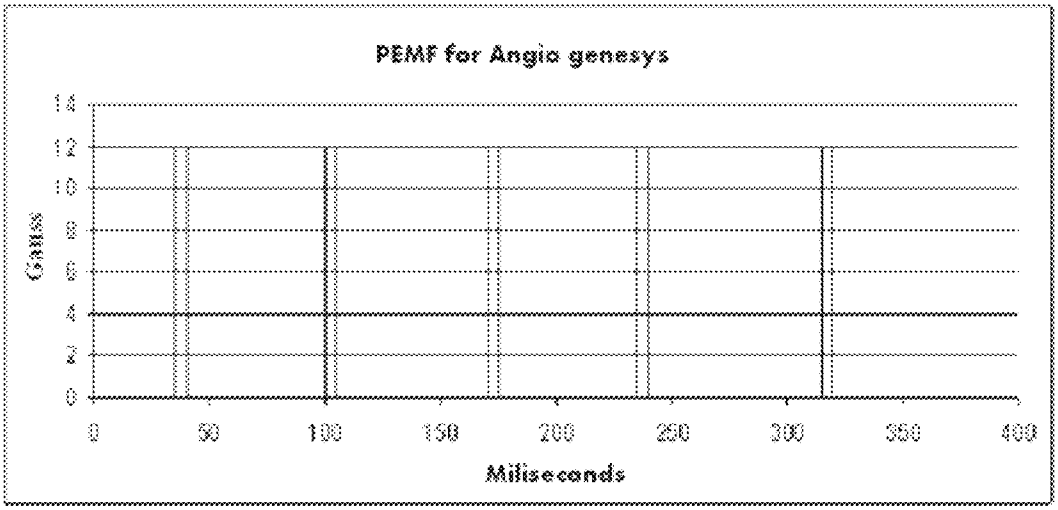
FIG. 3 is a schematic representation of square waves at a rate of 16 Hz in duration of about 5 milliseconds in an intensity of 12 Gauss which stimulate angiogenesis.

According to another embodiment, the system as defined above is adapted to provide short square waves at a rate of 16 Hz in duration of about 5 milliseconds in an intensity of 12 Gauss. Such square wave pulses are especially provided to stimulate angiogenesis. Reference is now made to FIG. 3, which illustrates such square wave pulse.

Figure 4:
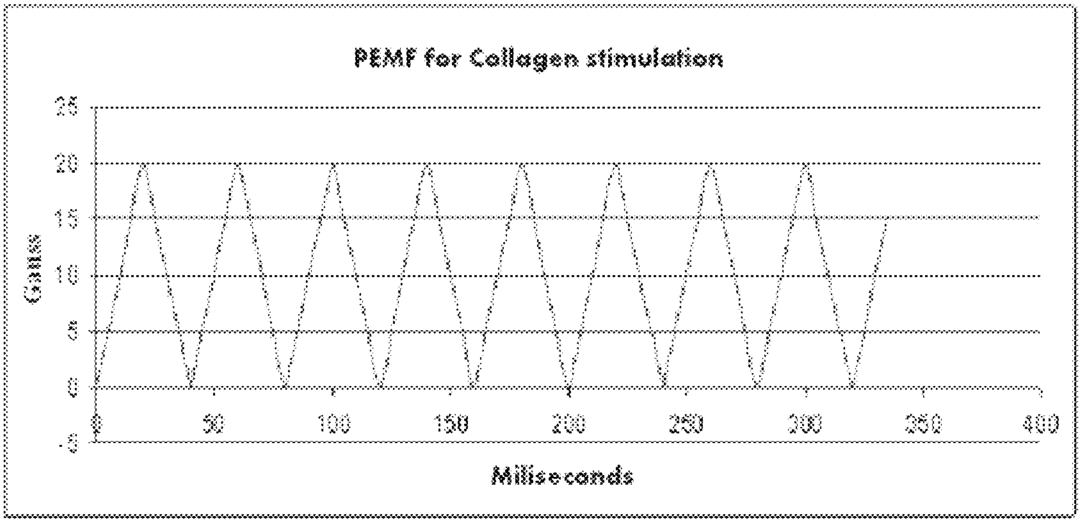
FIG. 4 is a schematic representation of triangular wave pulses at a frequency of 25 Hz and intensity of 40 Gauss which stimulate collagen production.

According to another embodiment, the system as defined above is adapted to provide triangular wave pulses at a frequency of 25 Hz and intensity of 40 Gauss. Such pulses are especially provided to stimulate collagen production. Reference is now made to FIG. 4, which illustrates such triangular wave pulses.

According to another embodiment, the system as defined above is adapted to provide alternating current (AC) at a frequency of 1 MHz.

According to another embodiment, the system as defined above is adapted to provide intensity of about 80 $J/cm^2$ sec.

According to another embodiment of the present invention the magnetic field intensity B of each pulse applied by said pulsed electromagnetic frequency generator (2) ranges between about 0 and about the max magnetic field used in MRI devices (i.e., 3 Tesla).

According to another embodiment of the present invention, the duration of each pulse applied by said pulsed electromagnetic frequency generator (2) ranges between about 3 and about 1000 milliseconds.

According to another embodiment of the present invention, the frequency F applied by the pulses of said pulsed electromagnetic frequency generator (2) ranges between about 1 and about 1 MHz.

According to another embodiment of the present invention, the energy E applied by the pulses of said pulsed electromagnetic frequency generator (2) ranges between about 1 and about 150 watts per pulse.

According to another embodiment of the present invention, the deep tissue diathermy device (4) is selected in a non-limiting manner from a group consisting of electric diathermy or any device emitting RF radiation, any device adapted to deliver RF energy, or any device adapted to conduct RF energy, absorbed by subcutaneous tissue.

According to another embodiment of the present invention, the deep tissue diathermy device (4) is selected in a non-limiting manner from a group consisting of an ultrasonic diathermy, an optical device, electromagnetic induction, sound waves emitting instrument, direct heat applying instrument, or from any other means of heating subcutaneous tissue to temperature T.

According to another embodiment of the present invention, the optical device is adapted to emit light in wavelengths absorbed by subcutaneous tissue such that said subcutaneous tissue is heated.

According to another embodiment of the present invention, the sound waves emitting instrument is adapted to emit sound waves absorbed by the subcutaneous tissue such that said subcutaneous tissue is heated.

According to another embodiment of the present invention, the temperature T is higher than about 30 and lower than about 100 degrees.

According to another embodiment of the present invention, the power supply and control system (6) includes a mechanism for skin cooling.

According to another embodiment of the present invention, system (10) is encased in at least one platform.

According to another embodiment of the present invention, the pulsed electromagnetic frequency generator (2) and said deep tissue diathermy device (4) have more than one applicator to treat more than one body part simultaneously.

According to another embodiment of the present invention, the pulsed electromagnetic frequency generator (2) has electrostatic shielding.

Is should be emphasized that the system as defined in any of the embodiments produces synergic outcomes in the following three ranges: The immediate (short) range, in the intermediate range and in the long range.

In the immediate (short) range—the contraction and thickening of collagen fibers occur, which in turn results in an overall tightened and rejuvenated appearance of the skin.

In the intermediate range (i.e., about two to three weeks)—new epidermal cells and new collagen fibers are produced.

In the long range (i.e., about a month)—the cellulite is scattered.

Figure 5:
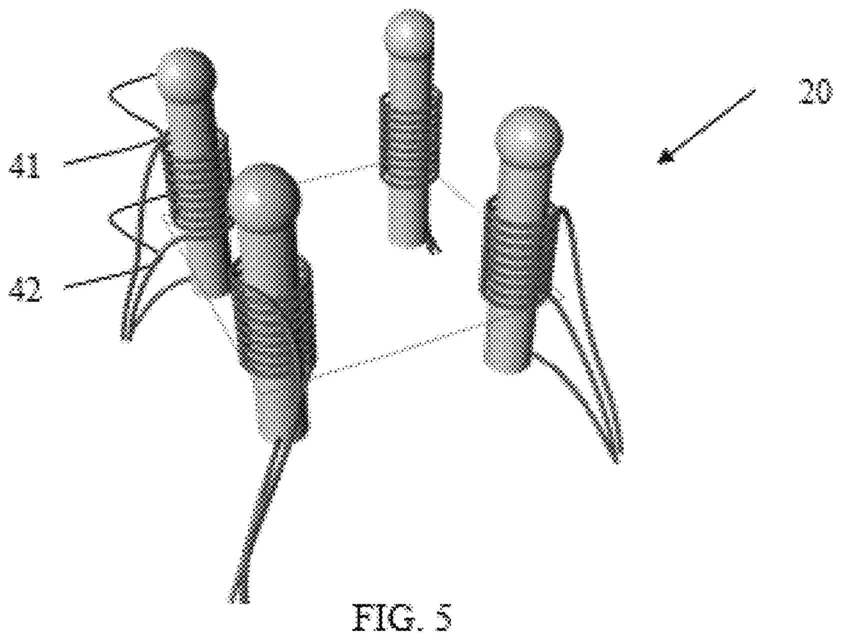
FIGS. 5-6 illustrate another embodiment of the skin viability improving system (20).
Figure 6:
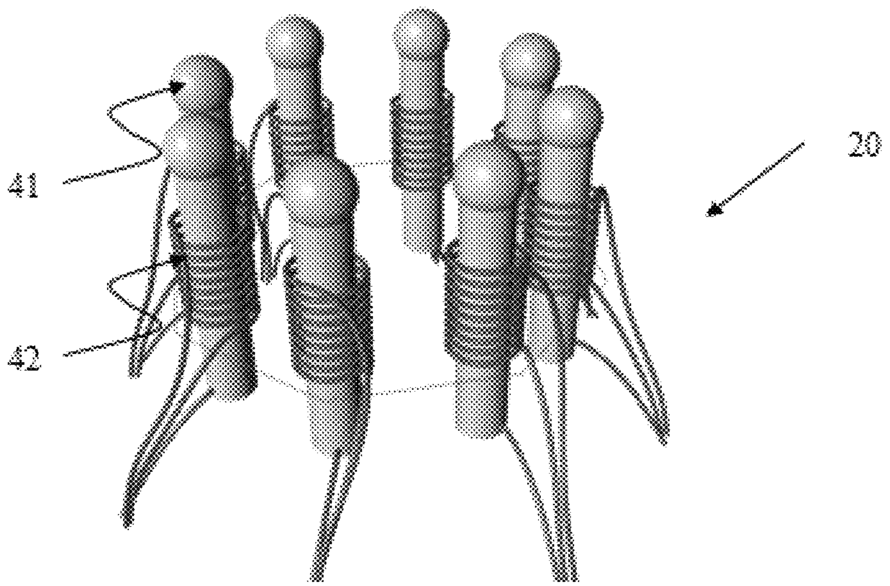

Reference is now made to FIGS. 5-6, which illustrate another system (20) according to a preferred embodiment of the present invention. According to this embodiment, an integrated system (20) adapted to increase skin rejuvenation of a region of a patient's skin is provided.

The system 20 comprises at least two electrodes (41) adapted to be placed on said region of a patient's skin; each of said electrodes is a least partially coiled (or looped) via a coil (42).

It should be emphasized that each of said electrodes (41) is adapted for both (i) providing electromagnetic pulses to said region of a patient's skin (via said coil (42); and, (ii) applying heat up to temperature T to said region of a patient's skin.

Furthermore, it should be emphasized that all said electrodes provide simultaneously electromagnetic pulses to said region of a patient's skin; and, apply heat up to temperature T to said region of a patient's skin.

The heat is provided to the skin by applying electrical current through said electrodes (41) which is absorbed by subcutaneous tissue.

FIG. 5 illustrates such a system (20) comprising 4 electrodes (denoted as electrodes (41) and FIG. 6 illustrates such a system (20) comprising 8 electrodes (denoted as electrodes (41).

It should be emphasized that the application of said system (20 increases said skin rejuvenation such that said skin rejuvenation increase (SRI) is greater than the sum of said SRI provided by electromagnetic pulses increase and said SRI provided by said deep tissue diathermy device increase.

According to another embodiment of the present invention the electromagnetic pulse in system (20) is a triangular shaped at frequency of 25 Hz and intensity of 40 Gauss.

According to another embodiment of the present invention the electromagnetic pulse in system (20) is square shaped at a frequency of 16 Hz, duration of about 5 milliseconds and intensity of 12 Gauss.

According to another embodiment of the present invention, the system (20) reduces side effects and/or harmful effects of said electromagnetic pulses and/or said deep tissue diathermy such that said reduction of said side effects and/or said harmful effects is greater than the sum of said reduction of said electromagnetic pulses and/or said reduction of said deep tissue diathermy.

According to another embodiment of the present invention, the system (20) additionally comprises a control system (6) adapted to regulate said electromagnetic pulses and/or said electromagnetic pulses.

According to another embodiment of the present invention, the system (20) is adapted to provide a dynamic magnetic field such that said electromagnetic pulses vary with time.

According to another embodiment of the present invention, the shape of said electromagnetic pulse in system (20) is selected in a non-limiting manner from a group consisting of square wave, a sine wave, a triangular wave, sawtooth wave, ramp waves, spiked wave or any other mathematical combination.

According to another embodiment of the present invention, the magnetic field intensity B in system (20) of each pulse applied by said pulsed electromagnetic frequency generator (2) ranges between about 0 and about 3 Tesla.

According to another embodiment of the present invention, the duration of each pulse applied in system (20) ranges between about 3 and about 1000 milliseconds.

According to another embodiment of the present invention, the frequency F applied by the pulses of said system (20) ranges between about 1 Hz and about 1 MHz.

According to another embodiment of the present invention, the energy E applied by said system (20) ranges between about 1 and about 150 watts per pulse.

According to another embodiment of the present invention, the temperature T is higher than about 30 and lower than about 100 degrees.

According to another embodiment of the present invention, the power supply and control system (6) in system (20) monitors physical tissue parameters and changes applied heat and electromagnetic pulses accordingly.

According to another embodiment of the present invention, the power supply and control system (6) additionally comprises.

a. processing means, adapted to store in a communicable database predetermined parameters defining (i) safe treatment parameters and (ii) unsafe treatment parameters; said parameters are selected from a group consisting of time t of said treatment, temperature T of said tissue, ratio t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;

b. sensing means; adapted to sense electromagnetic radiation and heat radiation parameters selected from a group consisting of time t of time t of said treatment, temperature T of said tissue, ratio t/T, Frequency F, power P, Intensity I of said ultrasound irradiation, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof, c. regulating means, adapted to allow said electromagnetic radiation and heat radiation if said parameters are within said safe treatment parameters and to stop the electromagnetic radiation if the radiation parameters are in said unsafe treatment parameters.

According to another embodiment of the present invention, the power supply and control system (6) includes a mechanism for skin cooling.

According to another embodiment of the present invention, the system (20) is especially adapted to increase skin rejuvenation in the immediate (short) range.

According to another embodiment of the present invention, the system (20) is especially adapted to increase skin rejuvenation in the intermediate range.

According to another embodiment of the present invention, the system (20) is especially adapted to increase skin rejuvenation in the long range.

Figure 7:
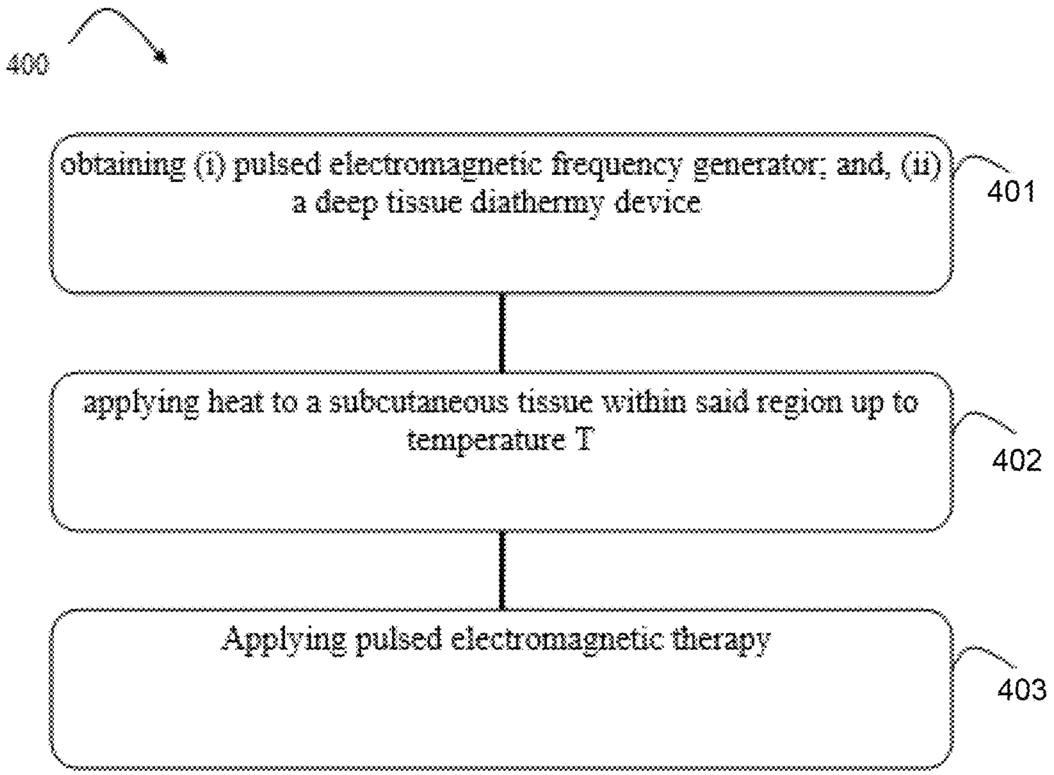

Reference is now made to FIG. 7, schematically illustrating one possible method (400) of increasing skin rejuvenation of a region of a patient's skin. The method comprising steps selected inter alia from obtaining (i) pulsed electromagnetic frequency generator; and, (ii) a deep tissue diathermy device (401); applying heat to a subcutaneous tissue within said region up to temperature T (402); said temperature T is optimized for production of new dermal ground substance and collagen contraction. While the collagen contraction tightens the skin and conceals wrinkles immediately, the dermal proliferation and new collagen production has a later effect. The next step is applying additional pulsed electromagnetic field (403) which generates a healing mechanism of the heated skin, which includes growth factor and cytokines release and eventually angiogenesis.

Figure 8:
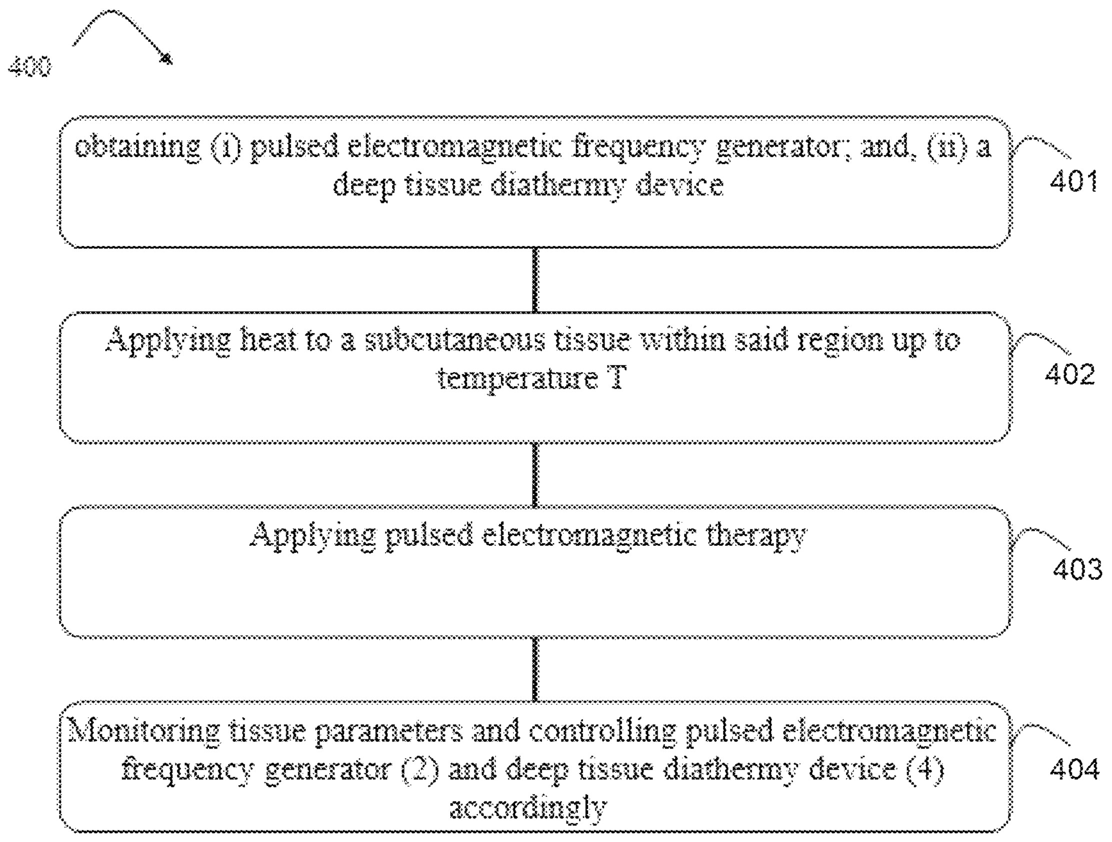
Figure 9:
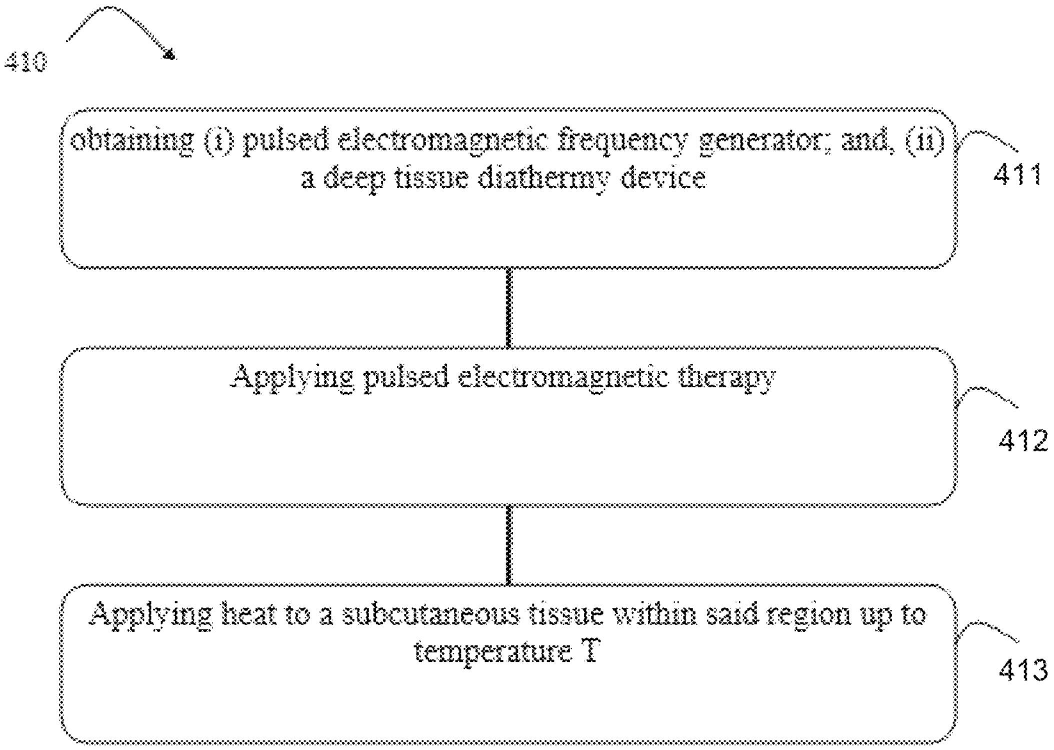

Reference is now made to FIG. 8, which illustrates another preferred method of the present invention. According to this embodiment, the method 400 additionally comprises the step of: monitoring and/or controlling said steps of applying heat to a subcutaneous tissue within said region and/or said step of applying pulsed electromagnetic therapy to said region (404). Reference is now made to FIG. 9, schematically illustrating one possible method (410) of increasing skin rejuvenation of a region of a patient's skin. The method comprising steps selected inter alia from obtaining (i) pulsed electromagnetic frequency generator; and, (ii) a deep tissue diathermy device (411). The next step is applying additional pulsed electromagnetic field (412) which generates a healing mechanism of the heated skin, which includes growth factor and cytokines release and eventually angiogenesis. The final step is applying heat to a subcutaneous tissue within said region up to temperature T (413); said temperature T is optimized for production of new dermal ground substance and collagen contraction. While the collagen contraction tightens the skin and conceals wrinkles immediately, the dermal proliferation and new collagen production has a later effect.

Figure 10:
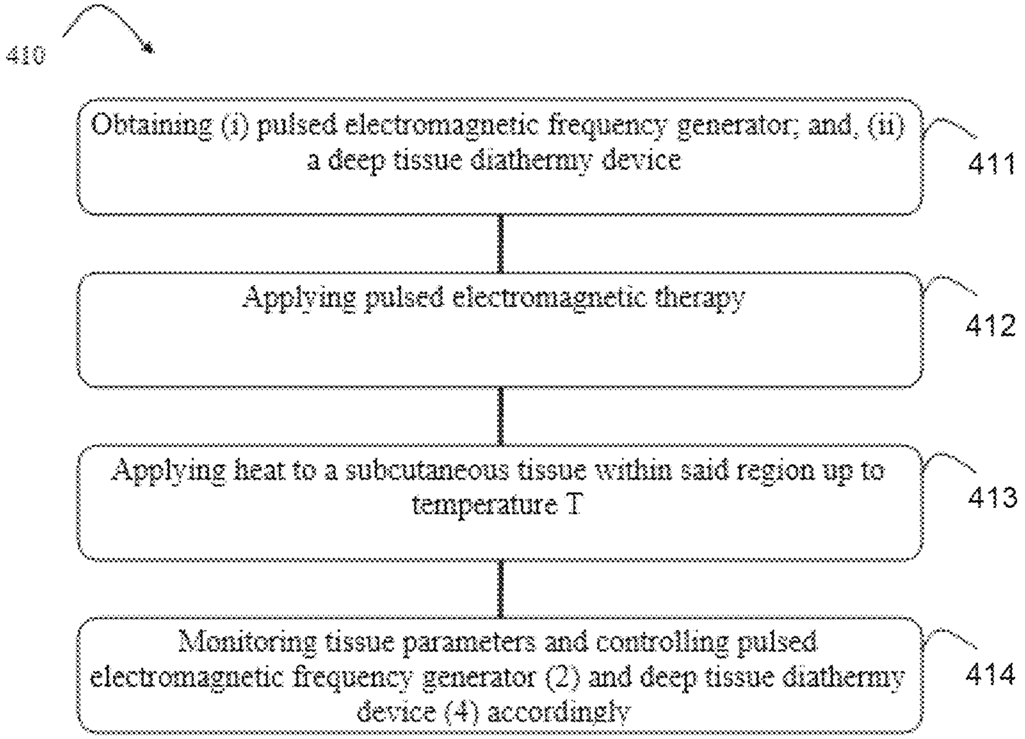
Figure 11:
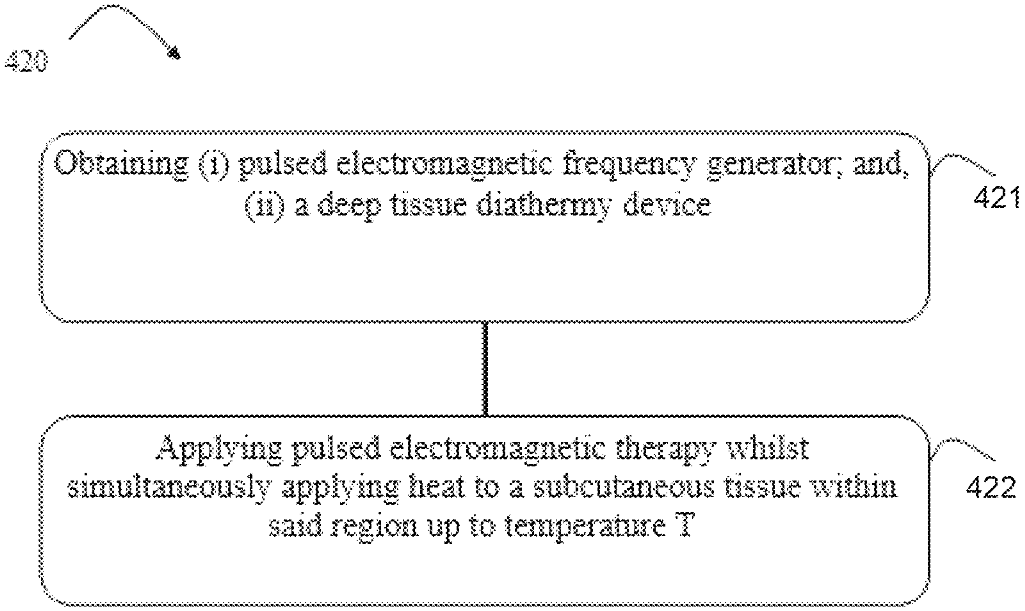

Reference is now made to FIG. 10, which illustrates another preferred method of the present invention. According to this embodiment, the method 410 additionally comprises the step of: monitoring and/or controlling said steps of applying heat to a subcutaneous tissue within said region and/or said step of applying pulsed electromagnetic therapy to said region (414). Reference is now made to FIG. 11, schematically illustrating one possible method (420) of increasing skin rejuvenation of a region of a patient's skin. The method comprising steps selected inter alia from obtaining (i) pulsed electromagnetic frequency generator; and, (ii) a deep tissue diathermy device (421). The next step is applying additional pulsed electromagnetic field (422) whilst simultaneously applying heat to a subcutaneous tissue within said region up to temperature T. The electromagnetic pulses generate a healing mechanism of the heated skin, which includes growth factor and cytokines release and eventually angiogenesis. The heat applied temperature T is optimized for production of new dermal ground substance and collagen contraction. While the collagen contraction tightens the skin and conceals wrinkles immediately, the dermal proliferation and new collagen production has a later effect.

Reference is now made to FIG. 12, which illustrates another preferred method of the present invention. According to this embodiment, the method 420 additionally comprises the step of: monitoring and/or controlling said steps of applying heat to a subcutaneous tissue within said region and/or said step of applying pulsed electromagnetic therapy to said region (424).

According to another embodiment of the present invention, each of the methods as defined above additionally comprising step of selecting said temperature T from a region of about 30 to about 100 degrees.

According to another embodiment of the present invention, each of the methods as defined above additionally comprising step of applying a dynamic magnetic field onto said region. According to another embodiment of the present invention, each of the methods as defined above additionally comprising steps of:

a. storing in a communicable database predetermined parameters defining (i) safe treatment parameters and (ii) unsafe treatment parameters; said parameters are selected from a group consisting of time t of said treatment, temperature T of said tissue, duty cycle t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
b. sensing electromagnetic radiation and heat radiation parameters selected from a group consisting of time t of time t of said treatment, temperature T of said tissue, duty cycle t/T, Frequency F, power P, Intensity I of said ultrasound diathermy, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
c. allowing said electromagnetic radiation and said heat radiation if parameters are within said safe treatment parameters and stopping the electromagnetic radiation if the radiation parameters are in said unsafe treatment parameters.

According to another embodiment of the present invention, the step of applying heat is performed by devices selected from a group consisting of: ultrasonic diathermy, an optical device, electromagnetic induction, sound waves emitting instrument, direct heat applying instrument, or from any other means of heating subcutaneous tissue to temperature T.

According to another embodiment of the present invention, each of the methods as defined above additionally comprising step of selecting the magnetic field intensity B of each pulse applied by said step of applying pulsed electromagnetic therapy to said region to be higher than about 0 and lower than about max magnetic field used in MRI devices (i.e., 3 Tesla). According to another embodiment of the present invention, each of the methods as defined above additionally comprising step of selecting the frequency F applied by the pulses applied by said step of applying pulsed electromagnetic therapy to said region to be higher than about 1 Hz and lower than about 40 MHz.

According to another embodiment of the present invention, each of the methods as defined above additionally comprising step of selecting the energy E applied by said step of applying pulsed electromagnetic therapy to said region to be higher than about 1 and lower than about 150 watts per pulse.

According to another embodiment of the present invention, in each of the methods as defined above the step of applying heat lasts about 0.01 to 100 minutes.

According to another embodiment of the present invention, in each of the methods as defined above the pulsed electromagnetic field lasts about 0.01 to 100 minutes.

According to another embodiment of the present invention, in each of the methods as defined above the steps of applying heat and applying the pulsed electromagnetic therapy are simultaneous, sequential or separate.

According to another embodiment of the present invention, in each of the methods as defined above the method is repeated 1 to 100 times in each treatment.

According to another embodiment of the present invention, a typical protocol for the pulsed electromagnetic frequency generator (4) includes for example, and in a non limiting manner, a preset number of 1 microsecond period pulses with duty cycle of 50% and a pause of up to 250 microsecond (in which the preset number of pulses correlates with energy to be supplied to skin under the treatment.) According to another embodiment of the present invention, a typical protocol for the pulsed electromagnetic frequency generator (4) includes for example, and in a non limiting manner 10 pulses, of 1 microsecond period with 50% duty cycle and preset pause of up to 512 microseconds (in which the pause correlates with energy to be supplied to skin under the treatment).

According to another embodiment of the present invention, a typical protocol for the pulsed electromagnetic frequency generator (4) includes for example, and in a non limiting manner, a repetition of the previous protocol, wherein the number of pulses administered is a multiplication of 10.

This invention also relates to methods and devices for the tightening of skin and/or reduction of skin laxity by selectively opening or closing a plurality of small wounds formed by incision or excision of tissue. For example, tissue excision can be performed by fractional ablation of the epidermal and/or dermal layer of the skin with at least one hollow coring needle (or punch), by fractional laser ablation, by fractional radiofrequency (also refers to as RF) ablation, and/or by fractional ultrasonic ablation (using ultrasound). Various methods and devices are proposed to close the small wounds, including tunable or smart dressings that allow for titration of the tightening effect after application to the skin of a patient.

The device of the present invention excises a pattern of small dermal skin cores at desired density, and direction. Then, the remaining holes in the skin are closed, directionally, using manual compression methods such as compression tape or glue.

According to one embodiment of the present invention, the device of the present invention is designed for the removal of skin micro-cores in fractional manner—for different indications (e.g., skin resurfacing/wrinkle/lifting etc.).

According to one embodiment of the present invention, the coring mechanism is a single-use disposable cartridge consisting of at least one (preferably six (6)), up to 0.75 mm in diameter, hollow needles (or punches) inserted into the skin while rotating at about 7000 RPM with a maximum penetration depth of up to 3.5 mm to remove up to 15% of skin in the treatment area. This invention further relates to methods and devices for skin treatment. More, specifically, this invention relates to methods and devices for skin coring and tightening that would benefit from endorsing collagen growth in a predetermined direction and providing directional skin tightening in said skin tissue thus, providing skin restoration or tightening. The device could be utilized in a wide variety of fields e.g., skin laxity, skin resurfacing, cheek wrinkles treatments, wrinkles treatments, folds treatments, acne scars removal, dyschromia treatment, striae treatment, surgical scars removal, cellulite treatment, tattoos removal and any combination thereof.

In particular embodiments, the present invention provides one or more of the following advantages. First, the methods and devices herein enable visualization of results in real time during the course of the treatment. One can envision asking the patient for feedback in real time during the treatment and adjusting the tightening to the patient preference. Second, the methods and devices herein are tunable, thereby allowing for titration of tightening after surgical hole or slit formation. For example, the tunable or smart dressings described herein allow adjustment of the tightening intensity, direction, and spatial distribution after the dressing has been applied or affixed to the patient's skin. In another example, titratable tightening can be achieved by selectively closing or opening a subset of slits or holes produced in an array. Third, the methods and devices herein requires less skill than that of a surgeon. One can envision treatment of patients in an outpatient setting, rather than requiring an inpatient, surgical setting. Fourth, the methods and devices herein constitute minimally invasive techniques, which can provide more predictable results and/or risk factors than that for more invasive techniques (e.g., plastic surgery) or non-invasive energy-based techniques (e.g., laser, coblation, coagulation, microwave energy, radiofrequency, or ultrasound). Fifth, the methods and devices herein can allow for less discriminate methods for treating the skin by forming holes or slits because the methods and devices allow for more discriminate control for closing such holes or slits. Sixth, the methods and devices herein can allow for rapid closing of holes or slits after treating the skin (e.g., within a few seconds after treating skin, such as within ten seconds), thereby minimizing the extent of bleeding and/or clotting within the holes or slits. Finally, the methods and devices herein can be useful for maximizing the tightening effect while minimizing healing time by optimizing tightening (e.g., by controlling the extent of skin pleating, such as by increasing the extent of skin pleating for some applications or skin regions and by decreasing the extent of skin pleating for other applications or skin regions, as described herein).

Definitions

The term "about" refers hereinafter to +/−25% of any recited value.

The term "overlap" refers hereinafter to vertex, facet, cross sectional area and any combination thereof.

The term "Optical coherence tomography (OCT)" refers hereinafter to a non-invasive imaging. In other words, OCT is an imaging technique that uses low-coherence light to capture micrometer-resolution, two- and three-dimensional images from within optical scattering media (e.g., biological tissue). It is used for medical imaging and industrial non-destructive testing (NDT). Optical coherence tomography is based on low-coherence interferometry, typically employing near-infrared light. The use of relatively long wavelength light allows it to penetrate into the scattering medium. Confocal microscopy, another optical technique, typically penetrates less deeply into the sample but with higher resolution.

The term "mechanical visualization" refers hereinafter to either the use of ultrasound or OCT to image the undersurface of the treated area skin/tissue. Such mechanical visualization is used to efficiency select the preferred location of the tissue to be treated to enhance outcome of said treatment. It should be noted that according to the present invention the term 'mechanical visualization' also includes cameras for imaging the surface of the treated area skin/tissue.

The term "incised" tissue portion or "incision" refers hereinafter to a cut, abrasion, or ablation of tissue, including a tissue portion in a skin region, or the act of cutting, abrading, destroying, or ablating tissue, a skin region, or one or more tissue portions. For example, an incision includes any cut, abrasion, or ablation into tissue, which can result in destruction of tissue or a portion thereof and, thereby, produce one or more holes or slits in the skin region. Exemplary methods of forming incised tissue portions or incisions include use of one or more blades, one or more solid needles, fractional laser ablation, fractional radiofrequency ablation, coblation, coagulation, microwave energy and/or fractional ultrasonic ablation, any useful tool for forming incisions, or any methods and apparatuses described herein.

The term "excised" tissue portion or "excision" refers hereinafter to a removed tissue, including a tissue portion from a skin region, or the act of removing tissue or one or more tissue portions from a skin region. Excision is usually referred to as "to surgically remove". This term is often used in reference to removing a mass, excision means that tissue is removed, using an excisor, e.g., a scalpel, laser, coblation, coagulation, ablation, ultrasound, microwave energy, RF, application of heat (to evaporate skin portions), mechanical applicator that 'drills' through the skin whilst suction is applies (during the drilling or thereafter) to remove the excised skin portion, or any another instrument. For example, an excision includes any removed tissue or tissue portion from a skin region, which can result in excised tissue portions having a particular geometry (e.g., a cylindrical geometry, rectangular, triangle etc. or any arbitrary shape) and produce one or more holes (i.e., negative space created by the removal of tissue) in the skin region. Exemplary methods of forming excised tissue portions or excisions include use of one or more hollow needles (optionally include one or more notches, extensions, protrusions, and/or barbs), one or more microaugers, one or more microabraders, any ablative means (an ablator) (including ablative lasers etc.)—may be used for incision and for excision, any useful tool for forming excisions, or any methods and apparatuses described herein.

The term “application of compression forces” refers hereinafter to a physical change in the compression tape (as will be disclosed hereafter). In this case, the forces applied are compression forces to compress the tape.

The term “application of expansion forces” refers hereinafter to a physical change in the compression tape (as will be disclosed hereafter). In this case, the forces applied are stretching forces to expand the tape.

The present invention features methods and devices to directionally tightening the skin after coring thereof (i.e., having one or more incised or excised tissue portions). In particular, exemplary devices include selectively opening or closing of holes and/or slits using a compression tape.

The device of the present invention is designed to enhance quality and productivity of skin laxity reduction procedures using advanced robotics, machine vision and software engineering.

The device implements dermal micro-coring approach to skin tightening. The device excises a pattern of predetermined small size dermal skin cores at desired density, and direction. The formed holes in the skin are then closed, directionally, using manual compression methods such as compression tape or glue.

According to one embodiment of the present invention, the treatment parameters; i.e., desired density of the cores, depth, diameter etc. are automatically adjusted to the treated patient.

According to one embodiment, the density of the coring will be 5-20% of the selected treated area. It is noted that according to another embodiment, the coverage rate (namely, the diameter of holes multiplied by number of holes) will be 5-20% of the selected treated area.

The device includes the following elements:

1. At least one Robotic Arm and Controller that control the positioning of the arm relatively to the treated skin area.
2. Skin Coring Instrument and controls
3. RTC (real time controller) unit that includes at least one engine (e.g., a rotor, a motor or robotic servo-motor) that controls the rotation, translation as well as the orientation of the robotic arm relatively to the treated skin area
4. Imaging Subsystem—to analyze treatment area and to guide the coring instrument.
5. Vacuum Subsystem—suction is applied to remove the excised tissue from the skin following the incision. Or alternatively a retention element (a retainer) is used that will hold the excised tissue, rendering the vacuum subsystem redundant. Hence, a vacuum is thus avoided by such embodiments and rendered unnecessary.
6. Stretching/compression device (e.g., compression tape) that will enable compression of the skin.

The skin coring instrument includes coring punches (i.e., the micro needles); either a single or multi-punch array for either simultaneous or sequentially coring the skin. It should be noted that the coring punches could be at least partially disposable.

According to one embodiment of the present invention, the coring instrument is a mechanical device that allows for small (0.25 to 2.0 mm), circular skin cores to be removed.

According to another embodiment of the present invention any cross section (other than circular) is also within the scope of the present invention. E.g., circular, rectangular, triangular, hexagonal, oval, staggered rows, parallel rows, a spiral pattern, a square or rectangular pattern, a radial distribution and any combination thereof.

According to one embodiment, the coring instrument, has between 1 and 7 rotating (100-7000 RPM) coring punches that can be set to penetrate the skin surface and core to a depth of 1 to 4 mm. Suction is applied to remove the cores from the skin following the incision. The coring punches are disposable and a new one is used for each subject.

The coring element (e.g., the micro needles) has at least one sharp dermal punch to core out tissue (e.g., 0.25 mm-2.0 mm radius).

According to one embodiment, the dermal punches have a stopping mechanism (a stopper) to limit coring depth. A typical coring depth will be configurable between 1 mm and 6 mm (and more specifically 1-4 mm) in steps of 0.5 mm.

According to one embodiment, the coring depth resolution will be +/−0.1 mm.

According to one embodiment, each Individual punch rotates between 1000-7000 RPM.

According to one embodiment, each individual punch is able to translate into skin up to 500 mm/sec, preferably the translation speeds will be less than 300 mm/sec.

According to one embodiment, each individual punch rotates at a speed that is less than 30 degree/sec.

According to one embodiment, the puncture angle is normal to the skin (+/−10 deg).

According to one embodiment, the mechanical extraction speed is 1 cycle per second or faster.

According to one embodiment, the punch is flushed via saline solution. It should be noted that saline may be used via the punch to flush it between one coring step to the other but also to reduce friction of cored tissue and internal the part of the punch during cores evacuation.

The imaging subsystem is provided with illumination means (e.g., emitters such as LEDs) to illuminate the field of view of the imaging subsystem and to keep the cameras of the imaging subsystem exposure time at low latency.

The LED’s wavelength is greater than 600 nm (warm white) to enable enough light to be reflected back from skin to cameras. Lower wavelengths tend to get absorbed more by human skin causing dark images.

The treated areas could be any of the body areas e.g., face, trunk, extremities, e.g., forehead, cheeks, jaw line, nose, forehead, neck, upper arms, thighs, buttocks and abdomen. According to another embodiment, the device of the present invention could be used for focal elimination of redundant dermal tissue for skin tightening, at least partially scar removal etc.

Post the coring process, the skin is tightened together by the stretching/compression device (as discussed hereinbelow) to promote healing thereof per the stretched/compressed tissue cores. According to one embodiment, the stretching/compression device is adhesive based (e.g., surgical wound closure tape or glue). It is noted that the operator is able to compress skin in different directions.

According to one embodiment of the present invention, the tensioning of the stretching/compression device, in order for it to effectively stretch the skin, has to be with pulling force of 20 $N/mm^2$-40 $N/mm^2$.

It should be noted that according to one embodiment of the present invention, the operator can define in the treatment plan at least one of the following:

entering patient information into database assigning surgery area and no-fly zones—where no treatment is provided to said area of skin tissue.

assigning areas with different densities assigning areas with different hole pattern assigning punch depth according to another embodiment of the present invention, adjustment of the treatment parameters could be enabled during treatment, in real-time; either manually, by the operator or automatically, by the system.

Figure 17:
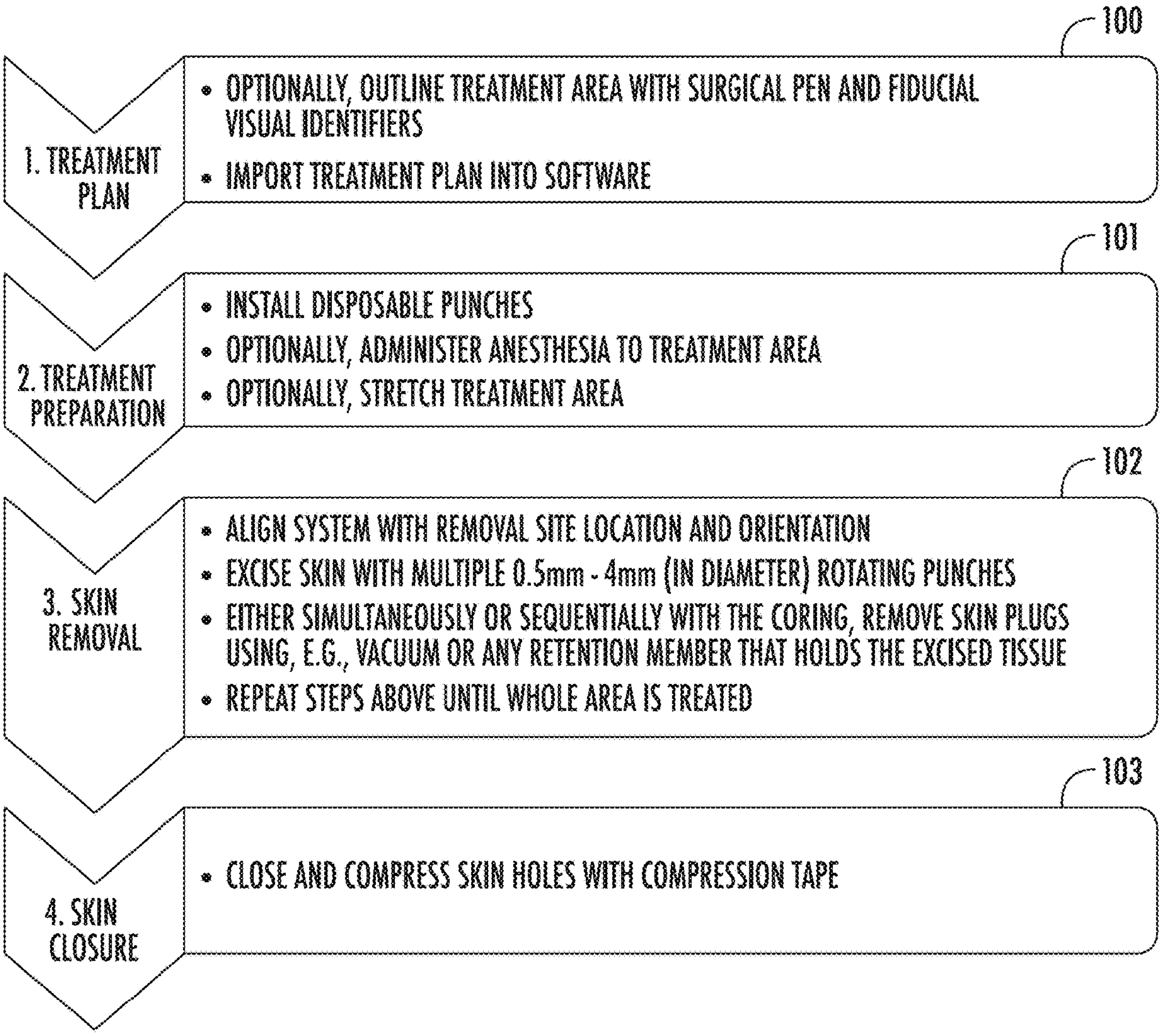
FIG. 17 illustrates the general operation of the device of the present invention.

Reference is now being made to FIG. 17 which illustrates the general operation of the device of the present invention.

The first, optional step, step 100, is to outline the skin treatment area with surgical pen and/or adhesive biocompatible fiducial markers visual identifiers.

An image of treatment area with surgical lines and fiducial markers is enough for treatment planning software to automatically recognize and reconstruct treatment zone in 3D software environment. Within treatment planning software operator selects desired areas with skin removal density between 5%-30% and skin tightening direction. Thus, Once the treated area is outlined, the treatment plan is finalized (as disclosed hereinafter) and is loaded onto the system.

It should be noted that it is optional that the patient is administered with local anesthesia to avoid any pain during the procedure.

In case of treatment of folded skin, the operator may stretch the treatment area by applying adhesive stretch tapes. Adhesive tapes (e.g., Tegaderm) put skin under tension by pulling away in preferred directions. It should be noted that it is important to first stretch the skin and only then to excise tissue portions. Otherwise, the skin, due to its flexibility might be caught in the internal area within the drilling means (the punches and/or the needles). Thus, according to one embodiment, a method of directional skin tightening by fractional treatment is provided by the following steps:

(i) producing a plurality of excised tissue portions in a region of skin tissue; and, (ii) securing at least one portion of a stretching/compression device (e.g., adhesive tapes Tegaderm), having at least two portions, to the skin region, adapted to provide contraction or expansion of said skin region in at least one predetermined direction;

(iii) applying tension therebetween said two portions thereby endorsing collagen growth and providing directional skin tightening in said region of skin tissue.

As disclosed above, in some cases (e.g., in case of loose skin), the step of securing said stretching/compression device to said skin region and application of tension (of either stretching or compression) to the skin is performed before said step of said producing a plurality of excised tissue portions in a region of skin tissue. This is to prevent any loosen skin being caught inside the drilling means (punches and/or needles).

According to another embodiment, the stretching/compression device is first stretched or compressed and only thereafter securing the second portion of said stretching/compression device to a different region of said skin.

According to another embodiment, the second portion of said stretching/compression device is secured to a different region of said skin.

According to another embodiment, applying tension therebetween said two portions additionally comprising step of securing the second portion of said stretching/compression device to said skin and pulling one portion relative to the other. As stated above, it is within the scope of the present invention when first the 2 portions of the stretching/compression device are secured to the skin, stretched and only thereafter the drilling means (the punches pr needles) provides a plurality of excised tissue portions.

It should be noted that even if the operator first applies tension therebetween the two portions of the stretching/compression device and only then produce a plurality of excised tissue portions in a region of skin tissue (while the tension is applied to the skin), it could very well be that the operator is required to apply additional tension therebetween the two portions of the stretching/compression device after the production of the excised tissue portions.

According to another embodiment of the present invention, it could be the said tension (stretching or compression) is applied simultaneously with the excision of skins portion by means of said drilling means (punches and/or needles).

The next step, step 101, is to install the disposable punches (and/or the needles) onto the device. The desired punches (and/or the needles) are selected depending on the desired density and depth of penetration.

Punches and/or the needles) are sharp, hollow and range from 0.4-4.0 mm in diameter. Larger hole may increase treatment speed but may not be appropriate for all skin types and body areas.

Optionally, a stopper is installed to limit maximum coring depth between 1-4 mm.

Next, step 102, the system is aligned with the area of the skin to be treated. Next, the skin is excised with multiple +/−0.4 to 4 mm (in diameter) punches (or needles).

According to one embodiment, the coring is performed by rotational movement of the punches (or needles), when the same are in contact with the skin. Alternatively, the coring is performed by rotational and translation movement of the punches (or needles).

Thereafter or simultaneously with the coring, the excised tissue is removed by means of vacuum (e.g., a negative pressure source). It should be noted that the system can utilize drilling means (e.g., a drill) that evacuate the skin plugs along with the drilling and, therefore, vacuum means are not needed. In that case at least one retention element (a retainer), integrated in the drilling means (the punches), is configured to hold the excised tissue (similarly to forceps), rendering the vacuum subsystem redundant. Thus, along with the drilling of the drilling means (the punches) performed into the skin, the retention element accumulates the excised skin plugs (tissue) and holds it. Thus, there is no need for application of suction as the suction's main rule is to evacuate the excised skin plugs (tissue). In particular, the at least one retention element may be implemented as a forceps-like device configured to exert pressure so as to hold the tissue.

Figure 34A:
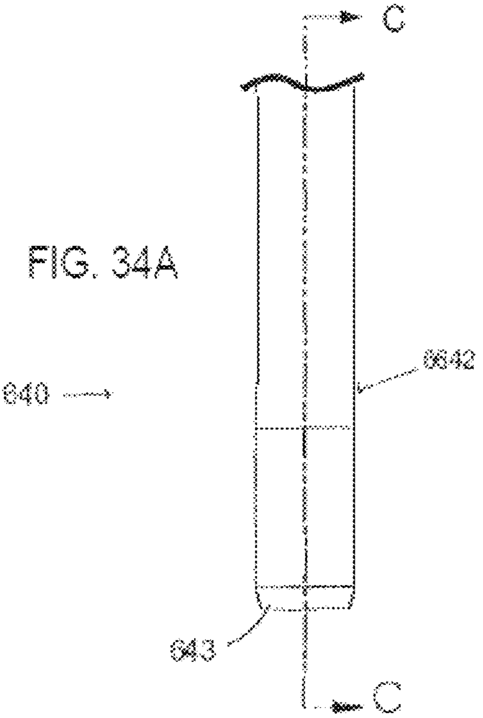
FIGS. 34A and 34B illustrate side and longitudinal views, respectively, of a biological unit removal tool having a movable retention member (retainer or retainer element) in the form of inner tines in a retracted or undeployed state.
Figure 34B:
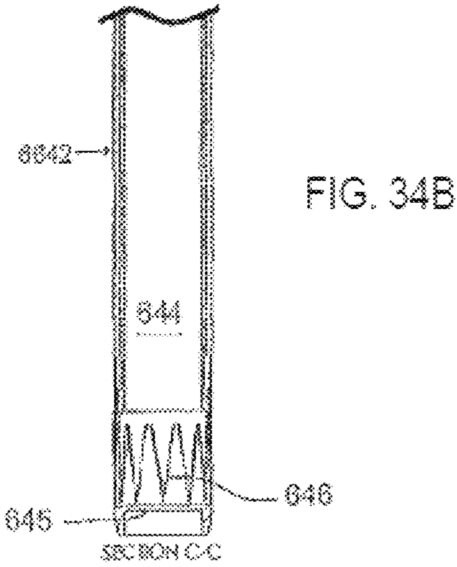
Figure 35A:
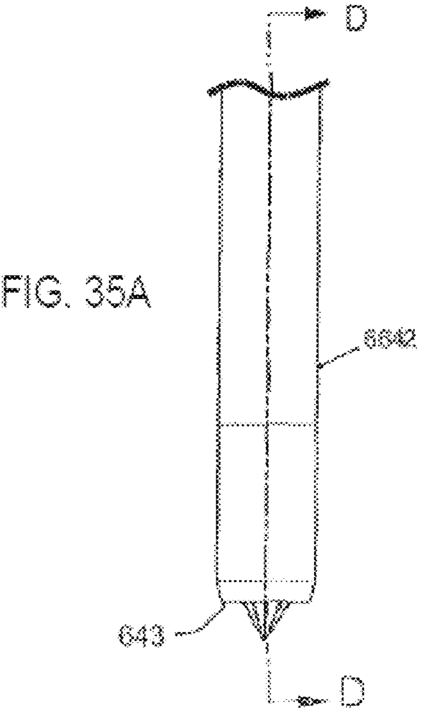
FIGS. 35A and 35B illustrate side and longitudinal views of the biological unit removal tool of FIGS. 34A and 34B in a retentive state.
Figure 35B:
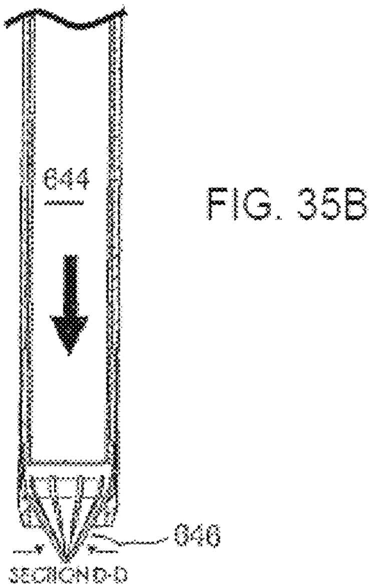

Exemplary implementations of the retention element are shown in FIGS. 34A and 34B, which depict side and longitudinal sectional views, respectively, of a biological unit removal tool having a movable retention member in the form of inner tines in a retracted or undeployed state. FIGS. 35A and 35B show the removal tool in a retention or deployed state. FIGS. 34A, 34B, 35A and 35D are exemplary depictions set forth in U.S. Pat. No. 8,696,686 issued Apr. 15, 2014, the entire contents of which are incorporated herein by reference, including for the apparatuses and methods disclosed therein. The exemplary removal tool 640 of FIGS. 34A, 34B, 35A and 35B has an outer tube or outer member 642 defining a lumen, and an inner tube or inner member 644 with a plurality of movable members or deformable tines 646 mounted on the inner tube. In the retracted position, the deformable tines 646 are flush with the inner diameter of the outer tube 642 and mounted to the distal end of the inner tube 644, which is allowed to move proximal/distal relative to the distal tip 643 of the outer tube. The distal tip 643 has a structure 645 that influences or guides the deformable tines to converge. The structure 645 is configured to assume the form of an inner ridge that guides the tines inward as the inner tube is advanced distally such that the tines converge. Alternatively, the structure may take the form of a taper, a step, an incline or any other form that guides the deformable tines to coapt. In the retention position, at least a portion of the retention member, e.g., the deformable tines, extend beyond the distal tip of the outer elongated member 642. The inner tube with tines may be made of various materials, including shape memory materials, for example, Nitinol, or Elgiloy, or cobalt chromium, or similar material which accommodates repetitive bending without fatigue (or with more tolerant fatigue properties), if desired, at the base of the tines. In some embodiments, the movable retention members need not be in the form of tines, but may be configured as thin wires, filaments, or paddle shaped structures for example, or varying shapes and surface finishes, and of various circumferential distributions.

The drilling means (the punches, microneedles) tools generally have a tubular elongated body with a cylindrical profile and a hollow lumen therethrough. According to one embodiment, at least one retention member described herein may be positioned not only at the distal portion of the drilling means, but also in various locations along the body of the drilling means, for example, a short distance from the distal end, or midway along the body of the drilling means, depending upon the configuration of the drilling means and its intended purpose. The terms "coupled," or "attached," or "connected," or "mounted" as used herein, may mean directly or indirectly coupled, attached, integrated, or mounted through one or more intervening components.

A "retention member" as used herein refers to a structure, or a mechanism, or a number of structures and/or mechanisms that partially or fully retain a biological tissue in a lumen of the drilling means. The retention member may translate into or across the lumen, or radially constrict the lumen in a circumferential manner, for example, simply closing tightly about the tissue, located in the lumen to improve its retention and removal. The retention members described herein may be made of a variety of biocompatible materials, such as polypropylene, polyester, polyurethane, Teflon, Nitinol, stainless steel, etc. The configuration of the retention members may be solid, braided, filamentous, etc., and should not be considered limited to any one particular embodiment.

According to one embodiment the retention member may be movable along an axis of the drilling means (the punches). The retention member may form an integral part of the elongated body or may comprise a separate element attached within the lumen of the elongated body of the drilling means (the punches). In another version, the retention member comprises a portion made of a deformable material and the tool further comprises an actuation device adapted to deform at least the deformable portion of the retention member and constrict a lumen defined therein. For instance, the retention member comprises a plurality of portions made of deformable material, each two being separated by a spacer made of a substantially rigid material, such as Teflon, stainless steel, or titanium. The deformable material may be selected from the group consisting of silicone, rubber, gels, and fluids.

Another aspect of the invention is a biological tissue removal tool (that renders the use of suction redundant) comprising at least one movable retention member in communication with the drilling means (the punches). At least one of the drilling means (the punches) has a lumen sized to receive a biological specimen and a distal tip configured to penetrate a body surface. The retention member moves with respect to the drilling means (the punches) between a retracted position and a retention position in which the retention member is configured to project into or across the drilling means (the punches) proximally to the distal tip so as to impede movement in a distal tip direction of the biological specimen received in the lumen.

The retention member may be located and moveable from outside the drilling means (the punches) into the same. In one embodiment, the retention member is spring-biased, such as torsionally spring-biased, into the retention position. In another form, the retention member slides axially over the drilling means (the punches) between the retracted and retention positions and has a portion that passes into the drilling means (the punches) through an aperture in a wall of the elongated body in the retention position. For instance, the retention member may be a clip having at least two portions passing into the lumen through diametrically opposed apertures in the wall of the drilling means (the punches). In some alternatives, an actuator displaces the retention member between the retracted and retention positions, and the actuator may be automated. The retention member may be rotatable between the retracted and retention positions.

Another example of the at least one movable retention member is as follows. At least a portion of the retention member is axially movable over the drilling means (the punches) and the retention member is radially movable between a retracted position and a retention position, such that in the retention position at least a distal tip of the retention member extends beyond the distal tip of the drilling means (the punches) and converges.

It should be noted that the coring instrument could comprise several microneedles (punches) or a single one. It should be further noted that each of which could be independently operated or a sub-group thereof could be operated simultaneously. As stated above, before the coring step, the system aligns the punch (or punches) substantially perpendicular to the skin.

According to one embodiment there is provided at least one punch (or needle). Alternatively, at least 5 punches (or needles) are provided. The punches (or needles) could rotate together, or each, individually. According to one embodiment all punches (or needles) are coupled to one common shaft operated by an electric DC motor. According to another embodiment, there are multiple shafts operated by several electric DC motors.

According to one embodiment, the coring RPM is between 1000-7000 RPM.

As disclosed hereinafter the dissected skin cores from each punch/needle are pulled up by e.g., vacuum or any retention element(s), which can be, e.g., integrated within the punches, into accumulation chamber and eventually through tubing into canister for disposal. To ensure there are no clogs in tubing, liquid (e.g., saline) may be added to the chamber via a dripping mechanism (a liquid supply) to flush the system from at least one of the punch's end.

The vision subsystem, pointed at where punch tips will extend, detects 3D location of the skin surface and aligns punch (or punches) perpendicularly to the skin plane using moving arm joints. 3D Vision subsystem uses either passive (e.g., 2 cameras) or active (e.g., 2 cameras and an infrared laser projector) stereo vision approach for sub millimeter accuracy.

Once aligned, the system translates a rotating punch (or punches) to patient skin at high speed. Once the punch (or punches) approximate the skin they slow-down to a slower speed and then they will penetrate into the skin to 1-6 mm coring depth. For example, a conveyor or other mechanism such as a mover or adjustment arm may be used to move the punches to advance them toward the skin.

While inside the skin, the punch (or punches) use rotation sheer force to fracture and core out skin without compressing skin away from punch tips. Additionally, to avoid unnecessary skin compression, the system uses closed loop force sensor and vision feedback to determine when the punches break tougher epidermis layer and when the punches reach desired depth in dermis.

It is emphasized that, according to one embodiment of the present invention, before the treatment, a stretching element (e.g., Tegaderm) is used to stretch the affected skin (or its surroundings) before skin before coring and thereby to stabilize the skin (so as to prevent compression before the coring).

At the end of the cycle, the system opens vacuum line to pull up and remove dermal tissue core. Next, the punch (punches) are pulled back up above skin. Alternatively, the system may include at least one retention element adapted to hold or contain the extract excised tissue (without any applied vacuum).

According to one embodiment, the system can use automation and artificial intelligence algorithms to repeat and deliver described coring procedure according to the treatment plan rules. It should be noted that the artificial intelligence is used also to determine the treatment plan and coring protocol (e.g., the pattern of the coring elements).

Each coring cycle creates at least 1 hole; more preferable, 6 holes. Automation arranges and packs the holes patterns to achieve planned density.

By tracking unique fiducial identifiers system remembers where previous holes have been made therefore preventing possibility of overlapped holes. In addition, treatment automation deals with dynamic elements not captured in the treatment plan such as no-go zones, surgical equipment obstructions, bleeding etc.

The final step, step 103, is the directional tightening; in which the skin is compress, at the desired direction, by means of the compression tape (as disclosed hereinafter).

The Treatment Plan

Before using the device of the present invention, an operator will outline the treatment area to be tightened on patient's skin. The operator marks treatment area using surgical pen and/or adhesive biocompatible fiducial markers.

An image of treatment area with surgical lines and fiducial markers is enough for treatment planning software to automatically recognize and reconstruct treatment zone in 3D software environment. Within treatment planning software operator selects desired areas with skin removal density between 5%-30% and skin tightening direction.

Depending on desired density, coverage rate and depth, the operator selects appropriate disposable punches. It should be noted that according to one embodiment of the present invention, the appropriate disposable punches are automatically recommended by the system (based on the treatment parameters; e.g., skin type, lesion to be treated, desired skin removal density etc.).

The punches (micro needles) are sharp, hollow and range from about +/−04-4.0 mm in diameter. Larger hole may increase treatment speed but may not be appropriate for all skin and lesion types. A typical coring depth would be between about 1 to about 4 mm.

The system of the present invention is positioned and orientated over patient skin either by operator manually, or automatically by finding treatment zone using vision subsystem. Vision system registers treatment zone with treatment plan by searching for particular fiducial identifiers or colored lines on the skin.

The Coring Instrument and the Skin Removal Sub-System

Figure 18:
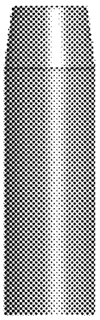
FIG. 18 illustrates a dermal micro-coring process using a single punch.

Instrument performs dermal micro-coring process using multiple hollow rotating sharp punches. Each punch, shown on FIG. 18 has cylindrical shape with sharp conical cutting tip at the top. To ensure full dissection each punch has sharp inner edge and outside bevel. It should be noted that any other cross section area of the punch would work as well.

According to one embodiment of the present invention, there are X simultaneously rotating punches. X is in the range of 3-7. According to one embodiment, all punches rotate together and coupled to one common shaft operated by electric DC motor. According to another embodiment, each punch rotates individually and may or may not be coupled to one common shaft operated by electric DC motor.

Reference is now made to FIGS. 19A-19D, illustrating the distal end of the applicator have 7 punches, 6 cerebralized around a $7^{th}$ punch.

Figure 19B:
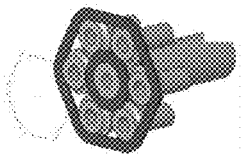
FIGS. 19A, 19B, 19C, 19D and 19E illustrate two possible punch rotation drive types: belt driven and friction driven.
Figure 19A:
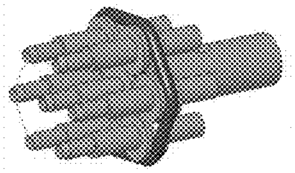
Figure 19D:
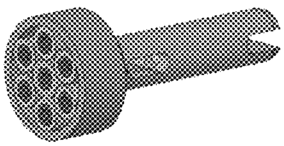
Figure 19C:
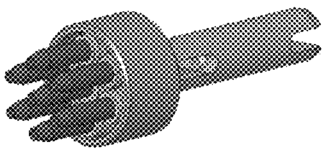

FIGS. 19A-19D illustrate two possible punch rotation drive types: belt driven and friction driven. FIGS. 19A-19B illustrates the belt driven punch rotation type, before and after activation thereof, respectively. FIGS. 19C-19D illustrates the friction driven punch rotation type, before and after activation thereof, respectively.

Figure 19E:
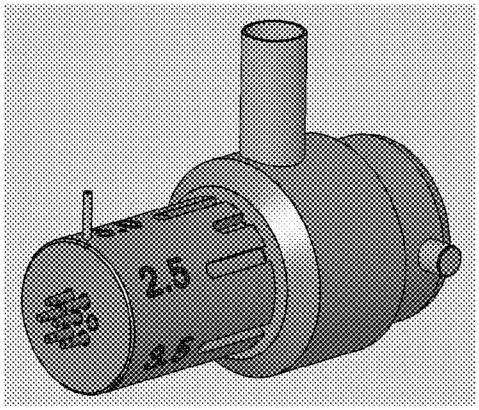

Reference is now made to FIG. 19E, illustrating another embodiment of the distal end of the applicator have 6 punches (and not 7, as illustrated in FIGS. 19A-19D). As seen in FIG. 3E, the six micro-coring needles are arranged in 2 groups of 3 micro-coring needles, each arranged in vertices of a horizontally lying 'V' pattern. Namely, in a pattern of '>>'. It should be noted that it is within the scope of the present invention where the six micro-coring needles (the punches) are arranged in at least two horizontally lying 'V' shape, oppositely facing, namely, in a pattern '><'. However, one skilled in the art would appreciate that any pattern could be used. e.g., the pattern of the micro-coring needles (the punches) could be selected from a group consisting of a circular, hexagon, rectangular, square and any combination thereof.

The coring RPM is between 1000-7000 RPM. Punches can translate together back and forth on a leadscrew or using robotic arm itself.

Figure 20:
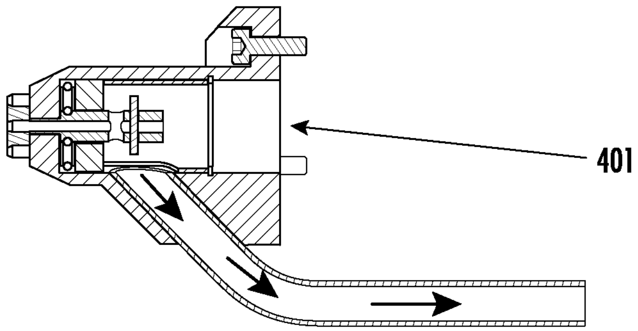
FIG. 20 illustrates the dissected skin cores from each punch are pulled up by vacuum

The punches are connected to skin core accumulation chamber. Dissected skin cores from each punch are pulled up by vacuum (see arrows 401) into accumulation chamber and eventually through tubing into canister (not shown) for disposal (see FIG. 20). It is noted that, as an alternative to the vacuum, the system may include at least one retention element adapted to hold or contain the extract excised tissue (without any applied vacuum). To ensure there are no clogs in tubing, liquid (e.g., saline) may be added to the chamber via a dripping mechanism to flush the system.

According to another embodiment, the liquid (e.g., saline) is added to reduce friction during the coring step.

Figure 21A:
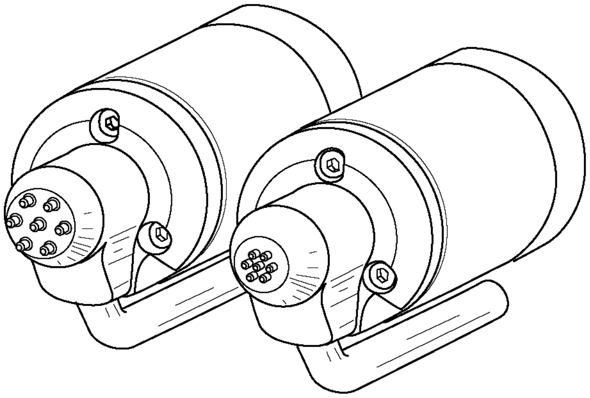
FIGS. 21A-21B illustrate one arm, each of which utilizes 1 or more punches, as embodied in the system.

According to one embodiment of the present invention, only one arm with 1 or more punch (or punches) is utilized in the system. According to another embodiment of the present invention, more than one arm, each of which utilizes 1 or more punch (or punches) is embodied in the system (as illustrated in FIG. 21*a*). In such an embodiment, each arm could utilize 1 or more punch (punches) with the same properties (width, depth, cross section etc.) or alternatively, each arm would enclose one or more punch (or punches), each (or all) with individual/distinct properties.

According to another embodiment, each arm (and punches thereof) is characterized by different properties (e.g., width, depth, cross section of the punches, translation speed, rotation speed etc).

According to another embodiment, all arms may comprise the same mechanism; alternatively, each arm comprises a different mechanism, e.g., different incision/excision means (e.g., one arm is configured as a cutter to make an incision and second arm is configured as an injector to be used for seeding or insertion/injection of additives, as disclosed hereinafter (e.g., threads, hyaluronic acid etc.)).

According to another embodiment of the present invention each punch is activated independently. Such that it could be that in the at least one arm of the device, there are several punches. However, each would be operated individually; thus, the operator may activate only a few of the punches and not all.

Figure 21B:
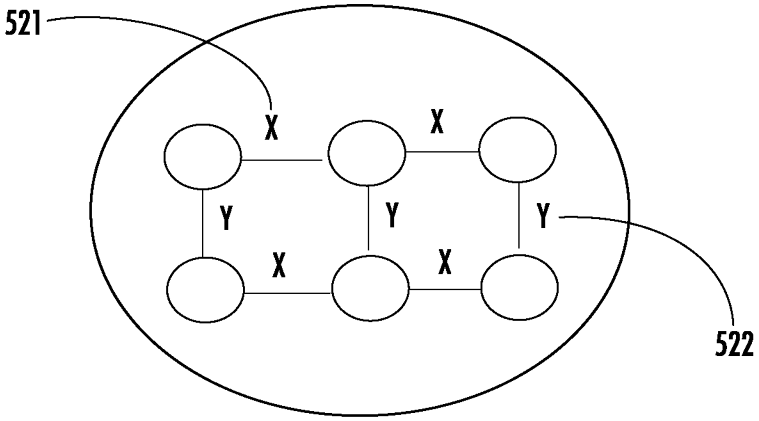

According to another embodiment of the present invention, the distance between each punch could be adjusted. Ref is now made to FIG. 21*b*, which illustrates one arm 510 of the device having 6 punches 520, space apart at a first distance X (see numerical ref. 521) and a second distance Y (see numerical ref. 522) from each other. According to one embodiment, said first distance X and second distance Y are adjustable such that the distances between the punches are changeable to better adjust thereof to the treatment.

Automation and Artificial Intelligence Algorithms

According to one embodiment, the system uses automation and artificial intelligence algorithms to analyze the mechanical visualization input and to determine and establish the most appropriate coring pattern and plan. Thereafter, the artificial intelligence instructs to repeat and deliver described coring procedure according to the treatment plan rules.

Figure 22:
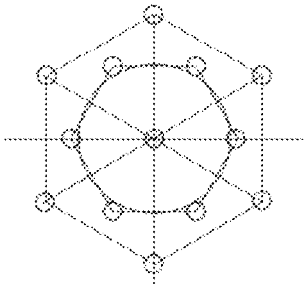
FIG. 22 illustrates a top views of the punches.

According to one embodiment, each coring cycle creates 6 holes arranged hexagonally (as illustrated in FIG. 22). Care should be given to the fact that there can be any number of punches. 6 is merely an example.

Figure 24:
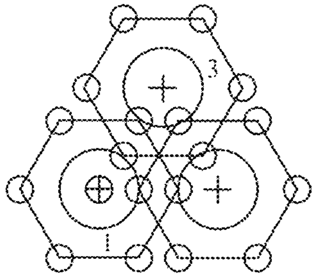
Figure 25:
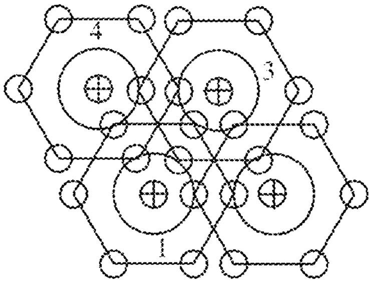

Automation arranges and packs hex patterns to achieve planned density. For example, on FIGS. 23-25, one instrument design may spread out punches allowing overlapping patterns, while another design may have punches packed tightly together. By tracking unique fiducial identifiers system remembers where previous holes have been made therefore preventing possibility of overlapped holes. In addition, treatment automation deals with dynamic elements not captured in the treatment plan such as no-go zones, surgical equipment obstructions, bleeding etc.

According to one embodiment, the overlapping patterns could have at least one point of excised tissue portion.

According to another embodiment, the device of the present invention also provides a mechanism (e.g., a stepper) configured to step a micro-coring punch and locate the micro-coring punch such that one element selected from a group consisting of vertex, facet and any combination thereof of a stepped micro-coring punch hexagon is overlapped with (e.g., crosses or intersects) one element selected from a group consisting of vertex, facet and any combination thereof of a first micro-coring punch hexagon. In some embodiments, a step mechanism is implemented as a stepper that translates the positions of the punches such that after a first coring session, the location of the punches is moved for a next coring session.

Figure 23:
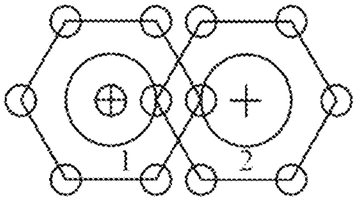
FIGS. 23-25 illustrate one instrument design may spread out punches allowing overlapping patterns.

According to another embodiment, there can be an overlap between one coring step to the other (e.g., by vertex or facet); and, according to another embodiment of the present invention there can an overlap between consecutive coring steps (i.e., as can be seen in FIG. 23).

According to another embodiment of the present invention, the system utilizes artificial intelligence and/or mechanical visualization, OCT, Ultrasound, machine learning algorithms and/or image processing to provide inform decision as to the coring location. In other words, the system first scans the tissue to be treated and by means of at least one selected from a group consisting of artificial intelligence, mechanical visualization, OCT, Ultrasound, machine learning algorithms, image processing and any combination thereof, the system decides where it would be most beneficial to perform the coring.

Directional Tightening

At the end of the treatment, the operator will use a stretching/compression device, e.g., a tensioner, to close holes in the skin and promote healing per the new dimensions of the cored area, as employed by e.g., the compression.

According to one embodiment of the present invention, the stretching/compression device is an elastic compression tapes to close holes in the skin. Compressing skin together enables wound healing and collagen accumulation and adherence of the cored walls per its modified (compressed) configuration. Accordingly, with compression, cored holes are not as circles anymore, but ellipsoid and configured to be stabilized by new collagen in that position, promoting healing with the result of in aesthetic skin tightening results due to the accumulated compressed cores per axis (with less chance of scars). The stretching/compression device disclosed herein creates compression on the internal area and tension on the external area and eliminates unwanted puncture scars.

According to one embodiment of the present invention, the tension applied can be adjusted based on skin type to produce best results.

Reference is now made to FIGS. 26*a*-26*b* illustrating one embodiment of the stretching/compression device 200, where FIG. 26A1 shows a top view of the device 200 in an unassembled state, FIG. 26A2 shows a top view of the device 200 in an assembled state, FIG. 26A3 shows a bottom view of the device 200 in an assembled state. FIG. 26B shows an exploded perspective view of the device.

According to this embodiment of the present invention, the stretching/compression device 200 has a long portion 205 and a short portion 210. The short portion 210 comprises at least one buckle-like element having at least one slot hole 215 therewithin. The long portion 205 is adapted to be connected to the short portion 210 through said at least one slot hole 215 therewithin. The long portion 205 is threaded through said slot 215 and secured to the short portion 210 (as detailed hereinbelow). Said securement of said long portion 205 to said short portion 205 is by means of attaching (e.g., by a fastener) at least one adhesive layer in said long portion 205 to at least one adhesive layer in said short portion 210.

Figure 27:
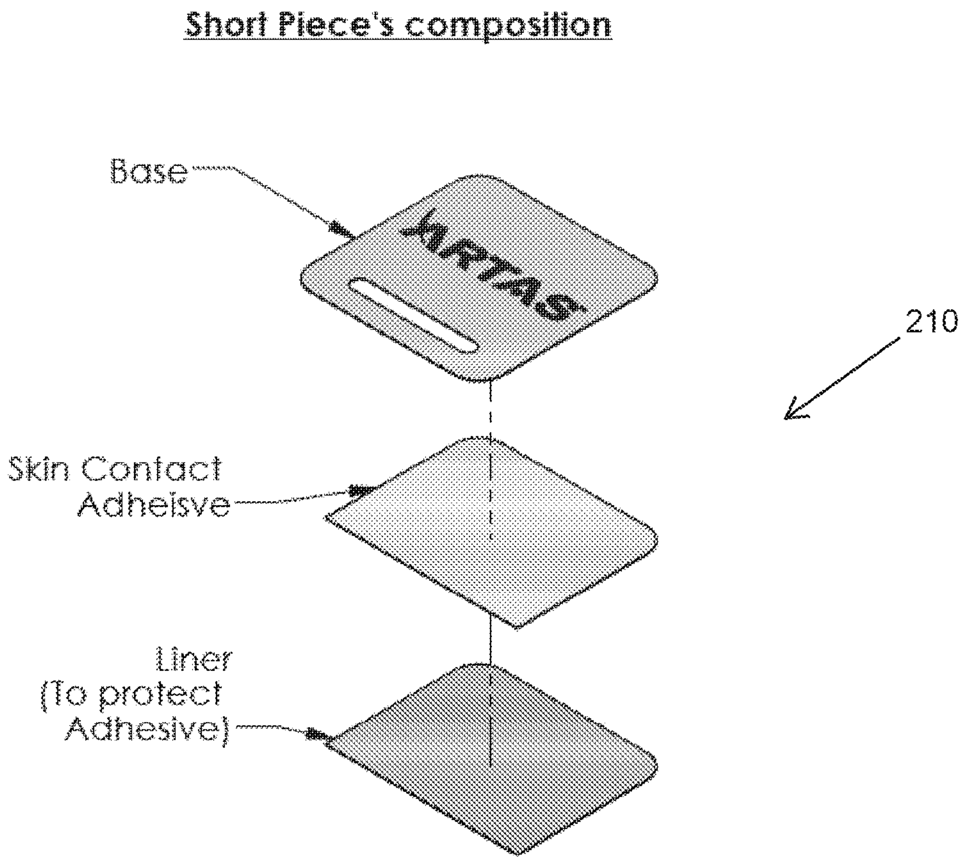
Figure 28A:
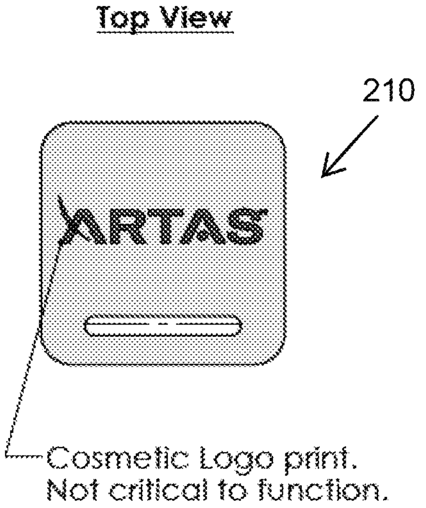
FIG. 28A shows a top view of the short portion.
Figure 28B:
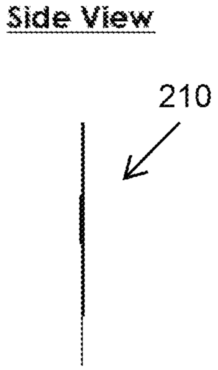
FIG. 28B shows a side view of the short portion.
Figure 28C:
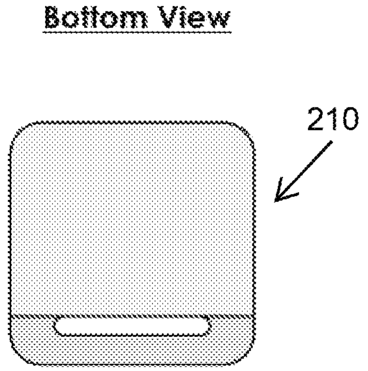
FIG. 28C shows a bottom view of the short portion.

Reference is now made to FIGS. 27-28 illustrating the short portion 205, according to this embodiment, of the stretching/compression device 200, with FIG. 28A showing a top view of the short portion 210, FIG. 28B showing a side view of the short portion 210, and FIG. 28C showing a bottom view of the short portion 210. According to this embodiment, the short portion has a base, an adhesive, and a liner.

The base can be made from any material that is strong enough to withstand, for example, 10 PSI in shear force.

The adhesive can be made from any material that is strong enough to withstand, for example, 10 PSI in shear force and the adhesive should adhere to skin well.

The liner is a cover that protects the adhesive until it is to be used.

Figure 29:
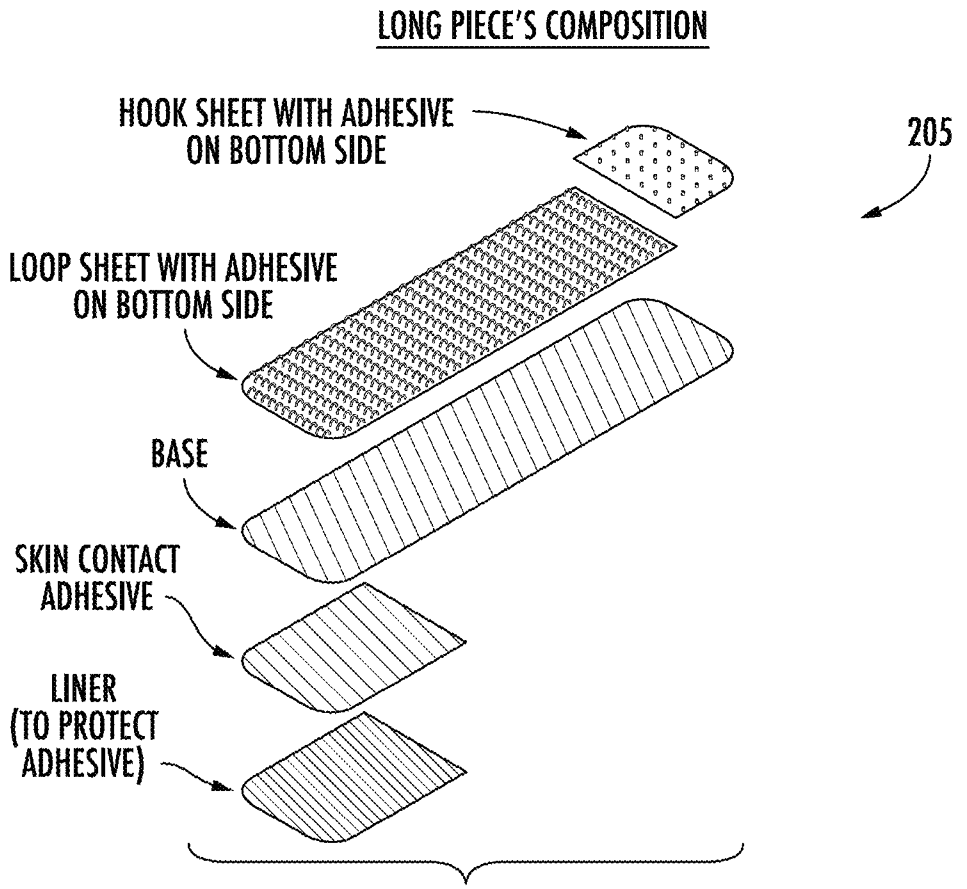
Figure 30A:
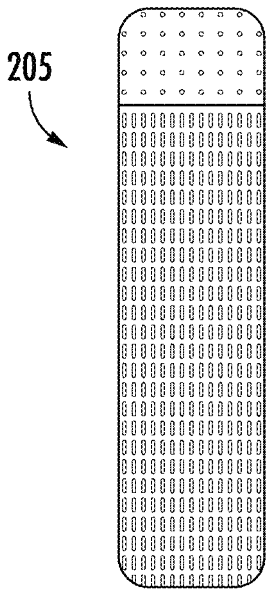
FIG. 30A shows a top view of the long portion.
Figure 30B:
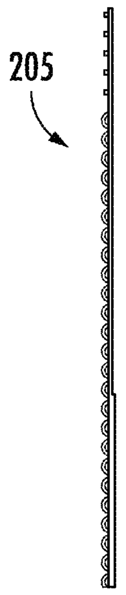
FIG. 30B shows a wide view of the long portion.
Figure 30C:
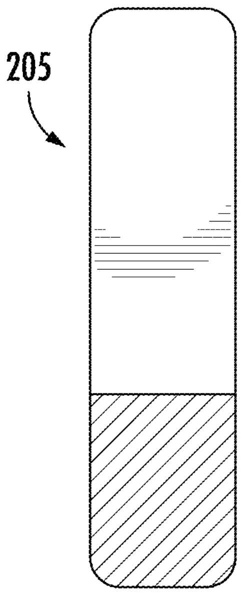
FIG. 30C shows a bottom view of the long portion.

Reference is now made to FIGS. 29-30 illustrating the long portion 205, according to this embodiment, of the stretching/compression device 200, with FIG. 30A showing a top view of the long portion 205, FIG. 30B showing a wide view of the long portion 205, and FIG. 30C showing a bottom view of the long portion 205.

According to this embodiment, the portion 205 has a base, an adhesive, a liner, and hook & loop sheets.

The base can be made from any material that is strong enough to withstand, for example, 10 PSI in shear force.

The adhesive can be made from any material that is strong enough to withstand, for example, 10 PSI in shear force and it should adhere to skin well.

The liner is a cover that protects the adhesive until it is to be used.

According to one embodiment, the hook and loop component (e.g., sheet) is Velcro. In an example, the hook sheet is the male side where it has tiny semi-rigid hooks on the top side and the loop sheet is the female side where it has thin loops on the top side. When the hook top side and loop top side come in contact with each other, the hooks hook onto the loops.

On the bottom side of both sheets, there is adhesive to allow the sheets to adhere to the base. This is not always necessary. An alternative is that the sheet acts as the base layer if the sheet is strong enough.

According to one embodiment, the loop sheet covers most of the long portion 205 interface. This allows for smooth tape movement since the loop sheet may be thinner than the hook sheet. It is possible to reverse this; the hook sheet covers most of the long portion 205, but the hook sheet should be thin enough to be flexible enough to fold over (see side view note).

Once the stretching/compression device 200 is placed over the holes in the skin, the operator stretches the same to create compression and/or tension to the desired level. Once the desired tension level is reached, the stretching/compression device can be closed and secured.

The application of the stretching/compression device 200 will result in direction tightening of the skin.

The directionality of the skin region to which the stretching/compression device 200 is applied, can also be optimized. In particular embodiments, the direction of skin tightening is determined by the directionality of the tensile force or compressive force being applied. It can be in the x-, y-, and/or z-direction with respect to the device 200 or skin region.

The optimization of the applied tension of the stretching/compression device 200 can provide numerous benefits. For instance, such tunability can allow real-time control of compressing and/or expanding the stretching/compression device after affixation thereof to the skin. This level of control can allow for personalized treatment of the patient based on the disease, disorder, or condition to be treated; the optimal cosmetic effect to be achieved; the optimal closure process to be achieved; and/or the timing and extent of the healing process observed for the particular patient. Furthermore, tunability can allow for less discriminate control over how the incisions or excisions in the skin region are made, as well as more discriminate control over selectively closing or opening the incisions or excisions.

The stretching/compression device 200 can be affixed to the entire treated skin region or in a portion of the treated skin region. Directional or non-directional tightening can be achieved by producing a geometric arrangement of incisions and/or excisions that are treated similarly. Alternatively, such tightening can be achieved by a non-geometric arrangement of incisions and/or excisions in which only some of the incisions and/or excisions are opened or closed using the stretching/compression device 200.

It should be noted that when an incision or excision occurs, the wound healing process starts and, as commonly known, includes collagen synthesis and maturation. Thus, it is within the core of the present invention to facilitate its construction and accumulation per deformed cored area(s).

The tunable dressing can include an adhesive layer (e.g., formed from any adhesive material described herein). The adhesive layer can be continuous (i.e., a continuous layer of one or more adhesive materials attached to the proximal surface of a dressing) or discontinuous (i.e., a non-continuous layer of one or more adhesive materials attached to the proximal surface of a dressing). The adhesive layer can include any useful arrangement of the adhesive material. For instance, the adhesive layer can be tunable and allows for controlled compression or expansion. In some embodiments, an adhesive layer includes a random, non-geometric, or geometric array of an adhesive material for tunability. In particular embodiments, the array allows for directional or non-directional compression and/or expansion as the dressing compresses and/or expands. In particular embodiments, the adhesive layer is discontinuous and includes an array of an adhesive material (e.g., an array of dots, where each dot gets closer together as the dressing compresses and each dot gets further apart as the dressing expands). Exemplary adhesive materials are described herein and include materials that promote collagen cross-linking, such as riboflavin or Rose Bengal, synthetic glues (e.g., cyanoacrylate, polyethylene glycol, or gelatin-resorcinol-formaldehyde), or biologic sealants (e.g., albumin-based or fibrin-based sealants that promote clotting).

The stretching/compression device 200 can also include at least one occlusion layer (e.g., to control humidity and/or promote wound healing), at least one absorption layer (e.g., to absorb wound exudate), at least one reinforcement layer (e.g., to reinforce the layer and optionally formed from low-density polyethylene (LDPE), fluorinated ethylene propylene (FEP), or nylon), and/or at least one delivery layer (e.g., to delivery one or more therapeutic agents to enhance treatment thereof).

The stretching/compression device 200 can be of any cosmetically appealing color, shape, and/or material. For example, the stretching/compression device 200 can be provided in a skin tone color or is transparent or semi-transparent. Such transparent or semi-transparent dressings can additionally be helpful for visualization, e.g., for real-time tunability of the dressing and/or for affixing the stretching/compression device 200 to the treated skin region. According to another embodiment of the present invention, the stretching/compression device 200 could either first be applied (i.e., secured) to skin (post excision of the skin portion) and only thereafter application of tension forces are applied thereto to provide the directional tightening of the skin.

According to another embodiment of the present invention, the stretching/compression device 200 could either first be stretched and only then applied (i.e., secured) to skin (post excision of the skin portion). Once applied when the same is stretched the stretching/compression device 200 (as it is an elastic dressing) would compress back to its original shape and hance apply compression tension to the skin thereto to provide the directional tightening of the skin. In other words, the stretching/compression device 200 could first go through a pretreatment, where stretching forces are applied thereto (for example by means of a dedicated device) and, once it is fully/partially stretched it is applied to the skin.

According to another embodiment of the present invention, the stretching/compression device 200 that can be employed is simply a fastener such as an adhesive tape, e.g., 3M™ Tegaderm™, HP Transparent Film Dressing (see, e.g. 3M Tegaderm HP Transparent Film Dressing, as show on 3M US website).

Methods of Skin Tightening, More Specifically Direction Skin Tightening

The present invention relates to various methods and devices (e.g., the stretching/compression device) used to selectively open or close incisions and/or excisions (e.g., all or a portion of such incisions, such as microslits, and/or excisions, such as holes) formed in the skin region by the incised or excised tissue portions. The devices can be affixed to the entire treated skin region or in a portion of the treated skin region, which allow for directional or non-directional tightening by producing a geometric or non-geometric arrangement of incisions and/or excisions that are treated similarly or differently. Further, the devices can provide uniform or non-uniform compression and/or expression across the entire device or a portion thereof. Accordingly, these methods and devices can result in reducing the skin surface and/or tightening of the skin.

The methods can include contraction or expansion in one or more directions in at least a portion of the device (e.g., the dressing). The methods include, for example, affixing the stretching/compression device to a skin region having a plurality of incised tissue portions and/or excised tissue portions (e.g., where at least two of said tissue portions has at least one dimension that is less than about 1 mm or an areal dimension that is less than about 1 $mm^2$). The device provides contraction or expansion of the skin region in one or more directions (e.g., in the x-, y-, z-, xy-, xz-, yz-, and/or xyz-directions, as described herein), where such contraction or expansion can be uniform or non-uniform. Furthermore, contraction or expansion arises by exposing an affixed device to one or more external stimuli (e.g., any described herein) that results of application of force (e.g., compression or stretching forces) on the stretching/compression device. In addition, such contraction and/or expansion can be adjusted after affixing the device. For example, after treating the skin and affixing the device, the device can be further expanded or to compress the skin region. In this manner, the device is tunable/adjustable.

The present invention also includes methods of tightening skin in a preferred direction (directional tightening of the skin (e.g., by compression and/or expansion exerted by the device)).

The present invention also includes optimizing the dimension of the incised or excised tissue portions to promote wound healing. Exemplary dimensions include circular and non-circular holes, such as elliptical holes. Non-circular holes can be formed by using an apparatus having a non-circular cross-section (e.g., a blade or a tube, such as a hollow tube, having a non-circular cross-section) or by pre-stretching the skin before treatment with an apparatus having a circular cross-section (e.g., a circular coring needle generates an elliptical hole in a non-stretched skin). In some embodiments, the long axis of the ellipse is perpendicular to the pre-stretching direction, where the elliptical hole can generate skin tightening preferentially in the direction of the short axis of the ellipse. Accordingly, the stretching/compression device can be affixed to a skin portion including one or more holes or one or more incised or excised tissue portions having one or more geometries.

In some embodiments, the long axis of the ellipse is perpendicular to the pre-stretching direction, where the elliptical hole can generate skin tightening preferentially in the direction of the short axis of the ellipse. Accordingly, the stretching/compression device can be affixed to a skin portion including one or more holes or one or more incised.

Adhesive Materials that can be Integrated in the Stretching/Compression Device.

An adhesive can be used within the dressing (e.g., as in the adhesive layer) or used in combination with any method described herein to promote skin tightening.

The adhesive can be a pressure-sensitive adhesive (PSA). The properties of pressure sensitive adhesives are governed by three parameters, tack (initial adhesion), peel strength (adhesion), and shear strength (cohesion). Pressure-sensitive adhesives can be synthesized in several ways, including solvent-borne, water-borne, and hot-melt methods. Tack is the initial adhesion under slight pressure and short dwell time and depends on the adhesive's ability to wet the contact surface. Peel strength is the force required to remove the PSA from the contact surface. The peel adhesion depends on many factors, including the tack, bonding history (e.g. force, dwell time), and adhesive composition. Shear strength is a measure of the adhesive's resistance to continuous stress. The shear strength is influenced by several parameters, including internal adhesion, cross-linking, and viscoelastic properties of the adhesive. Permanent adhesives are generally resistant to debonding and possess very high peel and shear strength.

Exemplary adhesives include a biocompatible matrix (e.g., those including at least one of collagen (e.g., a collagen sponge), low melting agarose (LMA), polylactic acid (PLA), and/or hyaluronic acid (e.g., hyaluranon); a photosensitizer (e.g., Rose Bengal, riboflavin-5-phosphate (R-5-P), methylene blue (MB), N-hydroxypyridine-2-(1H)-thione (N-HTP), a porphyrin, or a chlorin, as well as precursors thereof); a photochemical agent (e.g., 1,8 naphthalimide); a synthetic glue (e.g., a cyanoacrylate adhesive, a polyethylene glycol adhesive, or a gelatin-resorcinol-formaldehyde adhesive); or a biologic sealant (e.g., a mixture of riboflavin-5-phosphate and fibrinogen, a fibrin-based sealant, an albumin-based sealant, or a starch-based sealant). In particular embodiments, the adhesive is biodegradable. Exemplary pressure-sensitive adhesives include natural rubber, synthetic rubber (e.g., styrene-butadiene and styrene-ethylene copolymers), polyvinyl ether, polyurethane, acrylic, silicones, and ethylene-vinyl acetate copolymers. A copolymer's adhesive properties can be altered by varying the composition (via monomer components) changing the glass transition temperature (Tg) or degree of cross-linking. In general, a copolymer with a lower Tg is less rigid and a copolymer with a higher Tg is more rigid. The tack of PSAs can be altered by the addition of components to alter the viscosity or mechanical properties. Exemplary pressure sensitive adhesives are described in Czech et al., "Pressure-Sensitive Adhesives for Medical Applications," in Wide Spectra of Quality Control, Dr. Isin Akyar (Ed., published by InTech), Chapter 17 (2011)).

In one exemplary technique, a photosensitizer is applied to the tissue (e.g., Rose Bengal (RB) at concentration of less than 1.0% weight per volume in a buffer, e.g., phosphate buffered saline to form a skin tissue-RB complex), and then the tissue is irradiated with electromagnetic energy to produce a seal (e.g., irradiated at a wavelength of at least 488, at less than 2000 $J/cm^2$, and/or at less than 1.5 W/cm<2>, e.g., about 0.6 W/cm<2>). This exemplary technique is described in U.S. Pat. No. 7,073,510, which is incorporated by reference in its entirety. In another exemplary technique, a laser can be used for tissue welding. In yet another exemplary technique, a photochemical agent is applied to the tissue, and then the tissue is irradiated with visible light to produce a seal.

According to one embodiment of the present invention, therapeutic agents can be integrated within the stretching/compression device to be released to the skin's holes to accelerate healing thereof. Exemplary agents include one or more growth factors (e.g., vascular endothelial growth factor (VEGF), platelet-derived growth factor (PDGF), transforming growth factor beta (TGF-β), fibroblast growth factor (FGF), epidermal growth factor (EGF), and keratinocyte growth factor); one or more stem cells (e.g., adipose tissue-derived stem cells and/or bone marrow-derived mesenchymal stem cells); steroids (for example, steroids to prevent edema), agents which prevent post-inflammatory skin hyperpigmentation (e.g., hydroquinone, azelaic acid, kojic acid, mandelic acid, or niacinamide); one or more analgesics (e.g., paracetamol/acetaminophen, aspirin, a non-steroidal anti-inflammatory drug, as described herein, a cyclooxygenase-2-specific inhibitor, as described herein, dextropropoxyphene, co-codamol, an opioid (e.g., morphine, codeine, oxycodone, hydrocodone, dihydromorphine, pethidine, buprenorphine, tramadol, or methadone), fentanyl, procaine, lidocaine, tetracaine, dibucaine, benzocaine, p-butylaminobenzoic acid 2-(diethylamino) ethyl ester HCl, mepivacaine, piperocaine, dyclonine, or venlafaxine); one or more antibiotics (e.g., cephalosporin, bactitracin, polymyxin B sulfate, neomycin, bismuth tribromophenate, or polysporin); one or more antifungals (e.g., nystatin); one or more anti-inflammatory agents (e.g., a non-steroidal anti-inflammatory drug (NSAID, e.g., ibuprofen, ketoprofen, flurbiprofen, piroxicam, indomethacin, diclofenac, sulindac, naproxen, aspirin, ketorolac, or tacrolimus), a cyclooxygenase-2-specific inhibitor (COX-2 inhibitor, e.g., rofecoxib (Vioxx®), etoricoxib, and celecoxib (Celebrex®)), a glucocorticoid agent, a specific cytokine directed at T lymphocyte function), a steroid (e.g., a corticosteroid, such as a glucocorticoid (e.g., aldosterone, beclometasone, betamethasone, cortisone, deoxycorticosterone acetate, dexamethasone, fludrocortisone acetate, hydrocortisone, methylprednisolone, prednisone, prednisolone, or triamcinolone) or a mineralocorticoid agent (e.g., aldosterone, corticosterone, or deoxycorticosterone)), or an immune selective anti-inflammatory derivative (e.g., phenylalanine-glutamine-glycine (FEG) and its D-isomeric form (feG))); one or more antimicrobials (e.g., chlorhexidine gluconate, iodine (e.g., tincture of iodine, povidone-iodine, or Lugol's iodine), or silver, such as silver nitrate (e.g., as a 0.5% solution), silver sulfadiazine (e.g., as a cream), or Ag<+>in one or more useful carriers (e.g., an alginate, such as Acticoat® including nanocrystalline silver coating in high density polyethylene, available from Smith & Nephew, London, U.K., or Silvercel® including a mixture of alginate, carboxymethylcellulose, and silver coated nylon fibers, available from Systagenix, Gatwick, U.K.; a foam (e.g., Contreet® Foam including a soft hydrophilic polyurethane foam and silver, available from Coloplast A/S, Humlebaek, Denmark); a hydrocolloid (e.g., Aquacel® Ag including ionic silver and a hydrocolloid, available from Conva Tec Inc., Skillman, N.J.); or a hydrogel (e.g., Silvasorb® including ionic silver, available from Medline Industries Inc., Mansfield, Mass.)); one or more antiseptics (e.g., an alcohol, such as ethanol (e.g., 60-90%), 1-propanol (e.g., 60-70%), as well as mixtures of 2-propanol/isopropanol; boric acid; calcium hypochlorite; hydrogen peroxide; manuka honey and/or methylglyoxal; a phenol (carbolic acid) compound, e.g., sodium 3,5-dibromo-4-hydroxybenzene sulfonate, trichlorophenylmethyl iodosalicyl, or triclosan; a polyhexanide compound, e.g., polyhexamethylene biguanide (PHMB); a quaternary ammonium compound, such as benzalkonium chloride (BAC), benzethonium chloride (BZT), cetyl trimethylammonium bromide (CTMB), cetylpyridinium chloride (CPC), chlorhexidine (e.g., chlorhexidine gluconate), or octenidine (e.g., octenidine dihydrochloride); sodium bicarbonate; sodium chloride; sodium hypochlorite (e.g., optionally in combination with boric acid in Dakin's solution); or a triarylmethane dye (e.g., Brilliant Green)); one or more antiproliferative agents (e.g., sirolimus, tacrolimus, zotarolimus, biolimus, or paclitaxel); one or more emollients; one or more hemostatic agents (e.g., collagen, such as microfibrillar collagen, chitosan, calcium-loaded zeolite, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g., II, V, VII, VIII, IX, X, XI, XIII, or Von Willebrand factor, as well as activated forms thereof), a procoagulant (e.g., propyl gallate), an anti-fibrinolytic agent (e.g., epsilon aminocaproic acid or tranexamic acid), and the like); one or more procoagulative agents (e.g., any hemostatic agent described herein, desmopressin, coagulation factor(s) (e.g., II, V, VII, VIII, IX, X, XI, XIII, or Von Willebrand factor, as well as activated forms thereof), procoagulants (e.g., propyl gallate), antifibrinolytics (e.g., epsilon aminocaproic acid), and the like); one or more anticoagulative agents (e.g., heparin or derivatives thereof, such as low molecular weight heparin, fondaparinux, or idraparinux; an anti-platelet agent, such as aspirin, dipyridamole, ticlopidine, clopidogrel, or prasugrel; a factor Xa inhibitor, such as a direct factor Xa inhibitor, e.g., apixaban or rivaroxaban; a thrombin inhibitor, such as a direct thrombin inhibitor, e.g., argatroban, bivalirudin, dabigatran, hirudin, lepirudin, or ximelagatran; or a coumarin derivative or vitamin K antagonist, such as warfarin (coumadin), acenocoumarol, atromentin, phenindione, or phenprocoumon); one or more immune modulators, including corticosteroids and non-steroidal immune modulators (e.g., NSAIDS, such as any described herein); one or more proteins; or one or more vitamins (e.g., vitamin A, C, and/or E).

For the skin tightening methods described herein, the use of anticoagulative and/or procoagulative agents may be of particular relevance. For instance, by controlling the extent of bleeding and/or clotting in the incisions and/or excisions, the skin tightening effect can be more effectively controlled. Thus, in some embodiments, the methods and devices herein include one or more anticoagulative agents, one or more procoagulative agents, one or more hemostatic agents, or combinations thereof. In particular embodiments, the therapeutic agent controls the extent of bleeding and/or clotting in the treated skin region, including the use one or more anticoagulative agents (e.g., to inhibit clot formation prior to skin healing or slit/hole closure) and/or one or more hemostatic or procoagulative agents.

Methods for Treating Skin Regions

The present invention relates to methods and devices that can be applied to treated skin regions. In particular embodiments, these regions are treated with one or more procedures to improve skin appearance. Accordingly, the stretching/compression device, and methods herein can be useful for skin rejuvenation (e.g., removal of pigment, tattoo removal, veins (e.g., spider veins or reticular veins), and/or vessels in the skin) or for treating acne, allodynia, blemishes, ectopic dermatitis, hyperpigmentation, hyperplasia (e.g., lentigo or keratosis), loss of translucency, loss of elasticity, melasma (e.g., epidermal, dermal, or mixed subtypes), photodamage, rashes (e.g., erythematous, macular, papular, and/or bullous conditions), psoriasis, rhytides (or wrinkles, e.g., crow's feet, age-related rhytides, sun-related rhytides, or heredity-related rhytides), sallow color, scar contracture (e.g., relaxation of scar tissue), scarring (e.g., due to acne, surgery, or other trauma), skin aging, skin contraction (e.g., excessive tension in the skin), skin irritation/sensitivity, skin laxity (e.g., loose or sagging skin or other skin irregularities), striae (or stretch marks), vascular lesions (e.g., angioma, erythema, hemangioma, papule, port wine stain, rosacea, reticular vein, or telangiectasia), or any other unwanted skin irregularities.

Such treatments can be included any parts of the body, including the face (e.g., eyelid, cheeks, nose, forehead, chin, forehead, lips, or nose), neck, chest (e.g., as in a breast lift), arms, legs, buttocks and/or back. Accordingly, the devices on the invention can be arranged or configured to be amenable to the size or geometry of different body regions. Such arrangements and configurations can include any useful shape (e.g., linear, curved, or stellate), size, and/or depth.

In some embodiments, the incised or excised tissue portions forms a hole in the skin region. In further embodiments, the tissue portion has a diameter or width that is less than about 2.0 mm and a length of more than about 1.0 mm. In particular embodiments, relatively small dimensions of the tissue portions can promote healing while minimizing the formation of scars.

Furthermore, the fractional treatment resulting in a plurality of tissue portions can be incised or excised in any beneficial pattern within the skin region. Exemplary patterns within the skin region include tile patterns or fractal-like shapes, where the array of hollow tubes can be arranged, e.g., in a base, to effectuate such a pattern (see FIGS. 23-25). It should be emphasized that according to one embodiment of the present invention, there can be an overlap between one coring step to the other (by vertex or facet); and, according to another embodiment of the present invention there can an overlap in the cross section between consecutive coring steps (as can be seen in FIG. 23). In other words, the first cross section area of the first coring step is, as shown, e.g., in FIG. 23, is hexagonal. The next step, according to one embodiment of the present invention, could provide coring in any location within said hexagonal cross section of the first step.

According to another embodiment of the present invention, a higher density and/or smaller spacing of tissue portions (e.g., slits and/or holes) can be incised or excised in the skin in center of the pattern or in thicker portions of the skin. In another example, the pattern within the skin can be random, staggered rows, parallel rows, a circular pattern, a spiral pattern, a square or rectangular pattern, a triangular pattern, a hexagonal pattern, a radial distribution, or a combination of one or more such patterns of the incised or excised tissue portions. The pattern can arise from modifications to the average length, depth, or width of an incised or excised tissue portion, as well as the density, orientation, and spacing between such incisions and/or excisions (e.g., by using an apparatus having one or more blades or tubes with differing lengths, widths, or geometries that are arranged in a particular density or spacing pattern). Such patterns can be optimized to promote unidirectional, non-directional, or multidirectional contraction or expansion of skin (e.g., in the x-direction, y-direction, x-direction, x-y plane, y-z plane, x-z plane, and/or xyz-plane), such as by modifying the average length, depth, width, density, orientation, and/or spacing between incisions and/or excisions.

Any useful portion of the skin can be incised or excised. Such tissue portions can include epidermal tissue, dermal tissue, and/or cells or tissue proximal to the dermal/fatty layer boundary (e.g., stem cells).

According to another embodiment of the present invention, the holes in the tissue (resulting in removing tissue or one or more tissue portions from a skin region—the excised tissue) could be achieved by using a scalpel, application of energy (e.g., laser), coblation, coagulation, ultrasound, microwave energy, RF, application of heat (to evaporate skin portions), mechanical applicator that 'drills' through the skin whilst suction is applies (during the drilling or thereafter) to removes the excised skin portion, or any another instrument. For example, an excision includes any removed tissue or tissue portion from a skin region, which can result in excised tissue portions having a particular geometry (e.g., a cylindrical geometry, rectangular, triangle etc. or any arbitrary shape) and produce one or more holes (i.e., negative space created by the removal of tissue) in the skin region. Exemplary methods of forming excised tissue portions or excisions include use of one or more hollow needles (optionally include one or more notches, extensions, protrusions, and/or barbs), one or more microaugers, one or more microabraders, any useful tool for forming excisions, or any methods and apparatuses described herein.

Safety Subsystem

According to one embodiment of the present invention, the following safety issues are taken into account.

- Emergency Power Off switch that immediately removes all energy and motions from the system
  - all operative robotic arms stopes and descends slowly to rest in case of total power loss
  - Needles/Punches are automatically retracted to safe location within mechanism in case of loss of power
  - all Robotics arms are integrated with force sensors that can detect excessive forces and stop immediately
  - speed of movement is limited during treatment to below 500 mm/sec and below 50 mm/sec while moving from one coring location to another
  - movements during coring are limited to 20 mm and maximum allowed orientation is less than 10 degrees
  - Imaging system continuously monitors distance between punches and skin
- All computer-controlled movements are initiated by the user. These movements can be quickly stopped via the user interface.

Figure 33:
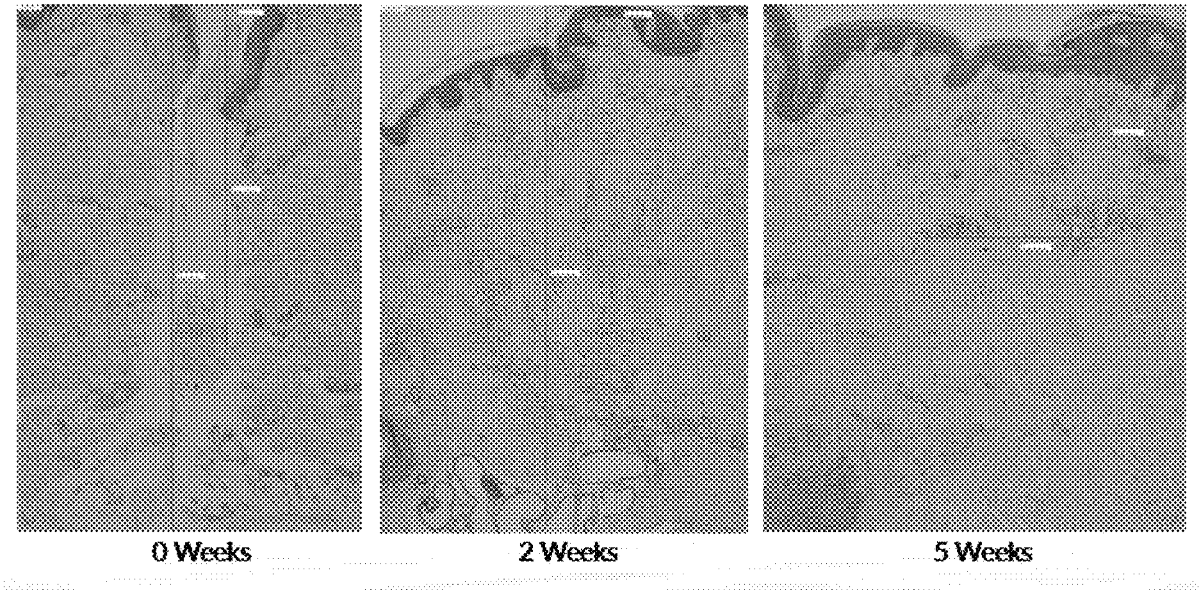
FIG. 33 illustrates histological analysis—cross tissue sections after 0, 2 and 5 weeks post the fractional coring (tissue removal) treatment.

Reference is now made to FIG. 33 illustrating histological analysis—cross tissue sections after 0, 2 and 5 weeks post the fractional coring (tissue removal) treatment.

As can be seen in the FIG. 33, immediately after the treatment (at 0 weeks), fractional holes have been created post the excision of the cored tissue.

After 2 and 5 weeks, healing including fibroblasts migration and collagen synthesis as well as maturation occurred and the skin was tightened.

According to another embodiment of the present invention the excised tissue could be according to any embodiment as disclosed above, however, the directional tightening thereof could also be performed by application of at least one energy source being selected from a group consisting of application of temperature to heat and evacuate tissue, application of laser, RF, coblation, coagulation, microwave energy, ultrasound, application of any other type of energy and any combination thereof.

In such an embodiment, for example, an RF electrode could be applied either to the entire treated skin region or to the area between each excised region Reference is now made to FIGS. 31A, 31B, 31C, 31D and 32 schematically illustrating such an embodiment.

Figure 31A:
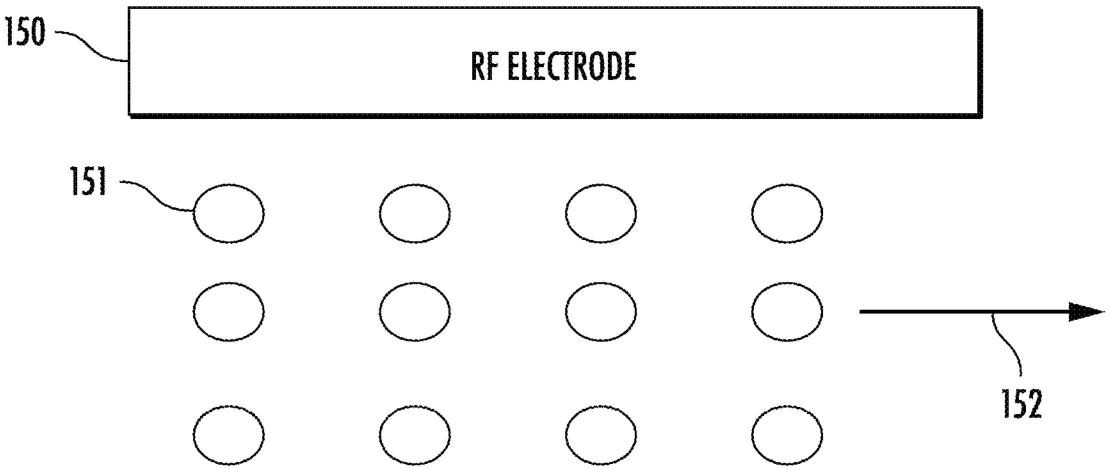
FIGS. 31A, 31B, 31C, 31D and 32 illustrate another embodiment of the directional tightening method and device according to the present invention.

In FIG. 31A schematically illustrated the skin region in which plurality of excisions 150 have been produced. In this figure, also integrated is an RF electrode 150 which post the excision are adapted to apply energy to the skin to provide the directional tightening. It is within the scope of the present invention that once the RF energy is applied to the tissue a different magnetic field would be created in between the excised tissue so as to provide skin tightening (see arrow 152).

Figure 31B:
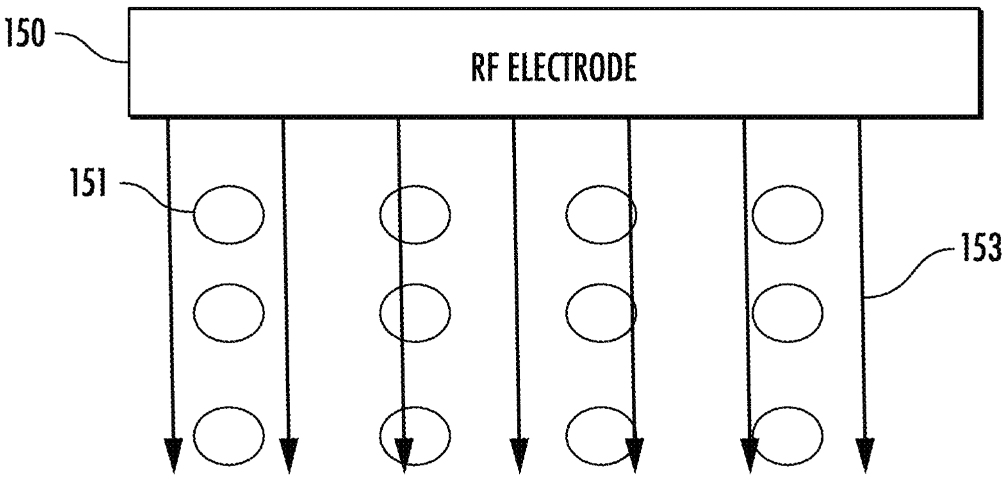
Figure 31C:
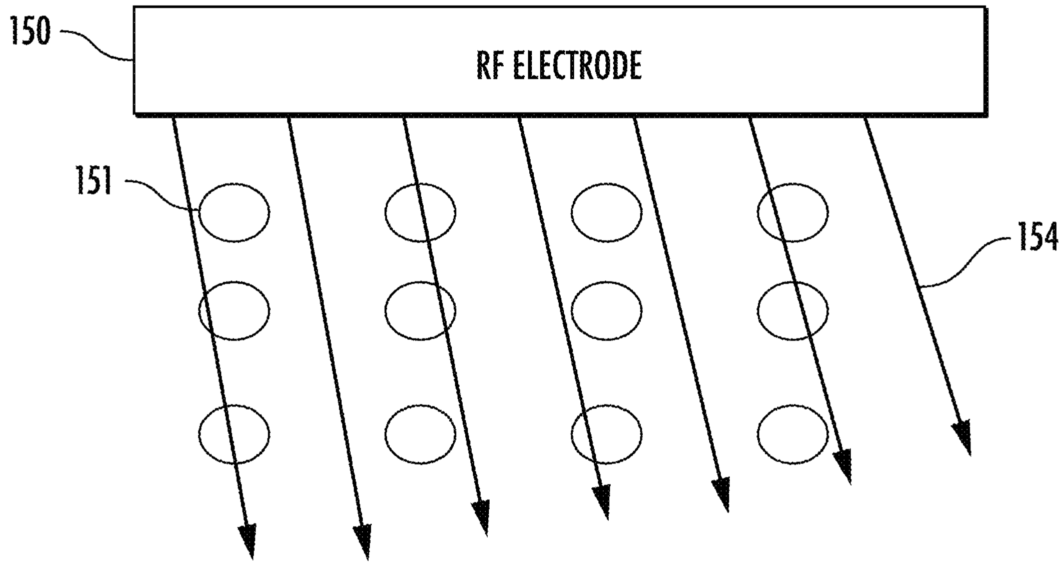

It should be noted that the energy applied by the RF electrode (or a different energy source) could be e.g., as illustrated in FIG. 31B (see arrow 153) or 15*c* (see arrow 154).

Figure 31D:
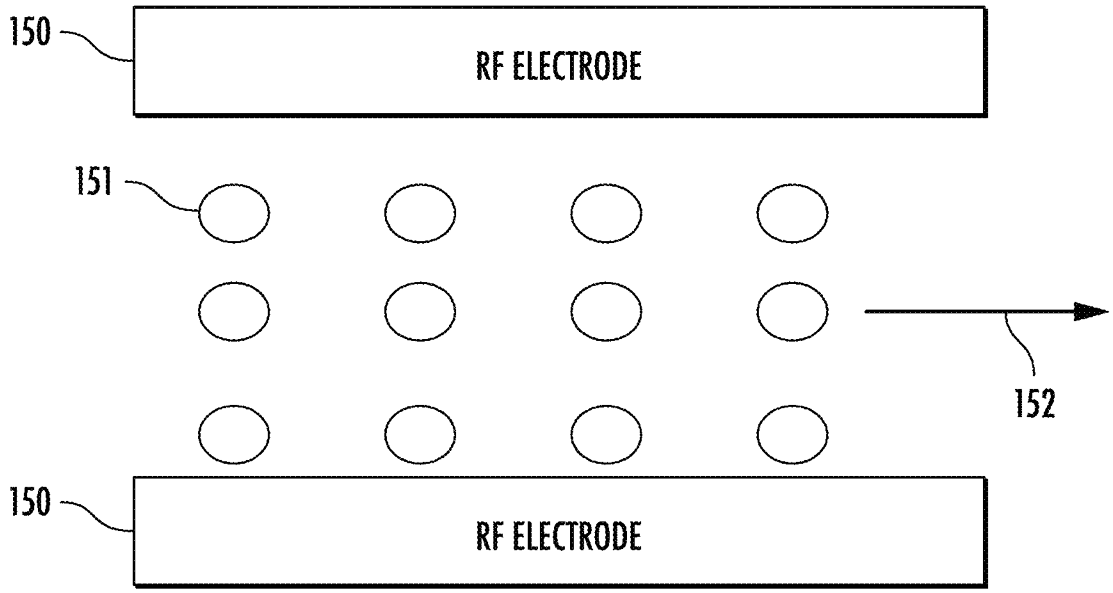

According to another embodiment, when applicable, 2 RF electrodes are employed (each from a different side of the skin), see FIG. 31D.

Figure 32:
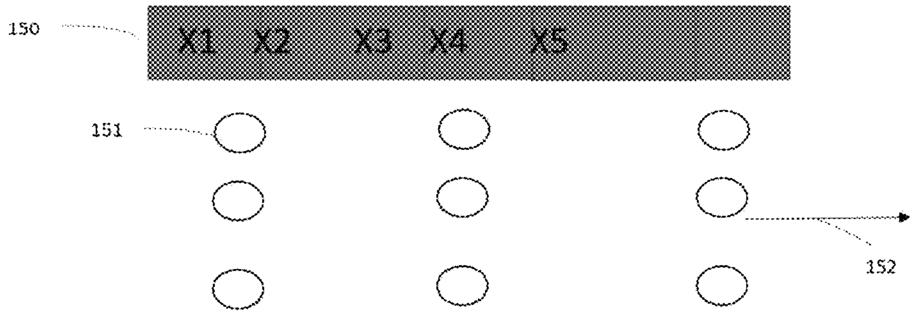

Reference is now made to FIG. 32 which schematically illustrates another embodiment of the present invention, in which the energy applied to the skin tissue (in this case RF energy) is divided into several segments (in the figure illustrates 5 segments X1 . . . X5), each section is adapted to apply a different amount of energy to the tissue. Such energy level could be adjusted to optimize the treatment.

It should be emphasized that although FIGS. 31A, 31B, 31C, 31D and 32 illustrates RF electrode and RF energy, the same applies to application of laser, RF, pulsed electromagnetic field, coblation, coagulation, microwave energy, ultrasound, application of any other type of energy and any combination thereof.

Combined Energy-Based Coring with Mechanical-Based Coring

According to another embodiment of the present invention, the punches/needles are also adapted to apply RF energy to the skin and tissue.

According to such an embodiment, the punches/needles are adapted to penetrate and core the skin (to produce a plurality of excised tissue portions) and either simultaneously or sequentially deliver RF energy to provide heat to the tissue and to fractional ablate/coagulate the tissue. In such an embodiment, the punches/needles are basically an RF electrode as well as a cutting element.

It is within the scope of the present invention, where the application of RF energy to the skin will facilitate the tissue excision as well as apply ablative and coagulative wound healing derived impact to the tissue.

According to one embodiment, each punch/needle is in communication with at least one RF generator.

According to another embodiment, all punches/needles are in communication with at least one RF generator.

According to another embodiment of the present invention, pulsed electromagnetic frequency generator is in communication with at least one of said punches/needles. According to another embodiment, the pulsed electromagnetic frequency generator is adapted to provide a dynamic magnetic field such that electromagnetic pulses are delivered to said region of a patient's skin. According to another embodiment, said electromagnetic pulses vary with time.

According to another embodiment, the dynamic magnetic field is provided by means of at least one coil. According to another embodiment, at least one of the punches/needles is at least partially coiled by at least one coil. According to another embodiment, all the punches/needles are at least partially coiled by one coil.

According to another embodiment of the present invention, all of said punches/needles are adapted to simultaneously provide said electromagnetic pulses to said region of a patient's skin and apply RF energy. According to one embodiment of the present invention said RF energy is provided in the shape of heat to said region of a patient's skin.

According to another embodiment of the present invention, a control unit (controller) monitors and/or controls said the application of heat (by means of the RF energy) to the tissue within said region of skin.

According to another embodiment of the present invention, the shape of said electromagnetic pulse is selected from the group consisting of square wave, a sine wave, a triangular wave, sawtooth wave, ramp waves, spiked wave or any combination thereof.

According to another embodiment of the present invention, the magnetic field intensity B of each pulse applied by said pulsed electromagnetic frequency generator ranges between about 0 and about 3 Tesla.

According to another embodiment of the present invention, the duration of each pulse applied by said pulsed electromagnetic frequency generator ranges between about 3 and about 1000 milliseconds.

According to another embodiment of the present invention, the frequency F applied by the pulses of said pulsed electromagnetic frequency generator ranges between about 1 Hz and about 40 MHz.

According to another embodiment of the present invention, the energy E applied by the pulses of said pulsed electromagnetic frequency generator ranges between about 1 and about 150 watts per pulse or any combination thereof.

According to another embodiment of the present invention, the frequency F applied by the pulses applied by said step of applying pulsed electromagnetic therapy to said region to be higher than about 1 and lower than about 1 MHz.

According to another embodiment of the present invention, the frequency F applied by said electromagnetic field pulses ranges between 1 Hz and 50 Hz.

According to another embodiment of the present invention, the frequency of said RF energy pulses ranges between 200 kHz and 40 MHz.

According to another embodiment of the present invention, the power P applied by said RF energy pulses ranges between 1 W and 100 W of RMS average power.

According to another embodiment of the present invention, at least one temperature sensor is provided.

According to another embodiment of the present invention, the temperature T the tissue reaches is higher than about 30 and lower than about 100 degrees.

According to another embodiment of the present invention, a mechanism for skin cooling is provided to regulate the temperature of the skin (applied by the RF energy).

Impedance/Temperature Measurements

According to another embodiment of the present invention, at least one impedance/temperature sensor(s) (e.g., an impedance sensor and/or a temperature sensor, or a combination sensor) is embedded in the distal-most end of at least one of the punches to provide indication as to the depth of penetration of each of at least one of the punches. Such information can be utilized to indicate if each punch is within the preferred treatment zone or outside thereof.

Cutting Element

According to another embodiment of the present invention, the skin coring instrument (namely, the punches/needles) comprise at least one cutting element (e.g., at least one blade), adapted to grind/mil the cored/excised tissue so as to facilitate extraction thereof.

The at least one cutting element could be integrated in the punches/needles or in communication therewith.

As stated above, according to one object of the present invention, the system comprises at least one vacuum subsystem adapted to apply suction to remove excising portions of said skin tissue. Combining the at least one cutting element in the system will facilitate the extraction of the excised tissue by said vacuum subsystem. Alternatively, the cutting element will facilitate the removal of the cored/excised tissue with the aid of the retention member.

Injectable Matter

According to another embodiment of the present invention, at least one needle is provided with the punches, to inject treatment substances to the treatment area.

According to another embodiment of the present invention, the punches are needles adapted to inject treatment substances to the treatment area.

According to another embodiment of the present invention, the needles could be with either of a homogeneous/heterogeneous size.

According to another embodiment of the present invention, the substance could be selected from a group consisting of hyaluronic acid, botox, collagen, stem cells or any of the adhesives described above.

According to another embodiment of the present invention, in each of the methods as defined above the treatment is repeated more than once.

According to another embodiment of the present invention, each of the methods as defined above additionally comprising step of selecting the shape of said electromagnetic pulse is selected in a non-limiting manner from a group consisting of square wave, a sine wave, a triangular wave, sawtooth wave, ramp waves, spiked wave or any other mathematical combination.

It should also be appreciated that the above-described description of methods and apparatus are to be interpreted as including apparatus for carrying out the methods, and methods of using the apparatus of any type as well known to a person or ordinary skill, and which need not be described in detail herein for enabling a person of ordinary skill to practice the invention.

For the main embodiments of the invention, the particular selection of type and model is not critical, though where specifically identified, this may be relevant. The present invention has been described using detailed descriptions of embodiments thereof that are provided by way of example and are not intended to limit the scope of the invention. No limitation, in general, or by way of words such as “may”, “should”, “preferably”, “must”, or other term denoting a degree of importance or motivation, should be considered as a limitation on the scope of the claims or their equivalents unless expressly present in such claim as a literal limitation on its scope. It should be understood that features and steps described with respect to one embodiment may be used with other embodiments and that not all embodiments of the invention have all of the features and/or steps shown in a particular figure or described with respect to one of the embodiments. That is, the disclosure should be considered complete from combinatorial point of view, with each embodiment of each element considered disclosed in conjunction with each other embodiment of each element (and indeed in various combinations of compatible implementations of variations in the same element). Variations of embodiments described will occur to persons of the art. Furthermore, the terms “comprise,” “include,” “have” and their conjugates, shall mean, when used in the claims, “including but not necessarily limited to.” Each element present in the claims in the singular shall mean one or more element as claimed, and when an option is provided for one or more of a group, it shall be interpreted to mean that the claim requires only one member selected from the various options, and shall not require one of each option. The abstract shall not be interpreted as limiting on the scope of the application or claims.

It is noted that some of the above described embodiments may describe the best mode contemplated by the inventors and therefore may include structure, acts or details of structures and acts that may not be essential to the invention and which are described as examples. Structure and acts described herein are replaceable by equivalents performing the same function, even if the structure or acts are different, as known in the art. Therefore, the scope of the invention is limited only by the elements and limitations as used in the claims.

EXAMPLES

Examples are given in order to prove the embodiments claimed in the present invention. The example, which is a clinical test, describes the manner and process of the present invention and set forth the best mode contemplated by the inventors for carrying out the invention, but are not to be construed as limiting the invention.

Example 1

A clinical test was performed to demonstrate the synergic effect of the combined PEMF and the deep tissue diathermy device.

The aim of the example is to evaluate the synergetic effect of the combined technology and compare it to each technology individually.

A multi polar magnetic pulsed synthesizer which simultaneously emits RF and magnetic pulses in varying phases that homogeneously cause supra normal temperatures over the treated area and penetrates the dermis and hypodermis was used.

Method

The test included 40 women at the age of 42-61 years.

They were divided to 4 groups; 1 study group and 3 control groups, each group included 10 clients. All participants were selected very punctiliously according to predefined criterions which included loosen skin in the forehead, eyes and neck area.

All groups were treated for skin tightening of the face (forehead & eyes) and neck. In all groups the right side of the face and neck was treated only by the use of combined technology and the left side of the face and neck was treated according the following:

Study group: the combined technology as well.

First control group: RF technology.

Second control group: PMF (Pulsed Magnetic Field) technology.

Third control group: PMF technology and 2 hours later RF technology.

Sessions were conducted once a week for a period of 8 weeks.

Each session lasted 40 minutes (20 minutes each side) except of the third control group which lasted 60 minutes (right side 20 minutes and left side 40 minutes because we used 2 different technologies).

Clinical results were collected in two paths; objective and subjective.

Objective Method

Objective method was conducted by taking photographs in order to assess the changes in the tightness of the skin induced by the treatments.

The pictures were taken before and after treatments by the same operator under the same conditions. The pictures were taken while the participant sat in front of a chart with vertical and horizontal lines with the camera placed at the same height distance and with the same lightening conditions.

Subjective Method

Subjective method was conducted by clients' self report.

The subjective method was conducted by questions that each client had to fill after every treatment, referring the immediate results they had noticed on each treated side, the notice of accumulative effect, the satisfaction of the patients from the results, sensation of the treatments etc.

The patients received satisfaction questionnaire which included yes/no questions and questions to be grade on 1 to 5 satisfaction scales (1—represents "Not At All" and 5 represents "Very Much").

Additionally there were open questions adapted to enable the patients the ability to express any kind of feeling following the treatments.

The following questionnaire was handed to the patients after each treatment (except of specific questions):

| | Question | Score | Full Answer |
|---|---|---|---|
| | Do you see any visual changes on the right side that was treated? Please describe in the "Full Answer" column. | Not at all ... Very much<br>1 \| 2 \| 3 \| 4 \| 5 | |
| | Are you satisfied from the visual changes on the right side that was treated? | Not at all ... Very much<br>1 \| 2 \| 3 \| 4 \| 5 | |
| | Is there any specific feeling you feel on the right side that was treated (tightness, lifting, stretched, fullness, swelled, loosen, ache, scratching)? Please describe in the "Full Answer" column. | Yes/No | |
| | Are you satisfied from the feeling you feel on the right side that was treated? | Not at all ... Very much<br>1 \| 2 \| 3 \| 4 \| 5 | |
| | Do you see any visual changes on the left side that was treated? Please describe in the "Full Answer" column. | Not at all ... Very much<br>1 \| 2 \| 3 \| 4 \| 5 | |
| | Are you satisfied from the visual changes on the left side that was treated? | Not at all ... Very much<br>1 \| 2 \| 3 \| 4 \| 5 | |
| | Is there any specific feeling you feel on the left side that was treated (tightness, lifting, stretched, fullness, swelled, loosen, ache, scratching)? Please describe in the "Full Answer" column. | Yes/No | |
| | Are you satisfied from the feeling you feel on the left side that was treated? | Not at all ... Very much<br>1 \| 2 \| 3 \| 4 \| 5 | |
| Answer only from the second treatment | How long did the visual results last on the right side that was treated (Please describe in the "Full Answer" column)? | | |

-continued

| | Question | Score | Full Answer |
|---|---|---|---|
| Answer only from the second treatment | How long did the visual results last on the left side that was treated (Please describe in the "Full Answer" column)? | | |
| Answer only after the $5^{th}$ treatment | Do you feel that the results on the left side that was treated were accumulated from the first treatment? | Yes/No | |
| Answer only after the $5^{th}$ treatment | Do you feel that the results on the right side that was treated were accumulated from the first treatment? | Yes/No | |
| Answer after the $8^{th}$ treatment | Do you feel that the results on the left side that was treated were accumulated from the first treatment? | Yes/No | |
| Answer after the $8^{th}$ treatment | Do you feel that the results on the right side that was treated were accumulated from the first treatment? | Yes/No | |
| General comments | | | |

Results

Study Group

All patients have shown immediate and highly noticeable results on both sides, after the first treatment; the skin tightness of the face and neck increased, it was smoother and with less wrinkles.

Further, after 5 treatments it was noticeable that the results were accumulated (based on comparison between pictures before the first treatment and pictures before the $5^{th}$ treatment). After 8 treatments the skin tightness increased significantly. All clients indicated great satisfaction from the immediate visual results (tightness & stretched) as well as the long term results.

The average score of visual results and satisfaction on the right treated side was 4.66 (on 1 to 5 scale) and on the left treated side the average score was 4.8. 100% of the clients reported that the results on both sides remained all week along the sessions and were accumulated.

They report feeling of tightness, firm and highly comfort during the treatment in terms of the sensation ("Feels like hot stones massage") and expressed satisfaction from the sort time of the treatment.

Reference is now made to FIGS. 13A-13C which are pictures of one patient out of the study group treated with the device of the present invention. The pictures were taken before the treatment (see FIG. 13A1 for the forehead and FIG. 13A2 for the neck), after the first treatment (see FIG. 13B1 for the forehead and FIG. 13B2 for the neck) and after the $8^{th}$ treatment (see FIG. 13C1 for the forehead and FIG. 13C2 for the neck).

First Control Group

All patients have shown immediate results on both sides, after the first treatment. However the results were more significant in terms of tightening and wrinkles fading on the right side compare to the left side.

The average score of visual results and satisfaction on the right treated side was 4.93 compare to the left treated side which was 4.8.

Following 5 treatment it was noticeable that the results were accumulated significantly on the right side in comparison to the results on the left side which lasted only for few days. 90% of the clients reported that the results on the right side remained all week along the first 5 treatments and were accumulated compare to 40% of the clients that reported maintenance of the results on the left side.

After 8 treatments the skin tightness increased even more on the right side and 100% of the clients reported accumulative results compare to the results of the left side which remained almost the same and only 50% of the clients reported maintenance of the results.

Both clients indicated higher satisfaction from the immediate and long term results on the right side compare to the left side. No difference between both treated sides in terms of comfort was expressed.

Reference is now made to FIGS. 14A1-14C2 which are pictures of one patient out of the first control group treated with the device of the present invention on the right side and RF on the left side. The pictures were taken before the treatment (see FIG. 14A1 for the forehead and FIG. 14A2 for the neck), after the first treatment (see FIG. 14B1 for the forehead and FIG. 14B2 for the neck) and after the $8^{th}$ treatment (see FIG. 14C1 for the forehead and FIG. 14C2 for the neck).

Second Control Group

All patients have shown immediate and very noticeable results (skin tightening and wrinkles fading) on the right side after the first treatment and the results have improved after the $5^{th}$ and the $8^{th}$ treatment.

The average score of visual results and satisfaction on the right treated side was 5.00 compare to the left treated side which was only 1.9.

It should be pointed out that on the left side they didn't show any results in terms of skin tightness along the treatments, although after the $4^{th}$ treatment the skin showed some improvement (it looked more glowing and nourished).

All clients indicated high satisfaction from the immediate and long term results on the right side. 100% of the clients reported that the results on the right side remained all week along the first 5 treatments and were accumulated (and up to the $8^{th}$ treatment) compare to 10% of the clients that reported maintenance of the results on the left side.

As for the left side, they reported after the $5^{th}$ treatment satisfaction from the improved skin's condition and look, although they expressed some disappointment from not having results in terms of skin tightening. They reported high comfort in terms of the treatment sensation during the treatment of both sides.

Reference is now made to FIGS. 15A1-15C2 which are pictures of one patient out of the second control group treated with the device of the present invention on the right side and PEMF on the left side. The pictures were taken before the treatment (see FIG. 15A1 for the forehead and FIG. 15A2 for the neck), after the first treatment (see FIG. 15B1 for the forehead and FIG. 15B2 for the neck) and after the $8^{th}$ treatment (see FIG. 15C1 for the forehead and FIG. 15C2 for the neck).

Third Control Group

All patients have shown on the right side very noticeable immediate and accumulative results (skin tightening and wrinkles fading).

The satisfaction was very high.

On the left side visual results are seen; the immediate results were similar to the right side, however the accumulative results were less significant and noticeable compare with the left side.

The average score of visual results and satisfaction on the right treated side was 4.83 compare to the left treated side which was only 2.36.

90% of the clients reported that the results on the right side remained all week along the first treatments (and up to the $8^{th}$ treatment) and were accumulated.

Only 30% of the clients reported maintenance of the results on the left side. In term of satisfaction the clients expressed inconvenient due to the long duration of the treatment.

Reference is now made to FIGS. 16A1-16C2 which are pictures of one patient out of the third control group treated with the device of the present invention on the right side. The left side was treated with PEMF followed by RF. The pictures were taken before the treatment (see FIG. 16A1 for the forehead and FIG. 16A2 for the neck), after the first treatment (see FIG. 16B1 for the forehead and FIG. 16B2 for the neck) and after the $8^{th}$ treatment (see FIG. 16C1 for the forehead and FIG. 16C2 for the neck).

The following tables (tables 3 and 4) summaries the results:

TABLE 3 average score (1 to 5 scale) of all participant in each group following all the treatments:

| Question | Study group | Control 1 | Control 2 | Control 3 |
|---|---|---|---|---|
| Do you see any visual changes on the right side that was treated? | 4.7 | 4.9 | 5 | 4.9 |
| Are you satisfied from the visual changes on the right side that was treated? | 4.7 | 5 | 5 | 4.8 |
| Are you satisfied from the feeling you feel on the right side that was treated? | 4.6 | 4.9 | 5 | 4.8 |
| Do you see any visual changes on the left side that was treated? | 4.9 | 2.5 | 1.9 | 2.4 |
| Are you satisfied from the visual changes on the left side that was treated? | 4.8 | 2.6 | 2 | 2.3 |
| Are you satisfied from the feeling you feel on the left side that was treated? | 4.7 | 2.4 | 1.8 | 2.4 |

TABLE 4 results of "Yes/No" Questions of all the patients in each group following all the treatments

| Question | Study group Yes | Study group No | Control 1 Yes | Control 1 No | Control 2 Yes | Control 2 No | Control 3 Yes | Control 3 No |
|---|---|---|---|---|---|---|---|---|
| Is there any specific feeling you feel on the right side that was treated? (tightness, lifting stretched, fullness, swelled, loosen, ache, scratching)? | 80% | 20% | 90% | 10% | 100% | 0% | 80% | 20% |
| Is there any specific feeling you feel on the left side that was treated? (tightness, lifting stretched, fullness, swelled, loosen, ache, scratching)? Answer only after the 5th treatment: | 90% | 10% | 60% | 40% | 40% | 60% | 50% | 50% |
| Do you feel that the results on the left side that was treated were accumulated from the first treatment? Answer only after the 5th treatment: | 100% | 0% | 40% | 60% | 10% | 90% | 30% | 70% |
| Do you feel that the results on the right side that was treated were accumulated from the first treatment? Answer only after the 8th treatment: | 100% | 0% | 90% | 10% | 100% | 0% | 90% | 10% |
| Do you feel that the results on the left side that was treated were accumulated from the first treatment? | 100% | 0% | 50% | 50% | 20% | 80% | 30% | 70% |

TABLE 4-continued results of "Yes/No" Questions of all the patients in each group following all the treatments

| Question | Study group Yes | Study group No | Control 1 Yes | Control 1 No | Control 2 Yes | Control 2 No | Control 3 Yes | Control 3 No |
|---|---|---|---|---|---|---|---|---|
| Answer only after the 8th treatment: | | | | | | | | |
| Do you feel that the results on the right side that was treated were accumulated from the first treatment? | 100% | 0% | 100% | 0% | 100% | 0% | 100% | 0% |

CONCLUSIONS

The synergetic effect of the device of the present invention clearly shows objectively and subjectively superior results when compare to the treatments in which only RF, or only PEMF were used.

It has shown that clients who were treated on the left side with PEMF technology had a much clearer difference between both sides. This is probably since they have not seen any tightness effect on the left side.

In addition it was shown that clients that were treated with the device of the present invention on both sides felt significant changes along the treatment. Yet more, it was harder for them to see the difference between both sides since both sides were treated with the device of the present invention and both sides had improved in the same way. 80%-100% out of all 40 participants answered "Yes" regarding questions concerning the tightness of the skin and the accumulative results on the right treated area. Only 10%-50% that were treated on the left side with other technology answered "Yes" regarding questions concerning the tightness of the skin and the accumulative results.

The results with the combined technology (the device provided by the present invention) were immediate and they maintained and improved from one treatment to the other. Immediate skin tightening has been seen due to the change of collagen fibers formation (they become shorter and thicker and as a result harder) induced by thermal technique of the RF.

Long lasting results have been seen due to the increase of new collagen fibers synthesis by using thermal (RF) and non-thermal (PEMF) technologies induced by the device of the present invention enables the formation change of greater amount of collagen fibers and as a results created physiological buttress that enabled better structural support of the skin.

The assets of the device of the present invention to the medical field are:

Synergistic effect that stimulates dermal fibroblasts which produce new collagen, elastic and reticular fibers by using different mechanisms (Heating & non heating);

Changing the form of a greater amount of collagen fiber by making them shorter and thicker; and, Angiogenesis—increasing the formation of new small blood vessels.

What is claimed is:

1. An apparatus of fractional coring for directional skin tightening, comprising:

(i) an excisor configured to produce a plurality of excised tissue portions in a region of skin tissue; and, (ii) a securing fastener configured to secure, to the region of the skin tissue, a tensioner having at least two portions, the tensioner adapted to provide contraction or expansion of said region in at least one predetermined direction; thereby promoting collagen growth and providing directional skin tightening in said skin tissue;

wherein said excisor is configured to be in communication with at least one RF generator, adapted to provide RF energy, such that said excisor is adapted to provide RF energy to said region of skin tissue;

wherein said producing a plurality of excised tissue portions in a region of skin tissue is performed by a system comprising at least one robotic arm, said at least one robotic arm comprising at least one skin coring instrument; and wherein said at least one skin coring instrument comprises:

a micro-coring punch including a plurality of punches arranged in a predetermined pattern, the plurality of punches comprising at least six punches;

a motor configured to rotate each punches of the plurality of micro-coring punches around at least one axis of symmetry of each punch and wherein rotation of each punch of the plurality of punches is synchronized with the rotation of a remainder of the plurality of punches;

conveyor configured to advance the micro-coring punch towards skin and to position the micro-coring punch to penetrate the skin to a depth of at least two millimeters; and a stepper configured to step a micro-coring punch and locate the micro-coring punch such that at least one element selected from a group consisting of vertex, facet and any combination thereof of a stepped micro-coring punch hexagon is overlapped with at least one element selected from a group consisting of vertex, facet and any combination thereof of a previous micro-coring punch hexagon.

2. The apparatus of claim 1, wherein the excisor is structured to include at least one RF electrode to deliver the RF energy to said region of skin.

3. The apparatus of claim 2, wherein said excisor is in communication with at least one pulsed electromagnetic field frequency generator configured to provide time-varying magnetic pulses.

4. The apparatus of claim 3, wherein said at least one pulsed electromagnetic frequency generator is in communication with at least one coil.

5. The apparatus of claim 4, wherein the at least one RF electrode is surrounded by at least one coil.

6. The apparatus of claim 4, wherein said at least one electrode is adapted to apply heat to the tissue; further wherein said heat is applied before, after or simultaneously with providing magnetic pulses.

7. The apparatus of claim 3, wherein at least one of the following is being held true (a) a shape of the pulses is selected from a group consisting of a square wave, a sine wave, a triangular wave, a sawtooth wave, a ramp wave, and a spiked wave and any combination thereof, (b) a duration of each pulse ranges between about 3 and about 1000 milliseconds; (c) a frequency of said pulses ranges between about 1 Hz and about 1 MHz; (d) a power of said at least one RF electrode ranges between about 1 and about 150 watts per pulse; (e) an intensity of each of said time-varying magnetic pulses is in a range of 0 to 3 Tesla; (f) the intensity of each of said time-varying magnetic pulses is in a range of 0 to 40 Gauss; (g) the frequency applied by said RF electrode ranges between about 1 Hz and about 1M Hz; any combination thereof.

8. The apparatus of claim 1, wherein said tensioner comprises at least one selected from a group consisting of (a) at least one occlusion layer adapted to control humidity and/or promote wound healing of said skin; (b) at least one absorption layer adapted to absorb wound exudate; and any combination thereof.

9. The apparatus of claim 1, wherein said excisor is configured to apply said RF energy to the skin tissue to alter one or more properties thereof.

10. The apparatus of claim 1, wherein said at least one skin coring instrument; said at least one skin coring instrument is configured to contact a surface of the skin to generate holes in the skin tissue by excising portions of the skin tissue.

11. The apparatus of claim 10, wherein the plurality of punches of said at least one skin coring instrument comprises punches.

12. The apparatus of claim 10, wherein at least a portion of said plurality of punches is disposable.

13. The apparatus of claim 1, wherein at least two of said at least one skin coring instrument are characterized by either a similar or substantially different cross section area.

14. The apparatus of claim 1, wherein at least one of the following is being held true (a) said at least one skin coring instrument is adapted to penetrate said skin to a depth of 1 to 4 mm; (b) said at least one skin coring instrument is characterized by a radius of 0.15 mm-2.0 mm; (c) a cross-sectional area of said at least one skin coring instrument is selected from a group consisting of circular, rectangular, triangular, hexagonal, oval, staggered rows, parallel rows, a spiral pattern, a square or rectangular pattern, a radial distribution and any combination thereof.

15. The apparatus of claim 1, wherein said system additionally comprising at least one controller adapted to control a positioning of said at least one robotic arm relatively to said region of skin tissue.

16. The apparatus of claim 15, wherein said at least one controller comprises at least one engine adapted to control at least one parameter selected from a group consisting of a rotation, translation, or angle of penetration of said at least one robotic arm relative to said region of skin tissue, depth of penetration, coverage rate, a diameter of at least one excised tissue multiplied by number of cores, different area of said region of skin tissue to be treated and any combination thereof.

17. The apparatus of claim 16, wherein said parameters are adjusted manually by an operator or automatically by said at least one controller.

18. The apparatus of claim 17, wherein said parameters are real time adjusted.

19. The apparatus of claim 17, wherein at least one of the following is being held true (a) said rotation is at a speed in 4 range of 1000-7000 RPM; (b) said translation is at a speed in range of 0-500 mm/sec; and any combination thereof.

20. The apparatus of claim 16, wherein said at least one controller comprising a stopper adapted to limit a depth to which at least a portion of said at least one skin coring instrument penetrates said skin.

21. The apparatus of claim 20, wherein an angle of penetration is substantially perpendicular to said skin.

22. The apparatus of claim 20, wherein said at least one controller is adapted to define at least one no-fly zone, wherein said at least one no-fly zone is defined as an area to which said system provides no treatment.

23. The apparatus of claim 1, wherein said at least one skin coring instrument comprises a plurality of skin coring instruments each of which is configured to rotate individually in a predefined direction in a predetermined speed.

24. The apparatus of claim 1, wherein said at least one skin coring instrument comprises at least two skin coring instruments which are configured to rotate simultaneously.

25. The apparatus of claim 1, wherein each of said at least one skin coring instrument translates individually.

26. The apparatus of claim 1, wherein at least two of said at least one skin coring instrument translate simultaneously.

27. The apparatus of claim 1, wherein the micro-coring punch is attached to a computer-controlled robotic arm capable of moving in six or more axes corresponding to six degrees of freedom.

28. The apparatus of claim 1, further comprising a video camera configured to provide visual feedback of at least the micro-coring punch and the skin and a closed-loop force sensor to determine when the punches break the skin.

29. The apparatus of claim 1, wherein said apparatus is configured to deliver one or more additives to the skin.

30. The apparatus of claim 29, wherein said additives are selected from a group consisting of therapeutic agents, saline solution growth factors, platelet-derived growth factor (PDGF), transforming growth factor beta (TGF-β), fibroblast growth factor (FGF), epidermal growth factor (EGF), and keratinocyte growth factor); one or more stem cells; steroids, agents which prevent post-inflammatory skin hyperpigmentation, hydroquinone, azelaic acid, kojic acid, mandelic acid, or niacinamide; one or more analgesics; one or more antifungals; one or more anti-inflammatory agents, or a mineralocorticoid agent, an immune selective anti-inflammatory derivative; one or more antimicrobials; a foam; or a hydrogel, one or more antiseptics, one or more antiproliferative agents, one or more emollients; one or more hemostatic agents, a procoagulant, an anti-fibrinolytic agent, one or more procoagulative, one or more anticoagulative agents, one or more immune modulators, including corticosteroids and non-steroidal immune modulators, one or more proteins; or one or more vitamins and any combination thereof.

31. The apparatus of claim 1, wherein said system additionally comprising at least one imaging subsystem adapted to guide said at least one skin coring instrument.

32. The apparatus of claim 31, wherein said imaging subsystem comprises at least one selected from a group consisting at least one camera, under skin imaging, ultrasound-based imaging, OCT and any combination thereof.

33. The apparatus of claim 1, wherein said system additionally comprises at least one vacuum subsystem adapted to apply suction to remove excising portions of said skin tissue.

34. The apparatus of claim 33, wherein said region of skin is part of a treatment area selected from a group consisting of forehead, cheeks, jaw line, nose, forehead neck, upper arms, abdomen, face, eyelid, chin, forehead, lips, nose, neck, buttocks chest, legs, back and any combination thereof.

35. The apparatus of claim 1, wherein said apparatus is configured to allow focal elimination of redundant dermal tissue for skin tightening, at least partially scar removal, skin rejuvenation, at least partially removal of pigment, at least partially tattoo removal, veins, acne, allodynia, blemishes, ectopic dermatitis, hyperpigmentation, hyperplasia, lentigo or keratosis, loss of translucency, loss of elasticity, melasma, photodamage, psoriasis, rhytides, wrinkles, sallow color, scar contracture, scarring, wrinkles, folds, acne scars, dyschromia, striae, surgical scars, cellulite, tattoos removal, cheek wrinkles, facial wrinkles, facial folds, skin aging, skin contraction, skin irritation/sensitivity, skin laxity, striae, vascular lesions, angioma, erythema, hemangioma, papule, port wine stain, rosacea, reticular vein, or telangiectasia, or any other unwanted skin irregularities and any combination thereof.

36. The apparatus of claim 35, wherein said apparatus is configured to carry out at least partially scar removal said producing a plurality of fractionally excised tissue portions results in replacing one type of collagen by a different type to be synthesized post said removal of said excised tissue portions.

37. The apparatus of claim 1, wherein said apparatus utilizes at least one selected from a group consisting of mechanical visualization, OCT, Ultrasound, machine learning algorithms, artificial intelligence, image processing and any combination thereof to efficiency select the region of skin tissue to enhance an outcome of treatment.

38. The apparatus of claim 1, wherein an areal fraction of excised tissue portions is in a range of about 5% to about 30% of the region of skin tissue.

39. The apparatus of claim 1, wherein the at least one skin coring instrument comprises at least one cutter adapted to grind said excised tissue so as to facilitate extraction thereof.

40. The apparatus of claim 1, additionally comprising at least one temperature sensor.

41. The apparatus of claim 40, additionally comprising a cooler adapted to regulate the temperature of the region of skin tissue.

42. The apparatus of claim 1, wherein a distal end of said at least one skin coring instrument additionally comprises at least one selected from a group consisting of at least one impedance, at least one temperature sensor and any combination thereof.

43. The apparatus of claim 42, wherein said at least one selected from a group consisting of at least one impedance sensor, at least one temperature sensor and any combination thereof is adapted to provide an indication as to a depth of penetration of each of said at least one skin coring instrument.

44. The apparatus of claim 1, wherein said at least one skin coring instrument additionally comprising at least one needle, adapted to inject at least one treatment substance to the region of skin tissue.

45. The apparatus of claim 44, wherein said at least one treatment substance is selected from a group consisting of hyaluronic acid, botulinum toxin, collagen, stem cells and any combination thereof.

46. The apparatus of claim 1, wherein said system additionally comprises at least one retainer, in communication with said excisor configured to produce a plurality of excised tissue portions, adapted to contain said excised tissue, without necessitating use of a vacuum.

47. An apparatus of fractional coring for directional skin tightening, comprising:

(i) an excisor configured to produce a plurality of excised tissue portions in a region of skin tissue; and (ii) a fastener configured to secure to the skin region a stretching/compression device, the stretching/compression device having at least two portions and adapted to provide contraction or expansion of said skin region in at least one predetermined direction, thereby promoting collagen growth and providing directional skin tightening in said skin tissue;

wherein said excisor is in communication with at least one RF generator adapted to provide RF energy, such that said excisor is adapted to provide RF energy to said region of skin tissue;

wherein said producing a plurality of excised tissue portions in a region of skin tissue is performed by a system comprising at least one robotic arm, said at least one robotic arm comprising at least one skin coring instrument; and wherein at least one skin coring instrument comprises:

a micro-coring punch including a plurality of punches arranged in a predetermined pattern, the plurality of punches comprising at least six punches;

a motor configured to rotate each punches of the plurality of micro-coring punches around at least one axis of symmetry of each punch and wherein rotation of each punch of the plurality of punches is synchronized with the rotation of a remainder of the plurality of punches;

a conveyor configured to advance the micro-coring punch towards skin and to position the micro-coring punch to penetrate the skin to a depth of at least two millimeters; and a stepper configured to step a micro-coring punch and locate the micro-coring punch such that at least one element selected from a group consisting of vertex, facet and any combination thereof of a stepped micro-coring punch hexagon is overlapped with at least one element selected from a group consisting of vertex, facet and any combination thereof of a previous micro-coring punch hexagon.

48. The apparatus of claim 47, wherein said means of producing a plurality of excised tissue portions in a region of skin tissue is further performed by means selected from a group consisting of application of temperature to heat and evacuate tissue, application of laser, pulsed electromagnetic field, RF, coblation, coagulation, microwave energy, ultrasound, and any combination thereof.

* * * * *